US009243236B2

(12) United States Patent
Bylina et al.

(10) Patent No.: US 9,243,236 B2
(45) Date of Patent: Jan. 26, 2016

(54) GLYCOSIDASE ENZYMES

(71) Applicant: BP Corporation North America Inc., Naperville, IL (US)

(72) Inventors: Edward J. Bylina, Henderson, NV (US); Ronald V. Swanson, Del Mar, CA (US); Eric J. Mathur, Carlsbad, CA (US); David E. Lam, San Elijo Hills, CA (US)

(73) Assignee: BP Corporation North America Inc., Houston, TX (US)

(*) Notice: Subject to any disclaimer, the term of this patent is extended or adjusted under 35 U.S.C. 154(b) by 0 days.

(21) Appl. No.: 14/270,022

(22) Filed: May 5, 2014

(65) Prior Publication Data

US 2014/0323356 A1 Oct. 30, 2014

Related U.S. Application Data

(60) Division of application No. 13/548,583, filed on Jul. 13, 2012, now Pat. No. 8,715,993, which is a division of application No. 13/397,026, filed on Feb. 15, 2012, now abandoned, which is a division of application No. 12/860,691, filed on Aug. 20, 2010, now Pat. No. 8,119,383, which is a division of application No. 11/866,279, filed on Oct. 2, 2007, now Pat. No. 7,807,433, which is a division of application No. 09/134,078, filed on Aug. 13, 1998, now Pat. No. 6,368,844, which is a continuation of application No. 08/949,026, filed on Oct. 10, 1997, now abandoned.

(60) Provisional application No. 60/056,916, filed on Dec. 6, 1996.

(51) Int. Cl.
| | |
|---|---|
| *C12N 9/24* | (2006.01) |
| *C12N 1/20* | (2006.01) |
| *C12N 15/00* | (2006.01) |
| *C12P 21/04* | (2006.01) |
| *C12P 21/06* | (2006.01) |
| *C07H 21/04* | (2006.01) |
| *C12N 9/46* | (2006.01) |
| *C12N 9/38* | (2006.01) |
| *C12N 9/42* | (2006.01) |
| *C12N 9/44* | (2006.01) |
| *C12N 9/40* | (2006.01) |
| *C12P 19/02* | (2006.01) |

(52) U.S. Cl.
CPC ............ *C12N 9/2491* (2013.01); *C12N 9/2402* (2013.01); *C12N 9/2445* (2013.01); *C12N 9/2454* (2013.01); *C12N 9/2457* (2013.01); *C12N 9/2465* (2013.01); *C12N 9/2468* (2013.01); *C12N 9/2494* (2013.01); *C12P 19/02* (2013.01); *C12Y 302/01021* (2013.01); *C12Y 302/01022* (2013.01); *C12Y 302/01023* (2013.01); *C12Y 302/01025* (2013.01); *C12Y 302/01041* (2013.01)

(58) Field of Classification Search
CPC ........ C12N 9/2402; C12N 15/66; C12P 21/02
See application file for complete search history.

(56) References Cited

U.S. PATENT DOCUMENTS

| | | |
|---|---|---|
| 4,557,927 A | 12/1985 | Miyake |
| 5,219,751 A | 6/1993 | Starnes |
| 5,268,280 A | 12/1993 | Starnes |
| 5,395,541 A | 3/1995 | Carpenter |
| 5,470,725 A | 11/1995 | Borriss |
| 5,731,174 A | 3/1998 | DeWeer |
| 5,744,345 A | 4/1998 | Shimada |
| 5,830,696 A | 11/1998 | Short |
| 7,279,316 B2 | 10/2007 | Short |

FOREIGN PATENT DOCUMENTS

| | | |
|---|---|---|
| EP | 0606008 A2 | 7/1994 |
| EP | 0687732 A1 | 12/1995 |
| WO | WO 92/06209 | 4/1992 |
| WO | WO 93/19171 | 9/1993 |
| WO | WO 97/20918 | 6/1997 |
| WO | WO 97/25417 | 7/1997 |
| WO | WO 97/44361 | 11/1997 |
| WO | WO 98/24799 | 6/1998 |

OTHER PUBLICATIONS

Bauer et al., "Beta mannosidase" EMBL Sequence Database, AC Q51733, Nov. 1, 1996.
Bauer et al., *Pyrococcus furiosus* beta-mannosidase (bmnA) gene, complete cds. AC U60214, Jul. 2, 1996.
Bauer—J. Biol. Chem. (1996)—271—23749-23755.
Bhat, "Cellulases and related enzymes in biotechnology," *Biotechnology Advances*, vol. 18, pp. 355-383, Jan. 2000.
Borges et al., "Survey of the Geneome of the Hyperthermophilic Archaeon, *Pyrococcus furiosus*," Database EMBL XP-002160063, May 18, 1996.
Borges—Genome Sci Tech. (1996) 1—37-46.
Branden—Introduction to Protein Structure, Garland Publishing Inc., New York (1991) p. 247.
Bronnenmeier et al., "Purification of *Thermotoga maritima* Enzymes for the Degradation of Cellulosic Materials," *Applied and Environmental Microbiology*, vol. 61, No. 4, pp. 1399-1407, Apr. 1995.
Canganella et al., "Characterization of amylolytic and pullulytic enzymes from thermophilic archaea and from a new *Fervidobacterium* species," *Appl. Microbiol. Biotechnol.*, vol. 42, pp. 239-245, 1994.
Caransa et al., "A novel enzyme application for corn wet milling," Starch/Starke, 40(II):409-411, 1988.

(Continued)

*Primary Examiner* — Yong Pak
(74) *Attorney, Agent, or Firm* — DLA Piper LLP (US)

(57) ABSTRACT

A thermostable glycosidase enzymes derived from various *Thermococcus, Staphylothermus* and *Pyrococcus* organizms is disclosed. The enzymes are produced from native or recombinant host cells and can be utilized in the food processing industry, pharmaceutical industry and in the textile industry, detergent industry and in the baking industry.

3 Claims, 46 Drawing Sheets

(56) References Cited

OTHER PUBLICATIONS

Cubellis et al., *Gene*, 94:89-94, 1990.
Dakhova et al., "*Thermotoga neapolitana* bg1A gene," EMBL Sequence Database, AC Z97212, Jul. 1, 1997.
Dakhova—Biochem. Biophys. Res. Commun. (1993)—194—1359-1364.
Dakhova et al., "*T. neapolitana* lamA gene and bg1B gene" EMBL Sequence Database, AC Z47974, Dec. 31, 1995.
Database Genbank, US National Library of Medicine, (Bethesda, MD, USA) No. PIRJQ0767, Cubellis MV et al., Feb. 1993.
Database Genbank, US National Library of Medicine, (Bethesda, MD, USA) No. AAT93678, Bylina EJ et al., Mar. 1998.
Database Genbank, US National Library of Medicine, (Bethesda, MD, USA) No. AAV36907, Bylina EJ et al., Dec. 1998.
Database Genbank, US National Library of Medicine, (Bethesda, MD, USA) No. PIRS06762, Little S et al., Jun. 1990.
Database Genbank, US National Library of Medicine, (Bethesda, MD, USA) No. AF053078, Chi YI et al., Jul. 1999.
Database Genbank, US National Library of Medicine, (Bethesda, MD, USA) No. PIRB90483, She Q et al., May 2001.
Database Genbank, US National Library of Medicine, (Bethesda, MD, USA) No. AR205078, Bylina EJ, Apr. 2002.
Fontes et al., *Appl. Microbiol. Biotechnol.*, vol. 43(1):52-57, 1995.
Gabelsberger—FEMS (1993)—109—131-138.
Genbank Accession No. CAA04513—*Thermatogra maritime* (1997)—Liebl.
Genbank Accession No. CAA04522—Pullanase [*Thermatogra maritima*] (1998)—Liebl.
Grabnitz—Eur. J. Biochem (1991) 220—301-30.
Kengen—Biocatalysis (1994)—11—79-88.
Kengen—Eur. J. Biochem (1993)—213—305-312.
Leipprandt—Genomics (1996)—37—51-56.
Liebl et al., "Analysis of a *T. maritime* DNA fragment encoding two similar thermostable cellulases CelA and CelB . . . ," *Microbiology*, 142:2532-2542, 1996.
Liebl et al., "Comparative amino acid sequence analysis of *T. maritime* beta-glucosidase (Bg1A) deduced from the nucleotide sequence . . . ," *Mol. Gen. Genet.*, 242(1):111-115, 1994.
Liebl et al., "Properties of an alpha-galactosidase, and structure of its gene, galA, within an alpha- and beta-galactosidase utilization gene cluster of the hyperthermophilic bacterium *Thermotoga maritime*," Database EMBL XP-002160068, Mar. 1998.
Liebl et al., "*Thermotoga maritime* pulA gene," Database EMBL XP-002160070, Aug. 13, 1997.
Love—Mol. Gen. Genet. (1988)—213—84-92.
Moor—Gene (1994)—147—101-106.
Scheirlinck et al., "Cloning and expression of cellulase and xylanase genes in *Lactobacillus plantarum*," *Appl. Microbiol. Biotechnol.*, vol. 33, No. 5, pp. 534-541, Oct. 1990.
Scheirlinck et al., "Integration and Expression of α-Amylase and Endoglucanase Genes in the *Lactobacillus plantarum* Chromosome," *Applied and Environmental Microbiology*, vol. 55, pp. 2130-2137, Sep. 1989.
Sim et al., "Microbial Conversion of Spent Brewery Grains into Soluble Sugars and Proteins," *Microbial Utilization of Renewable Resources*, vol. 6, pp. 220-227, Mar. 1989.
Signoretti et al., "Evaluation of Corn Germ Meal in the Feeding of Dairy Calves," *Revista Brasileira de Zootecnia*, vol. 26, No. 3, pp. 616-622, May-Jun. 1997 (English abstract only).
St. Pierre—Gene (1996)—169—65-68.
Stroeher et al., "Serotype conversion in *Vibrio cholerae* O1," Proc. Natl. Acad. Sci., USA, 89(7):2566-2570, 1992.
Voorhorst—J. Bacteriology (1995)—177—7105-7111.
Yague—Gene (1990)—89—61-67.
Zverlov—Microbiol. (1997)—143—3537-3542.

M11TL GLYCOSIDASE - 29G
COMPLETE GENE SEQUENCE - 9/95

```
TTG AAA TTC CCC AAA GAC TTC ATG ATA GGC TAC TCA TCT TCA CCG TTT    48
Leu Lys Phe Pro Lys Asp Phe Met Ile Gly Tyr Ser Ser Ser Pro Phe
 1           5                  10                  15

CAA TTT GAA GCT GGT ATT CCC GGG TCC GAG GAT CCG AAT AGT GAT TGG    96
Gln Phe Glu Ala Gly Ile Pro Gly Ser Glu Asp Pro Asn Ser Asp Trp
             20                  25                  30

TGG GTA TGG GTG CAT GAT CCG GAG AAC ACA GCA GCT GGA CTA GTC AGC   144
Trp Val Trp Val His Asp Pro Glu Asn Thr Ala Ala Gly Leu Val Ser
         35                  40                  45

GGC GAT TTT CCC GAG AAC GGC CCA GGT TAC TGG AAT TTA AAC CAA AAT   192
Gly Asp Phe Pro Glu Asn Gly Pro Gly Tyr Trp Asn Leu Asn Gln Asn
 50                  55                  60

GAC CAC GAC CTG GCT GAG AAG CTG GGG GTT AAC ACT ATT AGA GTA GGC   240
Asp His Asp Leu Ala Glu Lys Leu Gly Val Asn Thr Ile Arg Val Gly
 65                  70                  75                  80

GTT GAG TGG AGT AGG ATT TTT CCA AAG CCA ACT TTC AAT GTT AAA GTC   288
Val Glu Trp Ser Arg Ile Phe Pro Lys Pro Thr Phe Asn Val Lys Val
             85                  90                  95

CCT GTA GAG AGA GAT GAG AAC GGC AGC ATT GTT CAC GTA GAT GTC GAT   336
Pro Val Glu Arg Asp Glu Asn Gly Ser Ile Val His Val Asp Val Asp
            100                 105                 110

GAT AAA GCG GTT GAA AGA CTT GAT GAA TTA GCC AAC AAG GAG GCC GTA   384
Asp Lys Ala Val Glu Arg Leu Asp Glu Leu Ala Asn Lys Glu Ala Val
        115                 120                 125

AAC CAT TAC GTA GAA ATG TAT AAA GAC TGG GTT GAA ACA GGT AGA AAA   432
Asn His Tyr Val Glu Met Tyr Lys Asp Trp Val Glu Arg Gly Arg Lys
        130                 135                 140

CTT ATA CTC AAT TTA TAC CAT TGG CCC CTG CCT CTC TGG CTT CAC AAC   480
Leu Ile Leu Asn Leu Tyr His Trp Pro Leu Pro Leu Trp Leu His Asn
145                 150                 155                 160

CCA ATC ATG GTG AGA AGA ATG GGC CCG GAC AGA GCG CCC TCA GGC TGG   528
Pro Ile Met Val Arg Arg Met Gly Pro Asp Arg Ala Pro Ser Gly Trp
            165                 170                 175

CTT AAC GAG GAG TCC GTG GTG GAG TTT GCC AAA TAC GCC GCA TAC ATT   576
Leu Asn Glu Glu Ser Val Val Glu Phe Ala Lys Tyr Ala Ala Tyr Ile
            180                 185                 190

GCT TGG AAA ATG GGC GAG CTA CCT GTT ATG TGG AGC ACC ATG AAC GAA   624
Ala Trp Lys Met Gly Glu Leu Pro Val Met Trp Ser Thr Met Asn Glu
        195                 200                 205

CCC AAC GTC GTT TAT GAG CAA GGA TAC ATG TTC GTT AAA GGG GGT TTC   672
Pro Asn Val Val Tyr Glu Gln Gly Tyr Met Phe Val Lys Gly Gly Phe
        210                 215                 220

CCA CCC GGC TAC TTG AGT TTG GAA GCT GCT GAT AAG GCC AGG AGA AAT   720
Pro Pro Gly Tyr Leu Ser Leu Glu Ala Ala Asp Lys Ala Arg Arg Asn
225                 230                 235                 240
```

FIG. 1-1

```
ATG ATC CAG GCT CAT GCA CGG GCC TAT GAC AAT ATT AAA CGC TTC AGT      768
Met Ile Gln Ala His Ala Arg Ala Tyr Asp Asn Ile Lys Arg Phe Ser
                245                 250                 255

AAG AAA CCT GTT GGA CTA ATA TAC GCT TTC CAA TGG TTC GAA CTA TTA      816
Lys Lys Pro Val Gly Leu Ile Tyr Ala Phe Gln Trp Phe Glu Leu Leu
                260                 265                 270

GAG GGT CCA GCA GAA GTA TTT GAT AAG TTT AAG AGC TCT AAG TTA TAC      864
Glu Gly Pro Ala Glu Val Phe Asp Lys Phe Lys Ser Ser Lys Leu Tyr
            275                 280                 285

TAT TTC ACA GAC ATA GTA TCG AAG GGT AGT TCA ATC ATC AAT GTT GAA      912
Tyr Phe Thr Asp Ile Val Ser Lys Gly Ser Ser Ile Ile Asn Val Glu
        290                 295                 300

TAC AGG AGA GAT CTT GCC AAT AGG CTA GAC TGG TTG GGC GTT AAC TAC      960
Tyr Arg Arg Asp Leu Ala Asn Arg Leu Asp Trp Leu Gly Val Asn Tyr
305                 310                 315                 320

TAT AGC CGT TTA GTC TAC AAA ATC GTC GAT GAC AAA CCT ATA ATC CTG     1008
Tyr Ser Arg Leu Val Tyr Lys Ile Val Asp Asp Lys Pro Ile Ile Leu
                325                 330                 335

CAC GGG TAT GGA TTC CTT TGT ACA CCT GGG GGG ATC AGC CCG GCT GAA     1056
His Gly Tyr Gly Phe Leu Cys Thr Pro Gly Gly Ile Ser Pro Ala Glu
                340                 345                 350

AAT CCT TGT AGC GAT TTT GGG TGG GAG GTG TAT CCT GAA GGA CTC TAC     1104
Asn Pro Cys Ser Asp Phe Gly Trp Glu Val Tyr Pro Glu Gly Leu Tyr
            355                 360                 365

CTA CTT CTA AAA GAA CTT TAC AAC CGA TAC GGG GTA GAC TTG ATC GTG     1152
Leu Leu Leu Lys Glu Leu Tyr Asn Arg Tyr Gly Val Asp Leu Ile Val
        370                 375                 380

ACC GAG AAC GGT GTT TCA GAC AGC AGG GAT GCG TTG AGA CCG GCA TAC     1200
Thr Glu Asn Gly Val Ser Asp Ser Arg Asp Ala Leu Arg Pro Ala Tyr
385                 390                 395                 400

CTG GTC TCG CAT GTT TAC AGC GTA TGG AAA GCC GCT AAC GAG GGC ATT     1248
Leu Val Ser His Val Tyr Ser Val Trp Lys Ala Ala Asn Glu Gly Ile
                405                 410                 415

CCC GTC AAA GGC TAC CTC CAC TGG AGC TTG ACA GAC AAT TAC GAG TGG     1296
Pro Val Lys Gly Tyr Leu His Trp Ser Leu Thr Asp Asn Tyr Glu Trp
                420                 425                 430

GCC CAG GGC TTC AGG CAG AAA TTC GGT TTA GTC ATG GTT GAC TTC AAA     1344
Ala Gln Gly Phe Arg Gln Lys Phe Gly Leu Val Met Val Asp Phe Lys
            435                 440                 445

ACT AAG AAA AGG TAT CTC CGC CCA AGC GCC CTA GTG TTC CGG GAG ATC     1392
Thr Lys Lys Arg Tyr Leu Arg Pro Ser Ala Leu Val Phe Arg Glu Ile
        450                 455                 460

GCA ACG CAT AAC GGA ATA CCG GAT GAG CTA CAG CAT CTT ACA CTG ATC     1440
Ala Thr His Asn Gly Ile Pro Asp Glu Leu Gln His Leu Thr Leu Ile
465                 470                 475                 480

CAG TAA                                                             1446
Gln
```

FIG. 1-2

OC1/4 GLYCOSIDASE - 33G/B
COMPLETE GENE SEQUENCE - 9/95

```
ATG ATA AGA AGG TCC GAT TTT CCA AAA GAT TTT ATC TTC GGA ACG GCT      48
Met Ile Arg Arg Ser Asp Phe Pro Lys Asp Phe Ile Phe Gly Thr Ala
 1               5                  10                  15

ACG GCA GCA TAC CAG ATT GAA GGT GCA GCA AAC GAA GAT GGC AGA GGG      96
Thr Ala Ala Tyr Gln Ile Glu Gly Ala Ala Asn Glu Asp Gly Arg Gly
                20                  25                  30

CCA TCA ATT TGG GAT GTC TTT TCA CAC ACG CCT GGC AAA ACC CTG AAC     144
Pro Ser Ile Trp Asp Val Phe Ser His Thr Pro Gly Lys Thr Leu Asn
            35                  40                  45

GGT GAC ACA GGA GAC GTT GCG TGT GAC CAT TAT CAC CGA TAC AAG GAA     192
Gly Asp Thr Gly Asp Val Ala Cys Asp His Tyr His Arg Tyr Lys Glu
        50                  55                  60

GAT ATC CAG CTG ATG AAA GAA ATA GGG TTA GAC GCT TAC AGG TTC TCT     240
Asp Ile Gln Leu Met Lys Glu Ile Gly Leu Asp Ala Tyr Arg Phe Ser
 65                 70                  75                  80

ATC TCC TGG CCC AGA ATT ATG CCA GAT GGG AAG AAC ATC AAC CAA AAG     288
Ile Ser Trp Pro Arg Ile Met Pro Asp Gly Lys Asn Ile Asn Gln Lys
                85                  90                  95

GGT GTG GAT TTC TAC AAC AGA CTC GTT GAT GAG CTT TTG AAG AAT GAT     336
Gly Val Asp Phe Tyr Asn Arg Leu Val Asp Glu Leu Leu Lys Asn Asp
               100                 105                 110

ATC ATA CCA TTC GTA ACA CTC TAT CAC TGG GAC TTA CCC TAC GCA CTT     384
Ile Ile Pro Phe Val Thr Leu Tyr His Trp Asp Leu Pro Tyr Ala Leu
           115                 120                 125

TAT GAA AAA GGT GGA TGG CTT AAC CCA GAT ATA GCG CTC TAT TTC AGA     432
Tyr Glu Lys Gly Gly Trp Leu Asn Pro Asp Ile Ala Leu Tyr Phe Arg
       130                 135                 140

GCA TAC GCA ACG TTT ATG TTC AAC GAA CTC GGT GAT CGT GTG AAA CAT     480
Ala Tyr Ala Thr Phe Met Phe Asn Glu Leu Gly Asp Arg Val Lys His
145                 150                 155                 160

TGG ATT ACA CTG AAC GAA CCA TGG TGT TCT TCT TTC TCG GGT TAT TAC     528
Trp Ile Thr Leu Asn Glu Pro Trp Cys Ser Ser Phe Ser Gly Tyr Tyr
                165                 170                 175

ACG GGA GAG CAT GCC CCG GGT CAT CAA AAT TTA CAA GAA GCG ATA ATC     576
Thr Gly Glu His Ala Pro Gly His Gln Asn Leu Gln Glu Ala Ile Ile
            180                 185                 190

GCG GCG CAC AAC CTG TTG AGG GAA CAT GGA CAT GCC GTC CAG GCG TCC     624
Ala Ala His Asn Leu Leu Arg Glu His Gly His Ala Val Gln Ala Ser
        195                 200                 205

AGA GAA GAA GTA AAA GAT GGG GAA GTT GGC TTA ACC AAC GTT GTG ATG     672
Arg Glu Glu Val Lys Asp Gly Glu Val Gly Leu Thr Asn Val Val Met
    210                 215                 220
```

FIG. 2-1

```
AAA ATA GAA CCG GGC GAT GCA AAA CCC GAA AGT TTC TTG GTC GCA AGT    720
Lys Ile Glu Pro Gly Asp Ala Lys Pro Glu Ser Phe Leu Val Ala Ser
225                 230                 235                 240

CTT GTT GAT AAG TTC GTT AAT GCA TGG TCC CAT GAC CCT GTT GTT TTC    768
Leu Val Asp Lys Phe Val Asn Ala Trp Ser His Asp Pro Val Val Phe
                245                 250                 255

GGA AAA TAT CCC GAA GAA GCA GTT GCA CTT TAT ACG GAA AAA GGG TTG    816
Gly Lys Tyr Pro Glu Glu Ala Val Ala Leu Tyr Thr Glu Lys Gly Leu
            260                 265                 270

CAA GTT CTC GAT AGC GAT ATG AAT ATT ATT TCG ACT CCT ATA GAC TTC    864
Gln Val Leu Asp Ser Asp Met Asn Ile Ile Ser Thr Pro Ile Asp Phe
        275                 280                 285

TTT GGT GTG AAT TAT TAC ACA AGA ACA CTT GTT GTT TTT GAT ATG AAC    912
Phe Gly Val Asn Tyr Tyr Thr Arg Thr Leu Val Val Phe Asp Met Asn
    290                 295                 300

AAT CCT CTT GGA TTT TCG TAT GTT CAG GGA GAC CTT CCC AAA ACG GAG    960
Asn Pro Leu Gly Phe Ser Tyr Val Gln Gly Asp Leu Pro Lys Thr Glu
305                 310                 315                 320

ATG GGA TGG GAA ATC TAC CCG CAG GGA TTA TTT GAT ATG CTG GTC TAT   1008
Met Gly Trp Glu Ile Tyr Pro Gln Gly Leu Phe Asp Met Leu Val Tyr
                325                 330                 335

CTG AAG GAA AGA TAT AAA CTA CCA CTT TAT ATC ACA GAG AAC GGG ATG   1056
Leu Lys Glu Arg Tyr Lys Leu Pro Leu Tyr Ile Thr Glu Asn Gly Met
                340                 345                 350

GCT GGA CCT GAT AAA TTG GAA AAC GGA AGA GTT CAT GAT AAT TAC CGA   1104
Ala Gly Pro Asp Lys Leu Glu Asn Gly Arg Val His Asp Asn Tyr Arg
            355                 360                 365

ATT GAA TAT TTG GAA AAG CAC TTT GAA AAA GCA CTT GAA GCA ATC AAT   1152
Ile Glu Tyr Leu Glu Lys His Phe Glu Lys Ala Leu Glu Ala Ile Asn
        370                 375                 380

GCA GAT GTT GAT TTG AAA GGT TAC TTC ATT TGG TCT TTG ATG GAT AAC   1200
Ala Asp Val Asp Leu Lys Gly Tyr Phe Ile Trp Ser Leu Met Asp Asn
385                 390                 395                 400

TTC GAA TGG GCG TGC GGA TAC TCC AAA CGT TTC GGT ATA ATC TAC GTA   1248
Phe Glu Trp Ala Cys Gly Tyr Ser Lys Arg Phe Gly Ile Ile Tyr Val
                405                 410                 415

GAT TAC AAT ACC CCA AAA AGG ATA TTG AAA GAT TCA GCG ATG TGG TTG   1296
Asp Tyr Asn Thr Pro Lys Arg Ile Leu Lys Asp Ser Ala Met Trp Leu
                420                 425                 430

AAG GAA TTT CTA AAA TCT TAA                                       1317
Lys Glu Phe Leu Lys Ser
        43
```

FIG. 2-2

STAPHYLOTHERMUS MARINUS GLYCOSIDASE – 12G
COMPLETE GENE SEQUENCE 9/95

```
TTG ATA AGG TTT CCT GAT TAT TTC TTG TTT GGA ACA GCT ACA TCA TCG        48
Leu Ile Arg Phe Pro Asp Tyr Phe Leu Phe Gly Thr Ala Thr Ser Ser
 1               5                  10                  15

CAC CAG ATC GAG GGT AAT AAC ATA TTT AAT GAT TGG TGG GAG TGG GAG        96
His Gln Ile Glu Gly Asn Asn Ile Phe Asn Asp Trp Trp Glu Trp Glu
 20              25                  30

ACT AAA GGC AGG ATT AAG GTG AGA TCG GGT AAG GCA TGT AAT CAT TGG       144
Thr Lys Gly Arg Ile Lys Val Arg Ser Gly Lys Ala Cys Asn His Trp
         35                  40                  45

GAA CTC TAT AAA GAA GAC ATA GAG CTT ATG GCT GAG CTG GGA TAT AAT       192
Glu Leu Tyr Lys Glu Asp Ile Glu Leu Met Ala Glu Leu Gly Tyr Asn
         50                  55                  60

GCT TAT AGG TTC TCC ATA GAG TGG AGT AGA ATA TTT CCC AGA AAA GAT       240
Ala Tyr Arg Phe Ser Ile Glu Trp Ser Arg Ile Phe Pro Arg Lys Asp
 65              70                  75                  80

CAT ATA GAT TAT GAG TCG CTT AAT AAG TAT AAG GAA ATA GTT AAT CTA       288
His Ile Asp Tyr Glu Ser Leu Asn Lys Tyr Lys Glu Ile Val Asn Leu
         85                  90                  95

CTT AGA AAA TAC GGG ATA GAA CCT GTA ATC ACT CTT CAC CAC TTC ACA       336
Leu Arg Lys Tyr Gly Ile Glu Pro Val Ile Thr Leu His His Phe Thr
         100                 105                 110

AAC CCG CAA TGG TTT ATG AAA ATT GGT GGA TGG ACT AGG GAA GAG AAC       384
Asn Pro Gln Trp Phe Met Lys Ile Gly Gly Trp Thr Arg Glu Glu Asn
         115                 120                 125

ATA AAA TAT TTT ATA AAA TAT GTA GAA CTT ATA GCT TCC GAG ATA AAA       432
Ile Lys Tyr Phe Ile Lys Tyr Val Glu Leu Ile Ala Ser Glu Ile Lys
         130                 135                 140

GAC GTG AAA ATA TGG ATC ACT ATT AAT GAA CCA ATA ATA TAT GTT TTA       480
Asp Val Lys Ile Trp Ile Thr Ile Asn Glu Pro Ile Ile Tyr Val Leu
 145                 150                 155                 160

CAA GGA TAT ATT TCC GGC GAA TGG CCA CCT GGA ATT AAA AAT TTA AAA       528
Gln Gly Tyr Ile Ser Gly Glu Trp Pro Pro Gly Ile Lys Asn Leu Lys
                 165                 170                 175

ATA GCT GAT CAA GTA ACT AAG AAT CTT TTA AAA GCA CAT AAT GAA GCC       576
Ile Ala Asp Gln Val Thr Lys Asn Leu Leu Lys Ala His Asn Glu Ala
                 180                 185                 190

TAT AAT ATA CTT CAT AAA CAC GGT ATT GTA GGC ATA GCT AAA AAC ATG       624
Tyr Asn Ile Leu His Lys His Gly Ile Val Gly Ile Ala Lys Asn Met
                 195                 200                 205

ATA GCA TTT AAA CCA GGA TCT AAT AGA GGA AAA GAC ATT AAT ATT TAT       672
Ile Ala Phe Lys Pro Gly Ser Asn Arg Gly Lys Asp Ile Asn Ile Tyr
         210                 215                 220
```

FIG. 3-1

```
CAT AAA GTC GAT AAA GCA TTC AAC TGG GGA TTT CTC AAC GGA ATA TTA      720
His Lys Val Asp Lys Ala Phe Asn Trp Gly Phe Leu Asn Gly Ile Leu
225                 230                 235                 240

AGG GGA GAA CTA GAA ACT CTC CGT GGA AAA TAC CGA GTT GAG CCC GGA      768
Arg Gly Glu Leu Glu Thr Leu Arg Gly Lys Tyr Arg Val Glu Pro Gly
                245                 250                 255

AAT ATT GAT TTC ATA GGC ATA AAC TAT TAT TCA TCA TAT ATT GTA AAA      816
Asn Ile Asp Phe Ile Gly Ile Asn Tyr Tyr Ser Ser Tyr Ile Val Lys
            260                 265                 270

TAT ACT TGG AAT CCT TTT AAA CTA CAT ATT AAA GTC GAA CCA TTA GAT      864
Tyr Thr Trp Asn Pro Phe Lys Leu His Ile Lys Val Glu Pro Leu Asp
        275                 280                 285

ACA GGT CTA TGG ACA ACT ATG GGT TAC TGC ATA TAT CCT AGA GGA ATA      912
Thr Gly Leu Trp Thr Thr Met Gly Tyr Cys Ile Tyr Pro Arg Gly Ile
    290                 295                 300

TAT GAA GTT GTA ATG AAA ACT CAT GAG AAA TAC GGC AAA GAA ATA ATC      960
Tyr Glu Val Val Met Lys Thr His Glu Lys Tyr Gly Lys Glu Ile Ile
305                 310                 315                 320

ATT ACA GAG AAC GGT GTT GCA GTA GAA AAT GAT GAA TTA AGG ATT TTA     1008
Ile Thr Glu Asn Gly Val Ala Val Glu Asn Asp Glu Leu Arg Ile Leu
                325                 330                 335

TCC ATT ATC AGG CAC TTA CAA TAC TTA TAT AAA GCC ATG AAT GAA GGA     1056
Ser Ile Ile Arg His Leu Gln Tyr Leu Tyr Lys Ala Met Asn Glu Gly
            340                 345                 350

GCA AAG GTG AAA GGA TAT TTC TAC TGG AGC TTC ATG GAT AAT TTT GAG     1104
Ala Lys Val Lys Gly Tyr Phe Tyr Trp Ser Phe Met Asp Asn Phe Glu
        355                 360                 365

TGG GAT AAA GGA TTT AAC CAA AGG TTC GGA CTA GTA GAA GTT GAT TAT     1152
Trp Asp Lys Gly Phe Asn Gln Arg Phe Gly Leu Val Glu Val Asp Tyr
    370                 375                 380

AAG ACT TTT GAG AGA AAA CCT AGA AAA AGC GCA TAT GTA TAT AGT CAA     1200
Lys Thr Phe Glu Arg Lys Pro Arg Lys Ser Ala Tyr Val Tyr Ser Gln
385                 390                 395                 400

ATA GCA CGT ACC AAG ACT ATA AGT GAT GAA TAC CTA GAA AAA TAT GGA     1248
Ile Ala Arg Thr Lys Thr Ile Ser Asp Glu Tyr Leu Glu Lys Tyr Gly
                405                 410                 415

TTA AAG AAC CTC GAA TAA                                             1266
Leu Lys Asn Leu Glu
                420
```

FIG. 3-2

THERMOCOCCUS 9N2 GLYCOSIDASE – 31B/G
COMPLETE GENE SEQUENCE 9/95

```
ATG CTA CCA GAA GGC TTT CTC TGG GGC GTG TCC CAG TCC GGC TTT CAG     48
Met Leu Pro Glu Gly Phe Leu Trp Gly Val Ser Gln Ser Gly Phe Gln
 1           5                  10                  15

TTC GAG ATG GGC GAC AAG CTC AGG AGG AAC ATT GAT CCG AAC ACA GAC     96
Phe Glu Met Gly Asp Lys Leu Arg Arg Asn Ile Asp Pro Asn Thr Asp
             20                  25                  30

TGG TGG AAG TGG GTC AGG GAT CCC TTC AAC ATA AAG AGG GAA CTC GTC    144
Trp Trp Lys Trp Val Arg Asp Pro Phe Asn Ile Lys Arg Glu Leu Val
         35                  40                  45

AGC GGC GAC CTG CCC GAG GAG GGG ATA AAC AAC TAC GAA CTT TAC GAG    192
Ser Gly Asp Leu Pro Glu Glu Gly Ile Asn Asn Tyr Glu Leu Tyr Glu
     50                  55                  60

AAG GAT CAC CGC CTC GCC AGA GAC CTC GGT CTG AAC GTT TAC AGG ATT    240
Lys Asp His Arg Leu Ala Arg Asp Leu Gly Leu Asn Val Tyr Arg Ile
 65                  70                  75                  80

GGA ATA GAG TGG AGC AGG ATC TTT CCC TGG CCA ACG TGG TTT GTG GAG    288
Gly Ile Glu Trp Ser Arg Ile Phe Pro Trp Pro Thr Trp Phe Val Glu
             85                  90                  95

GTT GAC GTT GAG CGG GAC AGC TAC GGA CTC GTG AAG GAC GTC AAA ATC    336
Val Asp Val Glu Arg Asp Ser Tyr Gly Leu Val Lys Asp Val Lys Ile
            100                 105                 110

GAT AAA GAC ACG CTC GAA GAG CTC GAC GAG ATA GCG AAT CAT CAG GAG    384
Asp Lys Asp Thr Leu Glu Glu Leu Asp Glu Ile Ala Asn His Gln Glu
        115                 120                 125

ATA GCC TAC TAC CGC CGC GTT ATA GAG CAC CTC AGG GAG CTG GGC TTC    432
Ile Ala Tyr Tyr Arg Arg Val Ile Glu His Leu Arg Glu Leu Gly Phe
    130                 135                 140

AAG GTC ATC GTG AAC CTC AAC CAC TTC ACG CTC CCC CTC TGG CTT CAC    480
Lys Val Ile Val Asn Leu Asn His Phe Thr Leu Pro Leu Trp Leu His
145                 150                 155                 160

GAT CCG ATA ATC GCG AGG GAG AAG GCC CTC ACC AAC GGT AGG ATT GGC    528
Asp Pro Ile Ile Ala Arg Glu Lys Ala Leu Thr Asn Gly Arg Ile Gly
            165                 170                 175

TGG GTC GGG CAG GAG AGC GTG GTG GAG TTC GCC AAG TAC GCG GCG TAC    576
Trp Val Gly Gln Glu Ser Val Val Glu Phe Ala Lys Tyr Ala Ala Tyr
            180                 185                 190

ATC GCG AAC GCA CTC GGG GAC CTC GTT GAT ATG TGG AGC ACC TTC AAC    624
Ile Ala Asn Ala Leu Gly Asp Leu Val Asp Met Trp Ser Thr Phe Asn
        195                 200                 205

GAG CCG ATG GTC GTT GTG GAG CTC GGT TAC CTC GCG CCC TAC TCC GGC    672
Glu Pro Met Val Val Val Glu Leu Gly Tyr Leu Ala Pro Tyr Ser Gly
    210                 215                 220

TTT CCG CCG GGG GTT ATG AAC CCC GAG GCG GCA AAG CTG GCA ATC CTC    720
Phe Pro Pro Gly Val Met Asn Pro Glu Ala Ala Lys Leu Ala Ile Leu
225                 230                 235                 240

AAC ATG ATA AAC GCC CAC GCA CTG GCC TAC AAG ATG ATA AAG AAG TTC    768
Asn Met Ile Asn Ala His Ala Leu Ala Tyr Lys Met Ile Lys Lys Phe
            245                 250                 255
```

FIG. 4-1

```
GAC AGG GTA AAG GCC GAT AAG GAT TCC CGC TCC GAG GCC GAG GTC GGG       816
Asp Arg Val Lys Ala Asp Lys Asp Ser Arg Ser Glu Ala Glu Val Gly
            260                 265                 270

ATA ATC TAC AAC AAC ATA GGC GTT GCC TAT CCA TAC GAC TCC AAC GAC       864
Ile Ile Tyr Asn Asn Ile Gly Val Ala Tyr Pro Tyr Asp Ser Asn Asp
            275                 280                 285

CCA AAG GAC GTG AAA GCT GCA GAA AAC GAC AAC TAC TTC CAC AGC GGG       912
Pro Lys Asp Val Lys Ala Ala Glu Asn Asp Asn Tyr Phe His Ser Gly
295                 300

CTC TTC TTC GAC GCA ATC CAC AAG GGC AAG CTC AAC ATC GAG TTC GAC       960
Leu Phe Phe Asp Ala Ile His Lys Gly Lys Leu Asn Ile Glu Phe Asp
305                 310                 315                 320

GGT GAG ACC TTC GTC AAA GTT CGG CAT CTC AGG GGG AAC GAC TGG ATA      1008
Gly Glu Thr Phe Val Lys Val Arg His Leu Arg Gly Asn Asp Trp Ile
            325                 330                 335

GGC GTT AAC TAC TAC ACG AGA GAA GTC GTC AGG TAT TCG GAG CCC AAG      1056
Gly Val Asn Tyr Tyr Thr Arg Glu Val Val Arg Tyr Ser Glu Pro Lys
            340                 345                 350

TTC CCG AGC ATA CCC CTG ATA TCC TTC CGG GGA GTT CAC AAC TAC GGC      1104
Phe Pro Ser Ile Pro Leu Ile Ser Phe Arg Gly Val His Asn Tyr Gly
            355                 360                 365

TAC GCC TGC AGG CCC GGG AGT TCT TCC GCC GAC GGA AGG CCC GTA AGC      1152
Tyr Ala Cys Arg Pro Gly Ser Ser Ser Ala Asp Gly Arg Pro Val Ser
            370                 375                 380

GAC ATC GGC TGG GAG ATC TAT CCG GAG GGG ATC TAC GAC TCG ATA AGA      1200
Asp Ile Gly Trp Glu Ile Tyr Pro Glu Gly Ile Tyr Asp Ser Ile Arg
385                 390                 395                 400

GAG GCC AAC AAA TAC GGG GTC CCG GTT TAC GTC ACC GAA AAC GGA ATA      1248
Glu Ala Asn Lys Tyr Gly Val Pro Val Tyr Val Thr Glu Asn Gly Ile
            405                 410                 415

GCC GAT TCA ACT GAC ACC CTG CGG CCG TAC TAC CTC GCG AGC CAT GTA      1296
Ala Asp Ser Thr Asp Thr Leu Arg Pro Tyr Tyr Leu Ala Ser His Val
            420                 425                 430

GCG AAG ATT GAG GAG GCG TAC GAG GCG GGT TAC GAC GTC AGG GGC TAC      1344
Ala Lys Ile Glu Glu Ala Tyr Glu Ala Gly Tyr Asp Val Arg Gly Tyr
            435                 440                 445

CTC TAC TGG GCG CTG ACC GAC AAC TAC GAG TGG GCC CTC GGT TTC AGG      1392
Leu Tyr Trp Ala Leu Thr Asp Asn Tyr Glu Trp Ala Leu Gly Phe Arg
            450                 455                 460

ATG AGG TTC GGC CTC TAT AAA GTG GAT CTC ATA ACC AAG GAG AGA ACA      1440
Met Arg Phe Gly Leu Tyr Lys Val Asp Leu Ile Thr Lys Glu Arg Thr
465                 470                 475                 480

CCG CGG GAG GAA AGC GTA AAG GTT TAT AGG GGC ATC GTG GAG AAC AAC      1488
Pro Arg Glu Glu Ser Val Lys Val Tyr Arg Gly Ile Val Glu Asn Asn
            485                 490                 495

GGA GTG AGC AAG GAA ATC CGG GAG AAG TTC GGA CTT GGG TGA              1530
Gly Val Ser Lys Glu Ile Arg Glu Lys Phe Gly Leu Gly
            500                 505
```

FIG. 4-2

```
ATG GAA AGG ATC GAT GAA ATT CTC TCT CAG TTA ACT ACA GAG GAA AAG         48
Met Glu Arg Ile Asp Glu Ile Leu Ser Gln Leu Thr Thr Glu Glu Lys
 1               5                  10                  15

GTG AAG CTC GTT GTG GGG GTT GGT CTT CCA GGA CTT TTT GGG AAC CCA         96
Val Lys Leu Val Val Gly Val Gly Leu Pro Gly Leu Phe Gly Asn Pro
             20                  25                  30

CAT TCC AGA GTG GCG GGT GCG GCT GGA GAA ACA CAT CCC GTT CCA AGA        144
His Ser Arg Val Ala Gly Ala Ala Gly Glu Thr His Pro Val Pro Arg
         35                  40                  45

CTT GGA ATT CCT GCG TTT GTC CTG GCA GAT GGT CCC GCA GGA CTC AGA        192
Leu Gly Ile Pro Ala Phe Val Leu Ala Asp Gly Pro Ala Gly Leu Arg
     50                  55                  60

ATA AAT CCC ACA AGG GAA AAC GAT GAA AAC ACT TAC TAC ACG ACG GCA        240
Ile Asn Pro Thr Arg Glu Asn Asp Glu Asn Thr Tyr Tyr Thr Thr Ala
 65                  70                  75                  80

TTT CCC GTT GAA ATC ATG CTC GCT TCT ACC TGG AAC AGA GAC CTT CTG        288
Phe Pro Val Glu Ile Met Leu Ala Ser Thr Trp Asn Arg Asp Leu Leu
                 85                  90                  95

GAA GAA GTG GGA AAA GCC ATG GGA GAA GAA GTT AGG GAA TAC GGT GTC        336
Glu Glu Val Gly Lys Ala Met Gly Glu Glu Val Arg Glu Tyr Gly Val
             100                 105                 110

GAT GTG CTT CTT GCA CCT GCG ATG AAC ATT CAC AGA AAC CCT CTT TGT        384
Asp Val Leu Leu Ala Pro Ala Met Asn Ile His Arg Asn Pro Leu Cys
         115                 120                 125

GGA AGG AAT TTC GAG TAC TAC TCA GAA GAT CCT GTC CTT TCC GGT GAA        432
Gly Arg Asn Phe Glu Tyr Tyr Ser Glu Asp Pro Val Leu Ser Gly Glu
     130                 135                 140

ATG GCT TCA GCC TTT GTC AAG GGA GTT CAA TCT CAA GGG GTG GGA GCC        480
Met Ala Ser Ala Phe Val Lys Gly Val Gln Ser Gln Gly Val Gly Ala
145                 150                 155                 160

TGC ATA AAA CAC TTT GTC GCG AAC AAC CAG GAA ACG AAC AGG ATG GTA        528
Cys Ile Lys His Phe Val Ala Asn Asn Gln Glu Thr Asn Arg Met Val
                 165                 170                 175

GTG GAC ACG ATC GTG TCC CAG CGA GCC CTC AGA GAA ATA TAT CTG AAA        576
Val Asp Thr Ile Val Ser Gln Arg Ala Leu Arg Glu Ile Tyr Leu Lys
             180                 185                 190

GGT TTT GAA ATT GCT GTC AAG AAA GCA AGA CCC TGG ACC GTG ATG AGC        624
Gly Phe Glu Ile Ala Val Lys Lys Ala Arg Pro Trp Thr Val Met Ser
         195                 200                 205

GCT TAC AAC AAA CTG AAT GGA AAA TAC TGT TCA CAG AAC GAA TGG CTT        672
Ala Tyr Asn Lys Leu Asn Gly Lys Tyr Cys Ser Gln Asn Glu Trp Leu
     210                 215                 220

TTG AAG AAG GTT CTC AGG GAA GAA TGG GGA TTT GGC GGT TTC GTG ATG        720
Leu Lys Lys Val Leu Arg Glu Glu Trp Gly Phe Gly Gly Phe Val Met
225                 230                 235                 240

AGC GAC TGG TAC GCG GGA GAC AAC CCT GTA GAA CAG CTC AAG GCC GGA        768
Ser Asp Trp Tyr Ala Gly Asp Asn Pro Val Glu Gln Leu Lys Ala Gly
                 245                 250                 255
```

FIG. 5-1

```
AAC GAT ATG ATC ATG CCT GGG AAA GCG TAT CAG GTG AAC ACA GAA AGA      816
Asn Asp Met Ile Met Pro Gly Lys Ala Tyr Gln Val Asn Thr Glu Arg
            260                 265                 270

AGA GAT GAA ATA GAA GAA ATC ATG GAG GCG TTG AAG GAG GGA AAA TTG      864
Arg Asp Glu Ile Glu Glu Ile Met Glu Ala Leu Lys Glu Gly Lys Leu
            275                 280                 285

AGT GAG GAG GTT CTC GAT GAG TGT GTG AGA AAC ATT CTC AAA GTT CTT      912
Ser Glu Glu Val Leu Asp Glu Cys Val Arg Asn Ile Leu Lys Val Leu
    290                 295                 300

GTG AAC GCG CCT TCC TTC AAA GGG TAC AGG TAC TCA AAC AAG CCG GAT      960
Val Asn Ala Pro Ser Phe Lys Gly Tyr Arg Tyr Ser Asn Lys Pro Asp
305                 310                 315                 320

CTC GAA TCT CAC GCG GAA GTC GCC TAC GAA GCA GGT GCG GAG GGT GTT     1008
Leu Glu Ser His Ala Glu Val Ala Tyr Glu Ala Gly Ala Glu Gly Val
                325                 330                 335

GTC CTT CTT GAG AAC AAC GGT GTT CTT CCG TTC GAT GAA AAT ACC CAT     1056
Val Leu Leu Glu Asn Asn Gly Val Leu Pro Phe Asp Glu Asn Thr His
            340                 345                 350

GTC GCC GTC TTT GGC ACC GGT CAA ATC GAA ACA ATA AAG GGA GGA ACG     1104
Val Ala Val Phe Gly Thr Gly Gln Ile Glu Thr Ile Lys Gly Gly Thr
            355                 360                 365

GGA AGT GGA GAC ACC CAT CCG AGA TAC ACG ATC TCT ATC CTT GAA GGC     1152
Gly Ser Gly Asp Thr His Pro Arg Tyr Thr Ile Ser Ile Leu Glu Gly
    370                 375                 380

ATA AAA GAA AGA AAC ATG AAG TTC GAC GAA GAA CTC GCT TCC ACT TAT     1200
Ile Lys Glu Arg Asn Met Lys Phe Asp Glu Glu Leu Ala Ser Thr Tyr
385                 390                 395                 400

GAG GAG TAC ATA AAA AAG ATG AGA GAA ACA GAG GAA TAT AAA CCC AGA     1248
Glu Glu Tyr Ile Lys Lys Met Arg Glu Thr Glu Glu Tyr Lys Pro Arg
                405                 410                 415

ACC GAC TCT TGG GGA ACG GTC ATA AAA CCG AAA CTC CCA GAG AAT TTC     1296
Thr Asp Ser Trp Gly Thr Val Ile Lys Pro Lys Leu Pro Glu Asn Phe
            420                 425                 430

CTC TCA GAA AAA GAG ATA AAG AAA CCT CCA AAG AAA AAC GAT GTT GCA     1344
Leu Ser Glu Lys Glu Ile Lys Lys Pro Pro Lys Lys Asn Asp Val Ala
            435                 440                 445

GTT GTT GTG ATC AGT AGG ATC TCC GGT GAG GGA TAC GAC AGA AAG CCG     1392
Val Val Val Ile Ser Arg Ile Ser Gly Glu Gly Tyr Asp Arg Lys Pro
            450                 455                 460

GTG AAA GGT GAC TTC TAC CTC TCC GAT GAC GAG CTG GAA CTC ATA AAA     1440
Val Lys Gly Asp Phe Tyr Leu Ser Asp Asp Glu Leu Glu Leu Ile Lys
465                 470                 475                 480

ACC GTC TCG AAA GAA TTC CAC GAT CAG GGT AAG AAA GTT GTG GTT CTT     1488
Thr Val Ser Lys Glu Phe His Asp Gln Gly Lys Lys Val Val Val Leu
            485                 490                 495

CTG AAC ATC GGA AGT CCC ATC GAA GTC GCA AGC TGG AGA GAC CTT GTG    1536
 Leu Asn Ile Gly Ser Pro Ile Glu Val Ala Ser Trp Arg Asp Leu Val
                 500                 505                 510
```

FIG. 5-2

```
GAT GGA ATT CTT CTC GTC TGG CAG GCG GGA CAG GAG ATG GGA AGA ATA    1584
Asp Gly Ile Leu Leu Val Trp Gln Ala Gly Gln Glu Met Gly Arg Ile
        515                 520                 525

GTG GCC GAT GTT CTT GTG GGA AAG ATT AAT CCC TCC GGA AAA CTT CCA    1632
Val Ala Asp Val Leu Val Gly Lys Ile Asn Pro Ser Gly Lys Leu Pro
    530                 535                 540

ACG ACC TTC CCG AAG GAT TAC TCG GAC GTT CCA TCC TGG ACG TTC CCA    1680
Thr Thr Phe Pro Lys Asp Tyr Ser Asp Val Pro Ser Trp Thr Phe Pro
545                 550                 555                 560

GGA GAG CCA AAG GAC AAT CCG CAA AGA GTG GTG TAC GAG GAA GAC ATC    1728
Gly Glu Pro Lys Asp Asn Pro Gln Arg Val Val Tyr Glu Glu Asp Ile
                565                 570                 575

TAC GTG GGA TAC AGG TAC TAC GAC ACC TTC GGT GTG GAA CCT GCC TAC    1776
Tyr Val Gly Tyr Arg Tyr Tyr Asp Thr Phe Gly Val Glu Pro Ala Tyr
            580                 585                 590

GAA TTC GGC TAC GGC CTC TCT TAC ACA AAG TTT GAA TAC AAA GAT TTA    1824
Glu Phe Gly Tyr Gly Leu Ser Tyr Thr Lys Phe Glu Tyr Lys Asp Leu
        595                 600                 605

AAA ATC GCT ATC GAC GGT GAG ACG CTC AGA GTG TCG TAC ACG ATC ACA    1872
Lys Ile Ala Ile Asp Gly Glu Thr Leu Arg Val Ser Tyr Thr Ile Thr
    610                 615                 620

AAC ACT GGG GAC AGA GCT GGA AAG GAA GTC TCA CAG GTC TAC ATC AAA    1920
Asn Thr Gly Asp Arg Ala Gly Lys Glu Val Ser Gln Val Tyr Ile Lys
625                 630                 635                 640

GCT CCA AAA GGA AAA ATA GAC AAA CCC TTC CAG GAG CTG AAA GCG TTT    1968
Ala Pro Lys Gly Lys Ile Asp Lys Pro Phe Gln Glu Leu Lys Ala Phe
                645                 650                 655

CAC AAA ACA AAA CTT TTG AAC CCG GGT GAA TCA GAA GAA ATC TCC TTG    2016
His Lys Thr Lys Leu Leu Asn Pro Gly Glu Ser Glu Glu Ile Ser Leu
            660                 665                 670

GAA ATT CCT CTC AGA GAT CTT GCG AGT TTC GAT GGG AAA GAA TGG GTT    2064
Glu Ile Pro Leu Arg Asp Leu Ala Ser Phe Asp Gly Lys Glu Trp Val
        675                 680                 685

GTC GAG TCA GGA GAA TAC GAG GTC AGG GTC GGT GCA TCT TCG AGG GAT    2112
Val Glu Ser Gly Glu Tyr Glu Val Arg Val Gly Ala Ser Ser Arg Asp
    690                 695                 700

ATA AGG TTG AGA GAT ATT TTT CTG GTT GAG GGA GAG AAG AGA TTC AAA    2160
Ile Arg Leu Arg Asp Ile Phe Leu Val Glu Gly Glu Lys Arg Phe Lys
705                 710                 715                 720

CCA TGA                                                            2166
Pro
```

FIG. 5-3

THERMOCOCCUS AEDII 12RA GLYCOSIDASE (18B/G)
COMPLETE GENE SEQUENCE – 9/95

```
ATG ATC CAC TGC CCG GTT AAA GGG ATT ATA TCT GAG GCT CGC GGC ATA      48
Met Ile His Cys Pro Val Lys Gly Ile Ile Ser Glu Ala Arg Gly Ile
 1            5               10                  15

ACC ATC ACA ATA GAT TTA AGT TTT CAA GGC CAA ATA AAT AAT TTG GTG      96
Thr Ile Thr Ile Asp Leu Ser Phe Gln Gly Gln Ile Asn Asn Leu Val
             20                  25                  30

AAT GCT ATG ATT GTC TTT CCG GAG TTC TTC CTC TTT GGA ACC GCC ACA     144
Asn Ala Met Ile Val Phe Pro Glu Phe Phe Leu Phe Gly Thr Ala Thr
         35                  40                  45

TCT TCT CAT CAG ATC GAG GGA GAT AAT AAA TGG AAC GAC TGG TGG TAT     192
Ser Ser His Gln Ile Glu Gly Asp Asn Lys Trp Asn Asp Trp Trp Tyr
     50                  55                  60

TAT GAG GAG ATA GGT AAG CTC CCC TAC AAA TCC GGT AAA GCC TGC AAT     240
Tyr Glu Glu Ile Gly Lys Leu Pro Tyr Lys Ser Gly Lys Ala Cys Asn
 65              70                  75                  80

CAC TGG GAG CTT TAC AGG GAA GAT ATA GAG CTA ATG GCA CAG CTC GGC     288
His Trp Glu Leu Tyr Arg Glu Asp Ile Glu Leu Met Ala Gln Leu Gly
                 85                  90                  95

TAC AAT GCC TAC CGC TTT TCG ATA GAG TGG AGC CGT CTC TTC CCG GAA     336
Tyr Asn Ala Tyr Arg Phe Ser Ile Glu Trp Ser Arg Leu Phe Pro Glu
             100                 105                 110

GAG GGC AAA TTC AAT GAA GAA GCC TTC AAC CGC TAC CGT GAA ATA ATT     384
Glu Gly Lys Phe Asn Glu Glu Ala Phe Asn Arg Tyr Arg Glu Ile Ile
         115                 120                 125

GAA ATC CTC CTT GAG AAG GGG ATT ACT CCA AAC GTT ACA CTG CAC CAC     432
Glu Ile Leu Leu Glu Lys Gly Ile Thr Pro Asn Val Thr Leu His His
     130                 135                 140

TTC ACA TCA CCG CTG TGG TTC ATG CGG AAG GGA GGC TTT TTG AAG GAA     480
Phe Thr Ser Pro Leu Trp Phe Met Arg Lys Gly Gly Phe Leu Lys Glu
145                 150                 155                 160

GAA AAC CTC AAG TAC TGG GAG CAG TAC GTT GAT AAA GCC GCG GAG CTC     528
Glu Asn Leu Lys Tyr Trp Glu Gln Tyr Val Asp Lys Ala Ala Glu Leu
                 165                 170                 175

CTC AAG GGA GTC AAG CTT GTA GCT ACA TTC AAC GAG CCG ATG GTC TAT     576
Leu Lys Gly Val Lys Leu Val Ala Thr Phe Asn Glu Pro Met Val Tyr
             180                 185                 190

GTT ATG ATG GGC TAC CTC ACA GCC TAC TGG CCG CCC TTC ATC AAG AGT     624
Val Met Met Gly Tyr Leu Thr Ala Tyr Trp Pro Pro Phe Ile Lys Ser
         195                 200                 205

CCC TTT AAA GCC TTT AAA GTT GCC GCA AAC CTC CTT AAG GCC CAT GCA     672
Pro Phe Lys Ala Phe Lys Val Ala Ala Asn Leu Leu Lys Ala His Ala
210                 215                 220
```

FIG. 6-1

```
ATG GCA TAT GAT ATC CTC CAT GGT AAC TTT GAT GTG GGG ATA GTT AAA    720
Met Ala Tyr Asp Ile Leu His Gly Asn Phe Asp Val Gly Ile Val Lys
225                 230                 235                 240

AAC ATC CCC ATA ATG CTC CCT GCA AGC AAC AGA GAG AAA GAC GTA GAA    768
Asn Ile Pro Ile Met Leu Pro Ala Ser Asn Arg Glu Lys Asp Val Glu
                245                 250                 255

GCT GCC CAA AAG GCG GAT AAC CTC TTT AAC TGG AAC TTC CTT GAT GCA    816
Ala Ala Gln Lys Ala Asp Asn Leu Phe Asn Trp Asn Phe Leu Asp Ala
            260                 265                 270

ATA TGG AGC GGA AAA TAT AAA GGA GCT TTT GGA ACT TAC AAA ACT CCA    864
Ile Trp Ser Gly Lys Tyr Lys Gly Ala Phe Gly Thr Tyr Lys Thr Pro
        275                 280                 285

GAA AGC GAT GCA GAC TTC ATA GGG ATA AAC TAC TAC ACA GCC AGC GAG    912
Glu Ser Asp Ala Asp Phe Ile Gly Ile Asn Tyr Tyr Thr Ala Ser Glu
    290                 295                 300

GTA AGG CAT AGC TGG AAT CCG CTA AAG TTT TTC TTC GAT GCC AAG CTT    960
Val Arg His Ser Trp Asn Pro Leu Lys Phe Phe Phe Asp Ala Lys Leu
305                 310                 315                 320

GCA GAC TTA AGC GAG AGA AAA ACA GAT ATG GGT TGG AGT GTC TAT CCA   1008
Ala Asp Leu Ser Glu Arg Lys Thr Asp Met Gly Trp Ser Val Tyr Pro
                325                 330                 335

AAG GGC ATA TAC GAA GCT ATA GCA AAG GTT TCA CAC TAC GGA AAG CCA   1056
Lys Gly Ile Tyr Glu Ala Ile Ala Lys Val Ser His Tyr Gly Lys Pro
            340                 345                 350

ATG TAC ATC ACG GAA AAC GGG ATA GCT ACC TTA GAC GAT GAG TGG AGG   1104
Met Tyr Ile Thr Glu Asn Gly Ile Ala Thr Leu Asp Asp Glu Trp Arg
        355                 360                 365

ATA GAG TTT ATC ATC CAG CAC CTC CAG TAC GTT CAC AAA GCC TTA AAC   1152
Ile Glu Phe Ile Ile Gln His Leu Gln Tyr Val His Lys Ala Leu Asn
    370                 375                 380

GAT GGC TTT GAC TTG AGA GGC TAC TTC TAT TGG TCT TTT ATG GAT AAC   1200
Asp Gly Phe Asp Leu Arg Gly Tyr Phe Tyr Trp Ser Phe Met Asp Asn
385                 390                 395                 400

TTC GAG TGG GCT GAG GGT TTT AGA CCA CGC TTT GGG CTG GTC GAG GTG   1248
Phe Glu Trp Ala Glu Gly Phe Arg Pro Arg Phe Gly Leu Val Glu Val
                405                 410                 415

GAC TAC ACG ACC TTC AAG AGG AGA CCG AGA AAG AGT GCT TAC ATA TAT   1296
Asp Tyr Thr Thr Phe Lys Arg Arg Pro Arg Lys Ser Ala Tyr Ile Tyr
            420                 425                 430

GGA GAA ATT GCA AGG GAA AAG AAA ATA AAA GAC GAA CTG CTG GCA AAG   1344
Gly Glu Ile Ala Arg Glu Lys Lys Ile Lys Asp Glu Leu Leu Ala Lys
        435                 440                 445

TAT GGG CTT CCG GAG CTA TGA                                       1365
Tyr Gly Leu Pro Glu Leu
    450
```

FIG. 6-2

THERMOCOCCUS CHITONPHAGUS GLYCOSIDASE – 22G
COMPLETE SEQUENCE – 9/95

```
TTG CTT CCA GAG AAC TTT CTC TGG GGA GTT TCA CAG TCC GGA TTC CAG    48
Leu Leu Pro Glu Asn Phe Leu Trp Gly Val Ser Gln Ser Gly Phe Gln
 1           5                   10                  15
TTT GAA ATG GGG GAC AGA CTG AGG AGG CAC ATT GAT CCA AAC ACA GAT    96
Phe Glu Met Gly Asp Arg Leu Arg Arg His Ile Asp Pro Asn Thr Asp
             20                  25                  30
TGG TGG TAC TGG GTA AGA GAT GAA TAT AAT ATC AAA AAA GGA CTA GTA   144
Trp Trp Tyr Trp Val Arg Asp Glu Tyr Asn Ile Lys Lys Gly Leu Val
         35                  40                  45
AGT GGG GAT CTT CCC GAA GAC GGT ATA AAT TCA TAT GAA TTA TAT GAG   192
Ser Gly Asp Leu Pro Glu Asp Gly Ile Asn Ser Tyr Glu Leu Tyr Glu
     50                  55                  60
AGA GAC CAA GAA ATT GCA AAG GAT TTA GGG CTC AAC ACA TAT AGG ATC   240
Arg Asp Gln Glu Ile Ala Lys Asp Leu Gly Leu Asn Thr Tyr Arg Ile
 65                  70                  75                  80
GGA ATT GAA TGG AGC AGA GTA TTT CCA TGG CCA ACG ACT TTT GTC GAC   288
Gly Ile Glu Trp Ser Arg Val Phe Pro Trp Pro Thr Thr Phe Val Asp
                 85                  90                  95
GTG GAG TAT GAA ATT GAT GAG TCT TAC GGG TTG GTA AAG GAT GTG AAG   336
Val Glu Tyr Glu Ile Asp Glu Ser Tyr Gly Leu Val Lys Asp Val Lys
             100                 105                 110
ATT TCT AAA GAC GCA TTA GAA AAA CTT GAT GAA ATC GCT AAC CAA AGG   384
Ile Ser Lys Asp Ala Leu Glu Lys Leu Asp Glu Ile Ala Asn Gln Arg
         115                 120                 125
GAA ATA ATA TAT TAT AGG AAC CTA ATA AAT TCC CTA AGA AAG AGG GGT   432
Glu Ile Ile Tyr Tyr Arg Asn Leu Ile Asn Ser Leu Arg Lys Arg Gly
     130                 135                 140
TTT AAG GTA ATA CTA AAC CTA AAT CAT TTT ACC CTC CCA ATA TGG CTT   480
Phe Lys Val Ile Leu Asn Leu Asn His Phe Thr Leu Pro Ile Trp Leu
145                 150                 155                 160
CAT GAT CCT ATC GAA TCT AGA GAA AAA GCC CTG ACC AAT AAG AGA AAC   528
His Asp Pro Ile Glu Ser Arg Glu Lys Ala Leu Thr Asn Lys Arg Asn
                 165                 170                 175
GGA TGG GTA AGC GAA AGG AGT GTT ATA GAG TTT GCA AAA TTT GCC GCG   576
Gly Trp Val Ser Glu Arg Ser Val Ile Glu Phe Ala Lys Phe Ala Ala
             180                 185                 190
TAT TTA GCA TAT AAA TTC GGA GAC ATA GTA GAC ATG TGG AGC ACA TTT   624
Tyr Leu Ala Tyr Lys Phe Gly Asp Ile Val Asp Met Trp Ser Thr Phe
         195                 200                 205
AAT GAA CCT ATG GTG GTC GCC GAG TTG GGG TAT TTA GCC CCA TAC TCA   672
Asn Glu Pro Met Val Val Ala Glu Leu Gly Tyr Leu Ala Pro Tyr Ser
     210                 215                 220
GGA TTC CCC CCG GGA GTC ATG AAT CCA GAA GCA GCA AAG TTA GTT ATG   720
Gly Phe Pro Pro Gly Val Met Asn Pro Glu Ala Ala Lys Leu Val Met
225                 230                 235                 240
CTA CAT ATG ATA AAC GCC CAT GCT TTA GCA TAT AGG ATG ATA AAG AAA   768
Leu His Met Ile Asn Ala His Ala Leu Ala Tyr Arg Met Ile Lys Lys
                 245                 250                 255
```

FIG. 7-1

```
TTT GAC AGA AAA AAA GCT GAT CCA GAA TCA AAA GAA CCA GCT GAA ATA    816
Phe Asp Arg Lys Lys Ala Asp Pro Glu Ser Lys Glu Pro Ala Glu Ile
        260                 265                 270

GGA ATT ATA TAC AAT AAC ATC GGC GTC ACA TAT CCG TTT AAT CCG AAA    864
Gly Ile Ile Tyr Asn Asn Ile Gly Val Thr Tyr Pro Phe Asn Pro Lys
        275                 280                 285

GAC TCA AAG GAT CTA CAA GCA TCC GAT AAT GCC AAT TTC TTC CAC AGT    912
Asp Ser Lys Asp Leu Gln Ala Ser Asp Asn Ala Asn Phe Phe His Ser
        290                 295                 300

GG CTA TTC TTA ACG GCT ATC CAC AGG GGA AAA TTA AAT ATC GAA TTT     960
Gly Leu Phe Leu Thr Ala Ile His Arg Gly Lys Leu Asn Ile Glu Phe
305             310                 315                 320

GAC GGA GAG ACA TTT GTT TAC CTT CCA TAT TTA AAG GGC AAT GAT TGG   1008
Asp Gly Glu Thr Phe Val Tyr Leu Pro Tyr Leu Lys Gly Asn Asp Trp
            325                 330                 335

CTG GGA GTG AAT TAT TAT ACA AGA GAA GTC GTT AAA TAC CAA GAT CCC   1056
Leu Gly Val Asn Tyr Tyr Thr Arg Glu Val Val Lys Tyr Gln Asp Pro
            340                 345                 350

ATG TTT CCA AGT ATC CCT CTC ATA AGC TTC AAG GGC GTT CCA GAT TAT   1104
Met Phe Pro Ser Ile Pro Leu Ile Ser Phe Lys Gly Val Pro Asp Tyr
            355                 360                 365

GGA TAC GGA TGT AGA CCA GGA ACG ACG TCA AAG GAC GGT AAT CCT GTT   1152
Gly Tyr Gly Cys Arg Pro Gly Thr Thr Ser Lys Asp Gly Asn Pro Val
        370                 375                 380

AGT GAC ATT GGA TGG GAG GTA TAT CCC AAA GGC ATG TAC GAC TCT ATA   1200
Ser Asp Ile Gly Trp Glu Val Tyr Pro Lys Gly Met Tyr Asp Ser Ile
385             390                 395                 400

GTA GCT GCC AAT GAA TAT GGA GTT CCT GTA TAC GTA ACA GAA AAC GGA   1248
Val Ala Ala Asn Glu Tyr Gly Val Pro Val Tyr Val Thr Glu Asn Gly
                405                 410                 415

ATA GCA GAT TCA AAA GAT GTA TTA AGG CCC TAT TAC ATC GCA TCT CAC   1296
Ile Ala Asp Ser Lys Asp Val Leu Arg Pro Tyr Tyr Ile Ala Ser His
            420                 425                 430

ATT GAA GCC ATG GAA GAG GCT TAC GAA AAT GGT TAT GAC GTG AGA GGA   1344
Ile Glu Ala Met Glu Glu Ala Tyr Glu Asn Gly Tyr Asp Val Arg Gly
            435                 440                 445

TAC TTA CAC TGG GCA TTA ACC GAT AAT TAC GAA TGG GCC TTA GGG TTC   1392
Tyr Leu His Trp Ala Leu Thr Asp Asn Tyr Glu Trp Ala Leu Gly Phe
        450                 455                 460

AGA ATG AGG TTT GGC TTG TAC GAA GTA AAC TTG ATA ACC AAA GAG AGA   1440
Arg Met Arg Phe Gly Leu Tyr Glu Val Asn Leu Ile Thr Lys Glu Arg
465             470                 475                 480

AAA CCC AGG AAA AAG AGT GTA AGA GTA TTC AGA GAG ATA GTT ATT AAT   1488
Lys Pro Arg Lys Lys Ser Val Arg Val Phe Arg Glu Ile Val Ile Asn
                485                 490                 495

AAT GGG CTA ACA AGC AAC ATC AGG AAA GAG ATC TTA GAG GAG GGG TAG   1536
Asn Gly Leu Thr Ser Asn Ile Arg Lys Glu Ile Leu Glu Glu Gly
            500                 505                 510
```

FIG. 7-2

PYROCOCCUS FURIOSUS GLYCOSIDASE – 7G1
COMPLETE GENE SEQUENCE – 10/95

```
ATG TTC CCT GAA AAG TTC CTT TGG GGT GTG GCA CAA TCG GGT TTT CAG    48
Met Phe Pro Glu Lys Phe Leu Trp Gly Val Ala Gln Ser Gly Phe Gln
 1               5                  10                  15

TTT GAA ATG GGG GAT AAA CTC AGG AGG AAT ATT GAC ACT AAC ACT GAT    96
Phe Glu Met Gly Asp Lys Leu Arg Arg Asn Ile Asp Thr Asn Thr Asp
             20                  25                  30

TGG TGG CAC TGG GTA AGG GAT AAG ACA AAT ATA GAG AAA GGC CTC GTT   144
Trp Trp His Trp Val Arg Asp Lys Thr Asn Ile Glu Lys Gly Leu Val
         35                  40                  45

AGT GGA GAT CTT CCC GAG GAG GGG ATT AAC AAT TAC GAG CTT TAT GAG   192
Ser Gly Asp Leu Pro Glu Glu Gly Ile Asn Asn Tyr Glu Leu Tyr Glu
     50                  55                  60

AAG GAC CAT GAG ATT GCA AGA AAG CTG GGT CTT AAT GCT TAC AGA ATA   240
Lys Asp His Glu Ile Ala Arg Lys Leu Gly Leu Asn Ala Tyr Arg Ile
 65                  70                  75                  80

GGC ATA GAG TGG AGC AGA ATA TTC CCA TGG CCA ACG ACA TTT ATT GAT   288
Gly Ile Glu Trp Ser Arg Ile Phe Pro Trp Pro Thr Thr Phe Ile Asp
             85                  90                  95

GTT GAT TAT AGC TAT AAT GAA TCA TAT AAC CTT ATA GAA GAT GTA AAG   336
Val Asp Tyr Ser Tyr Asn Glu Ser Tyr Asn Leu Ile Glu Asp Val Lys
            100                 105                 110

ATC ACC AAG GAC ACT TTG GAG GAG TTA GAT GAG ATC GCC AAC AAG AGG   384
Ile Thr Lys Asp Thr Leu Glu Glu Leu Asp Glu Ile Ala Asn Lys Arg
        115                 120                 125

GAG GTG GCC TAC TAT AGG TCA GTC ATA AAC AGC CTG AGG AGC AAG GGG   432
Glu Val Ala Tyr Tyr Arg Ser Val Ile Asn Ser Leu Arg Ser Lys Gly
    130                 135                 140

TTT AAG GTT ATA GTT AAT CTA AAT CAC TTC ACC CTT CCA TAT TGG TTG   480
Phe Lys Val Ile Val Asn Leu Asn His Phe Thr Leu Pro Tyr Trp Leu
145                 150                 155                 160

CAT GAT CCC ATT GAG GCT AGG GAG AGG GCG TTA ACT AAT AAG AGG AAC   528
His Asp Pro Ile Glu Ala Arg Glu Arg Ala Leu Thr Asn Lys Arg Asn
                165                 170                 175

GGC TGG GTT AAC CCA AGA ACA GTT ATA GAG TTT GCA AAG TAT GCC GCT   576
Gly Trp Val Asn Pro Arg Thr Val Ile Glu Phe Ala Lys Tyr Ala Ala
            180                 185                 190

TAC ATA GCC TAT AAG TTT GGA GAT ATA GTG GAT ATG TGG AGC ACG TTT   624
Tyr Ile Ala Tyr Lys Phe Gly Asp Ile Val Asp Met Trp Ser Thr Phe
        195                 200                 205

AAT GAG CCT ATG GTG GTT GTT GAG CTT GGC TAC CTA GCC CCC TAC TCT   672
Asn Glu Pro Met Val Val Val Glu Leu Gly Tyr Leu Ala Pro Tyr Ser
    210                 215                 220

GGC TTC CCT CCA GGG GTT CTA AAT CCA GAG GCC GCA AAG CTG GCG ATA   720
Gly Phe Pro Pro Gly Val Leu Asn Pro Glu Ala Ala Lys Leu Ala Ile
225                 230                 235                 240

CTT CAC ATG ATA AAT GCA CAT GCT TTA GCT TAT AGG CAG ATA AAG AAG   768
Leu His Met Ile Asn Ala His Ala Leu Ala Tyr Arg Gln Ile Lys Lys
                245                 250                 255
```

FIG. 8-1

```
TTT GAC ACT GAG AAA GCT GAT AAG GAT TCT AAA GAG CCT GCA GAA GTT    816
Phe Asp Thr Glu Lys Ala Asp Lys Asp Ser Lys Glu Pro Ala Glu Val
            260                 265                 270

GGT ATA ATT TAC AAC AAC ATT GGA GTT GCT TAT CCC AAG GAT CCG AAC    864
Gly Ile Ile Tyr Asn Asn Ile Gly Val Ala Tyr Pro Lys Asp Pro Asn
            275                 280                 285

GAT TCC AAG GAT GTT AAG GCA GCA GAA AAC GAC AAC TTC TTC CAC TCA    912
Asp Ser Lys Asp Val Lys Ala Ala Glu Asn Asp Asn Phe Phe His Ser
            290                 295                 300

GGG CTG TTC TTC GAG GCC ATA CAC AAA GGA AAA CTT AAT ATA GAG TTT    960
Gly Leu Phe Phe Glu Ala Ile His Lys Gly Lys Leu Asn Ile Glu Phe
305                 310                 315                 320

GAC GGT GAA ACG TTT ATA GAT GCC CCC TAT CTA AAG GGC AAT GAC TGG   1008
Asp Gly Glu Thr Phe Ile Asp Ala Pro Tyr Leu Lys Gly Asn Asp Trp
            325                 330                 335

ATA GGG GTT AAT TAC TAC ACA AGG GAA GTA GTT ACG TAT CAG GAA CCA   1056
Ile Gly Val Asn Tyr Tyr Thr Arg Glu Val Val Thr Tyr Gln Glu Pro
            340                 345                 350

ATG TTT CCT TCA ATC CCG CTG ATC ACC TTT AAG GGA GTT CAA GGA TAT   1104
Met Phe Pro Ser Ile Pro Leu Ile Thr Phe Lys Gly Val Gln Gly Tyr
            355                 360                 365

GGC TAT GCC TGC AGA CCT GGA ACT CTG TCA AAG GAT GAC AGA CCC GTC   1152
Gly Tyr Ala Cys Arg Pro Gly Thr Leu Ser Lys Asp Asp Arg Pro Val
            370                 375                 380

AGC GAC ATA GGA TGG GAA CTC TAT CCA GAG GGG ATG TAC GAT TCA ATA   1200
Ser Asp Ile Gly Trp Glu Leu Tyr Pro Glu Gly Met Tyr Asp Ser Ile
385                 390                 395                 400

GTT GAA GCT CAC AAG TAC GGC GTT CCA GTT TAC GTG ACG GAG AAC GGA   1248
Val Glu Ala His Lys Tyr Gly Val Pro Val Tyr Val Thr Glu Asn Gly
            405                 410                 415

ATA GCG GAT TCA AAG GAC ATC CTA AGA CCT TAC TAC ATA GCG AGC CAC   1296
Ile Ala Asp Ser Lys Asp Ile Leu Arg Pro Tyr Tyr Ile Ala Ser His
            420                 425                 430

ATA AAG ATG ATA GAG AAG GCC TTT GAG GAT GGG TAT GAA GTT AAG GGC   1344
Ile Lys Met Ile Glu Lys Ala Phe Glu Asp Gly Tyr Glu Val Lys Gly
            435                 440                 445

TAC TTC CAC TGG GCA TTA ACT GAC AAC TTC GAG TGG GCT CTC GGG TTT   1392
Tyr Phe His Trp Ala Leu Thr Asp Asn Phe Glu Trp Ala Leu Gly Phe
            450                 455                 460

AGA ATG CGC TTT GGC CTC TAC GAA GTC AAC CTA ATT ACA AAG GAG AGA   1440
Arg Met Arg Phe Gly Leu Tyr Glu Val Asn Leu Ile Thr Lys Glu Arg
465                 470                 475                 480

ATT CCC AGG GAG AAG AGC GTG TCG ATA TTC AGA GAG ATA GTA GCC AAT   1488
Ile Pro Arg Glu Lys Ser Val Ser Ile Phe Arg Glu Ile Val Ala Asn
            485                 490                 495

AAT GGT GTT ACG AAA AAG ATT GAA GAG GAA TTG CTG AGG GGA TGA        1533
Asn Gly Val Thr Lys Lys Ile Glu Glu Glu Leu Leu Arg Gly
            500                 505                 510
```

FIG. 8-2

BANKIA GOULDI ENDOGLUCANASE (37GF1)

```
ATG AGA ATA CGT TTA GCG ACG CTC GCG CTC TGC GCA GCG CTG AGC CCA    48
Met Arg Ile Arg Leu Ala Thr Leu Ala Leu Cys Ala Ala Leu Ser Pro
 1               5                  10                  15

GTC ACC TTT GCA GAT AAT GTA ACC GTA CAA ATC GAC GCC GAC GGC GGT    96
Val Thr Phe Ala Asp Asn Val Thr Val Gln Ile Asp Ala Asp Gly Gly
             20                  25                  30

AAA AAA CTC ATC AGC CGA GCC CTT TAC GGC ATG AAT AAC TCC AAC GCA   144
Lys Lys Leu Ile Ser Arg Ala Leu Tyr Gly Met Asn Asn Ser Asn Ala
         35                  40                  45

GAA AGC CTT ACC GAT ACT GAC TGG CAG CGT TTT CGC GAT GCA GGT GTG   192
Glu Ser Leu Thr Asp Thr Asp Trp Gln Arg Phe Arg Asp Ala Gly Val
     50                  55                  60

CGC ATG CTG CGG GAA AAT GGC GGC AAC AAC AGC ACC AAA TAT AAC TGG   240
Arg Met Leu Arg Glu Asn Gly Gly Asn Asn Ser Thr Lys Tyr Asn Trp
 65                  70                  75                  80

CAA CTG CAC CTG AGC AGT CAT CCG GAT TGG TAC AAC AAT GTC TAC GCC   288
Gln Leu His Leu Ser Ser His Pro Asp Trp Tyr Asn Asn Val Tyr Ala
             85                  90                  95

GGC AAC AAC AAC TGG GAC AAC CGG GTA GCC CTG ATT CAG GAA AAC CTG   336
Gly Asn Asn Asn Trp Asp Asn Arg Val Ala Leu Ile Gln Glu Asn Leu
        100                 105                 110

CCC GGC GCC GAC ACC ATG TGG GCA TTC CAG CTC ATC GGT AAG GTC GCG   384
Pro Gly Ala Asp Thr Met Trp Ala Phe Gln Leu Ile Gly Lys Val Ala
        115                 120                 125

GCG ACT TCT GCC TAC AAC TTT AAC GAT TGG GAA TTC AAC CAG TCG CAA   432
Ala Thr Ser Ala Tyr Asn Phe Asn Asp Trp Glu Phe Asn Gln Ser Gln
    130                 135                 140

TGG TGG ACC GGC GTC GCT CAG AAT CTC GCT GGC GGC GGT GAA CCC AAT   480
Trp Trp Thr Gly Val Ala Gln Asn Leu Ala Gly Gly Gly Glu Pro Asn
145                 150                 155                 160

CTG GAC GGC GGC GGC GAA GCC CTG GTT GAA GGA GAC CCC AAT CTC TAC   528
Leu Asp Gly Gly Gly Glu Ala Leu Val Glu Gly Asp Pro Asn Leu Tyr
                165                 170                 175

CTC ATG GAT TGG TCG CCA GCC GAC ACT GTG GGT ATT CTC GAC CAC TGG   576
Leu Met Asp Trp Ser Pro Ala Asp Thr Val Gly Ile Leu Asp His Trp
            180                 185                 190

TTT GGC GTA AAC GGG CTG GGC GTG CGG CGT GGC AAA GCC AAA TAC TGG   624
Phe Gly Val Asn Gly Leu Gly Val Arg Arg Gly Lys Ala Lys Tyr Trp
        195                 200                 205

AGT ATG GAT AAC GAG CCC GGC ATC TGG GTT GGC ACC CAC GAC GAT GTA   672
Ser Met Asp Asn Glu Pro Gly Ile Trp Val Gly Thr His Asp Asp Val
    210                 215                 220
```

FIG. 9-1

BANKIA GOULDI ENDOGLUCANASE (37GF1)(CONTINUED)

```
GTG AAA GAA CAA ACG CCG GTA GAA GAT TTC CTG CAC ACC TAT TTC GAA    720
Val Lys Glu Gln Thr Pro Val Glu Asp Phe Leu His Thr Tyr Phe Glu
225                 230                 235                 240

ACC GCC AAA AAA GCC CGC GCC AAA TTT CCC GGT ATT AAA ATC ACC GGT    768
Thr Ala Lys Lys Ala Arg Ala Lys Phe Pro Gly Ile Lys Ile Thr Gly
                245                 250                 255

CCG GTG CCC GCT AAT GAG TGG CAG TGG TAT GCC TGG GGC GGT TTC TCG    816
Pro Val Pro Ala Asn Glu Trp Gln Trp Tyr Ala Trp Gly Gly Phe Ser
                    260                 265                 270

GTA CCC CAG GAA CAA GGG TTT ATG AGC TGG ATG GAG TAT TTC ATC AAG    864
Val Pro Gln Glu Gln Gly Phe Met Ser Trp Met Glu Tyr Phe Ile Lys
            275                 280                 285

CGG GTG TCT GAA GAG CAA CGC GCA AGT GGT GTT CGC CTC CTC GAT GTA    912
Arg Val Ser Glu Glu Gln Arg Ala Ser Gly Val Arg Leu Leu Asp Val
        290                 295                 300

CTC GAT CTG CAC TAC TAC CCC GGC GCT TAC AAT GCG GAA GAT ATC GTG    960
Leu Asp Leu His Tyr Tyr Pro Gly Ala Tyr Asn Ala Glu Asp Ile Val
305                 310                 315                 320

CAA TTA CAT CGC ACG TTC TTC GAC CGC GAC TTT GTT TCA CTG GAT GCC   1008
Gln Leu His Arg Thr Phe Phe Asp Arg Asp Phe Val Ser Leu Asp Ala
                325                 330                 335

AAC GGG GTG AAA ATG GTA GAA GGT GGC TGG GAT GAC AGC ATC AAC AAG   1056
Asn Gly Val Lys Met Val Glu Gly Gly Trp Asp Asp Ser Ile Asn Lys
                    340                 345                 350

GAA TAT ATT TTC GGG CGA GTG AAC GAT TGG CTC GAG GAA TAT ATG GGG   1104
Glu Tyr Ile Phe Gly Arg Val Asn Asp Trp Leu Glu Glu Tyr Met Gly
            355                 360                 365

CCA GAC CAT GGT GTA ACC CTG GGC TTA ACC GAA ATG TGC GTG CGC AAT   1152
Pro Asp His Gly Val Thr Leu Gly Leu Thr Glu Met Cys Val Arg Asn
        370                 375                 380

GTG AAT CCG ATG ACT ACC GCC ATC TGG TAT GCC TCC ATG CTC GGC ACC   1200
Val Asn Pro Met Thr Thr Ala Ile Trp Tyr Ala Ser Met Leu Gly Thr
385                 390                 395                 400

TTC GCG GAT AAC GGC GTC GAA ATA TTC ACC CCA TGG TGC TGG AAC ACC   1248
Phe Ala Asp Asn Gly Val Glu Ile Phe Thr Pro Trp Cys Trp Asn Thr
                405                 410                 415

GGA ATG TGG GAA ACA CTC CAC CTC TTC AGC CGC TAC AAC AAA CCT TAT   1296
Gly Met Trp Glu Thr Leu His Leu Phe Ser Arg Tyr Asn Lys Pro Tyr
                    420                 425                 430

CGG GTC GCC TCC AGC TCC AGT CTT GAA GAG TTT GTC AGC GCC TAC AGC   1344
Arg Val Ala Ser Ser Ser Ser Leu Glu Glu Phe Val Ser Ala Tyr Ser
            435                 440                 445

TCC ATT AAC GAA GCA GAA GAC GCC ATG ACG GTA CTT CTG GTG AAT CGT   1392
Ser Ile Asn Glu Ala Glu Asp Ala Met Thr Val Leu Leu Val Asn Arg
        450                 455                 460
```

FIG. 9-2

BANKIA GOULDI ENDOGLUCANASE (37GF1)(CONTINUED)

```
TCC ACT AGC GAG ACC CAC ACC GCC ACT GTC GCT ATC GAC GAT TTC CCA    1440
Ser Thr Ser Glu Thr His Thr Ala Thr Val Ala Ile Asp Asp Phe Pro
465                 470                 475                 480

CTG GAT GGC CCC TAC CGC ACC CTG CGC TTA CAC AAC CTG CCG GGG GAG    1488
Leu Asp Gly Pro Tyr Arg Thr Leu Arg Leu His Asn Leu Pro Gly Glu
                485                 490                 495

GAA ACC TTC GTA TCT CAC CGA GAC AAC GCC CTG GAA AAA GGT ACA GTG    1536
Glu Thr Phe Val Ser His Arg Asp Asn Ala Leu Glu Lys Gly Thr Val
            500                 505                 510

CGC GCC AGC GAC AAT ACG GTA ACA CTG GAG TTG CCC CCT CTG TCC GTT    1584
Arg Ala Ser Asp Asn Thr Val Thr Leu Glu Leu Pro Pro Leu Ser Val
        515                 520                 525

ACT GCA ATA TTG CTC AAG GCC CGG CCC TAA                            1614
Thr Ala Ile Leu Leu Lys Ala Arg Pro
    530                 535
```

FIG. 9-3

THERMOTOGA MARITIMA ALPHA-GALACTOSIDASE
COMPLETE GENE SEQUENCE (1 OF 3)

```
GTG ATC TGT GTG GAA ATA TTC GGA AAG ACC TTC AGA GAG GGA AGA TTC       48
Val Ile Cys Val Glu Ile Phe Gly Lys Thr Phe Arg Glu Gly Arg Phe
 1               5                  10                  15

GTT CTC AAA GAG AAA AAC TTC ACA GTT GAG TTC GCG GTG GAG AAG ATA       96
Val Leu Lys Glu Lys Asn Phe Thr Val Glu Phe Ala Val Glu Lys Ile
             20                  25                  30

CAC CTT GGC TGG AAG ATC TCC GGC AGG GTG AAG GGA AGT CCG GGA AGG      144
His Leu Gly Trp Lys Ile Ser Gly Arg Val Lys Gly Ser Pro Gly Arg
         35                  40                  45

CTT GAG GTT CTT CGA ACG AAA GCA CCG GAA AAG GTA CTT GTG AAC AAC      192
Leu Glu Val Leu Arg Thr Lys Ala Pro Glu Lys Val Leu Val Asn Asn
     50                  55                  60

TGG CAG TCC TGG GGA CCG TGC AGG GTG GTC GAT GCC TTT TCT TTC AAA      240
Trp Gln Ser Trp Gly Pro Cys Arg Val Val Asp Ala Phe Ser Phe Lys
 65                  70                  75                  80

CCA CCT GAA ATA GAT CCG AAC TGG AGA TAC ACC GCT TCG GTG GTG CCC      288
Pro Pro Glu Ile Asp Pro Asn Trp Arg Tyr Thr Ala Ser Val Val Pro
                 85                  90                  95

GAT GTA CTT GAA AGG AAC CTC CAG AGC GAC TAT TTC GTG GCT GAA GAA      336
Asp Val Leu Glu Arg Asn Leu Gln Ser Asp Tyr Phe Val Ala Glu Glu
             100                 105                 110

GGA AAA GTG TAC GGT TTT CTG AGT TCG AAA ATC GCA CAT CCT TTC TTC      384
Gly Lys Val Tyr Gly Phe Leu Ser Ser Lys Ile Ala His Pro Phe Phe
         115                 120                 125

GCT GTG GAA GAT GGG GAA CTT GTG GCA TAC CTC GAA TAT TTC GAT GTC      432
Ala Val Glu Asp Gly Glu Leu Val Ala Tyr Leu Glu Tyr Phe Asp Val
     130                 135                 140

GAG TTC GAC GAC TTT GTT CCT CTT GAA CCT CTC GTT GTA CTC GAG GAT      480
Glu Phe Asp Asp Phe Val Pro Leu Glu Pro Leu Val Val Leu Glu Asp
145                 150                 155                 160

CCC AAC ACA CCC CTT CTT CTG GAG AAA TAC GCG GAA CTC GTC GGA ATG      528
Pro Asn Thr Pro Leu Leu Leu Glu Lys Tyr Ala Glu Leu Val Gly Met
                 165                 170                 175

GAA AAC AAC GCG AGA GTT CCA AAA CAC ACA CCC ACT GGA TGG TGC AGC      576
Glu Asn Asn Ala Arg Val Pro Lys His Thr Pro Thr Gly Trp Cys Ser
             180                 185                 190

TGG TAC CAT TAC TTC CTT GAT CTC ACC TGG GAA GAG ACC CTC AAG AAC      624
Trp Tyr His Tyr Phe Leu Asp Leu Thr Trp Glu Glu Thr Leu Lys Asn
         195                 200                 205

CTG AAG CTC GCG AAG AAT TTC CCG TTC GAG GTC TTC CAG ATA GAC GAC      672
Leu Lys Leu Ala Lys Asn Phe Pro Phe Glu Val Phe Gln Ile Asp Asp
     210                 215                 220
```

FIG. 10-1

THERMOTOGA MARITIMA ALPHA-GALACTOSIDASE
COMPLETE GENE SEQUENCE (2 OF 3)

```
GCC TAC GAA AAG GAC ATA GGT GAC TGG CTC GTG ACA AGA GGA GAC TTT    720
Ala Tyr Glu Lys Asp Ile Gly Asp Trp Leu Val Thr Arg Gly Asp Phe
225                 230                 235                 240

CCA TCG GTG GAA GAG ATG GCA AAA GTT ATA GCG GAA AAC GGT TTC ATC    768
Pro Ser Val Glu Glu Met Ala Lys Val Ile Ala Glu Asn Gly Phe Ile
                245                 250                 255

CCG GGC ATA TGG ACC GCC CCG TTC AGT GTT TCT GAA ACC TCG GAT GTA    816
Pro Gly Ile Trp Thr Ala Pro Phe Ser Val Ser Glu Thr Ser Asp Val
            260                 265                 270

TTC AAC GAA CAT CCG GAC TGG GTA GTG AAG GAA AAC GGA GAG CCG AAG    864
Phe Asn Glu His Pro Asp Trp Val Val Lys Glu Asn Gly Glu Pro Lys
        275                 280                 285

ATG GCT TAC AGA AAC TGG AAC AAA AAG ATA TAC GCC CTC GAT CTT TCG    912
Met Ala Tyr Arg Asn Trp Asn Lys Lys Ile Tyr Ala Leu Asp Leu Ser
    290                 295                 300

AAA GAT GAG GTT CTG AAC TGG CTT TTC GAT CTC TTC TCA TCT CTG AGA    960
Lys Asp Glu Val Leu Asn Trp Leu Phe Asp Leu Phe Ser Ser Leu Arg
305                 310                 315                 320

AAG ATG GGC TAC AGG TAC TTC AAG ATC GAC TTT CTC TTC GCG GGT GCC   1008
Lys Met Gly Tyr Arg Tyr Phe Lys Ile Asp Phe Leu Phe Ala Gly Ala
                325                 330                 335

GTT CCA GGA GAA AGA AAA AAG AAC ATA ACA CCA ATT CAG GCG TTC AGA   1056
Val Pro Gly Glu Arg Lys Lys Asn Ile Thr Pro Ile Gln Ala Phe Arg
            340                 345                 350

AAA GGG ATT GAG ACG ATC AGA AAA GCG GTG GGA GAA GAT TCT TTC ATC   1104
Lys Gly Ile Glu Thr Ile Arg Lys Ala Val Gly Glu Asp Ser Phe Ile
        355                 360                 365

CTC GGA TGC GGC TCT CCC CTT CTT CCC GCA GTG GGA TGC GTC GAC GGG   1152
Leu Gly Cys Gly Ser Pro Leu Leu Pro Ala Val Gly Cys Val Asp Gly
    370                 375                 380

ATG AGG ATA GGA CCT GAC ACT GCG CCG TTC TGG GGA GAA CAT ATA GAA   1200
Met Arg Ile Gly Pro Asp Thr Ala Pro Phe Trp Gly Glu His Ile Glu
385                 390                 395                 400

GAC AAC GGA GCT CCC GCT GCA AGA TGG GCG CTG AGA AAC GCC ATA ACG   1248
Asp Asn Gly Ala Pro Ala Ala Arg Trp Ala Leu Arg Asn Ala Ile Thr
                405                 410                 415

AGG TAC TTC ATG CAC GAC AGG TTC TGG CTG AAC GAC CCC GAC TGT CTG   1296
Arg Tyr Phe Met His Asp Arg Phe Trp Leu Asn Asp Pro Asp Cys Leu
            420                 425                 430
```

FIG. 10-2

THERMOTOGA MARITIMA ALPHA-GALACTOSIDASE
COMPLETE GENE SEQUENCE (3 OF 3)

```
ATA CTG AGA GAG GAG AAA ACG GAT CTC ACA CAG AAG GAA AAG GAG CTC    344
Ile Leu Arg Glu Glu Lys Thr Asp Leu Thr Gln Lys Glu Lys Glu Leu
        435                 440                 445

TAC TCG TAC ACG TGT GGA GTG CTC GAC AAC ATG ATC ATA GAA AGC GAT   1392
Tyr Ser Tyr Thr Cys Gly Val Leu Asp Asn Met Ile Ile Glu Ser Asp
        450                 455                 460

GAT CTC TCG CTC GTC AGA GAT CAT GGA AAA AAG GTT CTG AAA GAA ACG   1440
Asp Leu Ser Leu Val Arg Asp His Gly Lys Lys Val Leu Lys Glu Thr
465                 470                 475                 480

CTC GAA CTC CTC GGT GGA AGA CCA CGG GTT CAA AAC ATC ATG TCG GAG   1488
Leu Glu Leu Leu Gly Gly Arg Pro Arg Val Gln Asn Ile Met Ser Glu
                485                 490                 495

GAT CTG AGA TAC GAG ATC GTC TCG TCT GGC ACT CTC TCA GGA AAC GTC   1536
Asp Leu Arg Tyr Glu Ile Val Ser Ser Gly Thr Leu Ser Gly Asn Val
            500                 505                 510

AAG ATC GTG GTC GAT CTG AAC AGC AGA GAG TAC CAC CTG GAA AAA GAA   1584
Lys Ile Val Val Asp Leu Asn Ser Arg Glu Tyr His Leu Glu Lys Glu
        515                 520                 525

GGA AAG TCC TCC CTG AAA AAA AGA GTC GTC AAA AGA GAA GAC GGA AGA   1632
Gly Lys Ser Ser Leu Lys Lys Arg Val Val Lys Arg Glu Asp Gly Arg
    530                 535                 540

AAC TTC TAC TTC TAC GAA GAG GGT GAG AGA GAA TGA                   1668
Asn Phe Tyr Phe Tyr Glu Glu Gly Glu Arg Glu
                545                 550                 555
```

FIG. 10-3

THERMOTOGA MARITINA β - MANNANASE (6GP2)

```
ATG GGG ATT GGT GGC GAC GAC TCC TGG AGC CCG TCA GTA TCG GCG GAA     48
Met Gly Ile Gly Gly Asp Asp Ser Trp Ser Pro Ser Val Ser Ala Glu
 1           5               10                  15

TTC CTT TTA TTG ATC GTT GAG CTC TCT TTC GTT CTC TTT GCA AGT GAC     96
Phe Leu Leu Leu Ile Val Glu Leu Ser Phe Val Leu Phe Ala Ser Asp
             20              25                  30

GAG TTC GTG AAA GTG GAA AAC GGA AAA TTC GCT CTG AAC GGA AAA GAA    144
Glu Phe Val Lys Val Glu Asn Gly Lys Phe Ala Leu Asn Gly Lys Glu
         35                  40                  45

TTC AGA TTC ATT GGA AGC AAC AAC TAC TAC ATG CAC TAC AAG AGC AAC    192
Phe Arg Phe Ile Gly Ser Asn Asn Tyr Tyr Met His Tyr Lys Ser Asn
     50                  55                  60

GGA ATG ATA GAC AGT GTT CTG GAG AGT GCC AGA GAC ATG GGT ATA AAG    240
Gly Met Ile Asp Ser Val Leu Glu Ser Ala Arg Asp Met Gly Ile Lys
 65                  70                  75                  80

GTC CTC AGA ATC TGG GGT TTC CTC GAC GGG GAG AGT TAC TGC AGA GAC    288
Val Leu Arg Ile Trp Gly Phe Leu Asp Gly Glu Ser Tyr Cys Arg Asp
             85                  90                  95

AAG AAC ACC TAC ATG CAT CCT GAG CCC GGT GTT TTC GGG GTG CCA GAA    336
Lys Asn Thr Tyr Met His Pro Glu Pro Gly Val Phe Gly Val Pro Glu
            100                 105                 110

GGA ATA TCG AAC GCC CAG AGC GGT TTC GAA AGA CTC GAC TAC ACA GTT    384
Gly Ile Ser Asn Ala Gln Ser Gly Phe Glu Arg Leu Asp Tyr Thr Val
            115                 120                 125

GCG AAA GCG AAA GAA CTC GGT ATA AAA CTT GTC ATT GTT CTT GTG AAC    432
Ala Lys Ala Lys Glu Leu Gly Ile Lys Leu Val Ile Val Leu Val Asn
        130                 135                 140

AAC TGG GAC GAC TTC GGT GGA ATG AAC CAG TAC GTG AGG TGG TTT GGA    480
Asn Trp Asp Asp Phe Gly Gly Met Asn Gln Tyr Val Arg Trp Phe Gly
145                 150                 155                 160

GGA ACC CAT CAC GAC GAT TTC TAC AGA GAT GAG AAG ATC AAA GAA GAG    528
Gly Thr His His Asp Asp Phe Tyr Arg Asp Glu Lys Ile Lys Glu Glu
                165                 170                 175

TAC AAA AAG TAC GTC TCC TTT CTC GTA AAC CAT GTC AAT ACC TAC ACG    576
Tyr Lys Lys Tyr Val Ser Phe Leu Val Asn His Val Asn Thr Tyr Thr
            180                 185                 190

GGA GTT CCT TAC AGG GAA GAG CCC ACC ATC ATG GCC TGG GAG CTT GCA    624
Gly Val Pro Tyr Arg Glu Glu Pro Thr Ile Met Ala Trp Glu Leu Ala
            195                 200                 205

AAC GAA CCG CGC TGT GAG ACG GAC AAA TCG GGG AAC ACG CTC GTT GAG    672
Asn Glu Pro Arg Cys Glu Thr Asp Lys Ser Gly Asn Thr Leu Val Glu
        210                 215                 220
```

FIG. 11-1

THERMOTOGA MARITINA β - MANNANASE (CONTINUED) (6GP2)

```
TGG GTG AAG GAG ATG AGC TCC TAC ATA AAG AGT CTG GAT CCC AAC CAC      720
Trp Val Lys Glu Met Ser Ser Tyr Ile Lys Ser Leu Asp Pro Asn His
225             230                 235                 240

CTC GTG GCT GTG GGG GAC GAA GGA TTC TTC AGC AAC TAC GAA GGA TTC      768
Leu Val Ala Val Gly Asp Glu Gly Phe Phe Ser Asn Tyr Glu Gly Phe
                245                 250                 255

AAA CCT TAC GGT GGA GAA GCC GAG TGG GCC TAC AAC GGC TGG TCC GGT      816
Lys Pro Tyr Gly Gly Glu Ala Glu Trp Ala Tyr Asn Gly Trp Ser Gly
                260                 265                 270

GTT GAC TGG AAG AAG CTC CTT TCG ATA GAG ACG GTG GAC TTC GGC ACG      864
Val Asp Trp Lys Lys Leu Leu Ser Ile Glu Thr Val Asp Phe Gly Thr
            275                 280                 285

TTC CAC CTC TAT CCG TCC CAC TGG GGT GTC AGT CCA GAG AAC TAT GCC      912
Phe His Leu Tyr Pro Ser His Trp Gly Val Ser Pro Glu Asn Tyr Ala
        290                 295                 300

CAG TGG GGA GCG AAG TGG ATA GAA GAC CAC ATA AAG ATC GCA AAA GAG      960
Gln Trp Gly Ala Lys Trp Ile Glu Asp His Ile Lys Ile Ala Lys Glu
305                 310                 315                 320

ATC GGA AAA CCC GTT GTT CTG GAA GAA TAT GGA ATT CCA AAG AGT GCG     1008
Ile Gly Lys Pro Val Val Leu Glu Glu Tyr Gly Ile Pro Lys Ser Ala
                325                 330                 335

CCA GTT AAC AGA ACG GCC ATC TAC AGA CTC TGG AAC GAT CTG GTC TAC     1056
Pro Val Asn Arg Thr Ala Ile Tyr Arg Leu Trp Asn Asp Leu Val Tyr
                340                 345                 350

GAT CTC GGT GGA GAT GGA GCG ATG TTC TGG ATG CTC GCG GGA ATC GGG     1104
Asp Leu Gly Gly Asp Gly Ala Met Phe Trp Met Leu Ala Gly Ile Gly
            355                 360                 365

GAA GGT TCG GAC AGA GAC GAG AGA GGG TAC TAT CCG GAC TAC GAC GGT     1152
Glu Gly Ser Asp Arg Asp Glu Arg Gly Tyr Tyr Pro Asp Tyr Asp Gly
        370                 375                 380

TTC AGA ATA GTG AAC GAC GAC AGT CCA GAA GCG GAA CTG ATA AGA GAA     1200
Phe Arg Ile Val Asn Asp Asp Ser Pro Glu Ala Glu Leu Ile Arg Glu
385                 390                 395                 400

TAC GCG AAG CTG TTC AAC ACA GGT GAA GAC ATA AGA GAA GAC ACC TGC     1248
Tyr Ala Lys Leu Phe Asn Thr Gly Glu Asp Ile Arg Glu Asp Thr Cys
                405                 410                 415

TCT TTC ATC CTT CCA AAA GAC GGC ATG GAG ATC AAA AAG ACC GTG GAA     1296
Ser Phe Ile Leu Pro Lys Asp Gly Met Glu Ile Lys Lys Thr Val Glu
                420                 425                 430

GTG AGG GCT GGT GTT TTC GAC TAC AGC AAC ACG TTT GAA AAG TTG TCT     1344
Val Arg Ala Gly Val Phe Asp Tyr Ser Asn Thr Phe Glu Lys Leu Ser
            435                 440                 445
```

FIG. 11-2

THERMOTOGA MARITINA β - MANNANASE (CONTINUED) (6GP2)

```
GTC AAA GTC GAA GAT CTG GTT TTT GAA AAT GAG ATA GAG CAT CTC GGA    1392
Val Lys Val Glu Asp Leu Val Phe Glu Asn Glu Ile Glu His Leu Gly
    450                 455                 460

TAC GGA ATT TAC GGC TTT GAT CTC GAC ACA ACC CGG ATC CCG GAT GGA    1440
Tyr Gly Ile Tyr Gly Phe Asp Leu Asp Thr Thr Arg Ile Pro Asp Gly
465                 470                 475                 480

GAA CAT GAA ATG TTC CTT GAA GGC CAC TTT CAG GGA AAA ACG GTG AAA    1488
Glu His Glu Met Phe Leu Glu Gly His Phe Gln Gly Lys Thr Val Lys
                485                 490                 495

GAC TCT ATC AAA GCG AAA GTG GTG AAC GAA GCA CGG TAC GTG CTC GCA    1536
Asp Ser Ile Lys Ala Lys Val Val Asn Glu Ala Arg Tyr Val Leu Ala
            500                 505                 510

GAG GAA GTT GAT TTT TCC TCT CCA GAA GAG GTG AAA AAC TGG TGG AAC    1584
Glu Glu Val Asp Phe Ser Ser Pro Glu Glu Val Lys Asn Trp Trp Asn
        515                 520                 525

AGC GGA ACC TGG CAG GCA GAG TTC GGG TCA CCT GAC ATT GAA TGG AAC    1632
Ser Gly Thr Trp Gln Ala Glu Phe Gly Ser Pro Asp Ile Glu Trp Asn
    530                 535                 540

GGT GAG GTG GGA AAT GGA GCA CTG CAG CTG AAC GTG AAA CTG CCC GGA    1680
Gly Glu Val Gly Asn Gly Ala Leu Gln Leu Asn Val Lys Leu Pro Gly
545                 550                 555                 560

AAG AGC GAC TGG GAA GAA GTG AGA GTA GCA AGG AAG TTC GAA AGA CTC    1728
Lys Ser Asp Trp Glu Glu Val Arg Val Ala Arg Lys Phe Glu Arg Leu
                565                 570                 575

TCA GAA TGT GAG ATC CTC GAG TAC GAC ATC TAC ATT CCA AAC GTC GAG    1776
Ser Glu Cys Glu Ile Leu Glu Tyr Asp Ile Tyr Ile Pro Asn Val Glu
            580                 585                 590

GGA CTC AAG GGA AGG TTG AGG CCG TAC GCG GTT CTG AAC CCC GGC TGG    1824
Gly Leu Lys Gly Arg Leu Arg Pro Tyr Ala Val Leu Asn Pro Gly Trp
        595                 600                 605

GTG AAG ATA GGC CTC GAC ATG AAC AAC GCG AAC GTG GAA AGT GCG GAG    1872
Val Lys Ile Gly Leu Asp Met Asn Asn Ala Asn Val Glu Ser Ala Glu
    610                 615                 620

ATC ATC ACT TTC GGC GGA AAA GAG TAC AGA AGA TTC CAT GTA AGA ATT    1920
Ile Ile Thr Phe Gly Gly Lys Glu Tyr Arg Arg Phe His Val Arg Ile
625                 630                 635                 640

GAG TTC GAC AGA ACA GCG GGG GTG AAA GAA CTT CAC ATA GGA GTT GTC    1968
Glu Phe Asp Arg Thr Ala Gly Val Lys Glu Leu His Ile Gly Val Val
                645                 650                 655

GGT GAT CAT CTG AGG TAC GAT GGA CCG ATT TTC ATC GAT AAT GTG AGA    2016
Gly Asp His Leu Arg Tyr Asp Gly Pro Ile Phe Ile Asp Asn Val Arg
            660                 665                 670

CTT TAT AAA AGA ACA GGA GGT ATG TGA                                2043
Leu Tyr Lys Arg Thr Gly Gly Met
        675                 680
```

FIG. 11-3

AEPII 1a β-MANNOSIDASE (63GB1)

```
ATG CTA CCA GAA GAG TTC CTA TGG GGC GTT GGG CAG TCA GGC TTT CAG      48
Met Leu Pro Glu Glu Phe Leu Trp Gly Val Gly Gln Ser Gly Phe Gln
 1               5                  10                  15

TTC GAA ATG GGC GAC AAG CTC AGG AGG CAC ATC GAT CCA AAT ACC GAC      96
Phe Glu Met Gly Asp Lys Leu Arg Arg His Ile Asp Pro Asn Thr Asp
            20                  25                  30

TGG TGG AAG TGG GTT CGC GAT CCT TTC AAC ATA AAA AAG GAG CTT GTG     144
Trp Trp Lys Trp Val Arg Asp Pro Phe Asn Ile Lys Lys Glu Leu Val
         35                  40                  45

AGT GGG GAC CTT CCC GAG GAC GGC ATC AAC AAC TAC GAA CTT TTT GAA     192
Ser Gly Asp Leu Pro Glu Asp Gly Ile Asn Asn Tyr Glu Leu Phe Glu
     50                  55                  60

AAC GAT CAC AAG CTC GCT AAA GGC CTT GGA CTC AAC GCA TAC AGG ATT     240
Asn Asp His Lys Leu Ala Lys Gly Leu Gly Leu Asn Ala Tyr Arg Ile
 65                  70                  75                  80

GGA ATA GAG TGG AGC AGA ATC TTT CCC TGG CCG ACG TGG ACG TCC GAT     288
Gly Ile Glu Trp Ser Arg Ile Phe Pro Trp Pro Thr Trp Thr Val Asp
                 85                  90                  95

ACC GAG GTC GAG TTC GAC ACT TAC GGT TTA GTA AAG GAC GTT AAG ATA     336
Thr Glu Val Glu Phe Asp Thr Tyr Gly Leu Val Lys Asp Val Lys Ile
            100                 105                 110

GAC AAG TCC ACC CTT GCT GAA CTC GAC AGG CTG GCC AAC AAG GAG GAG     384
Asp Lys Ser Thr Leu Ala Glu Leu Asp Arg Leu Ala Asn Lys Glu Glu
        115                 120                 125

GTA ATG TAC TAC AGG CGC GTT ATT CAG CAT TTG AGG GAG CTC GGC TTC     432
Val Met Tyr Tyr Arg Arg Val Ile Gln His Leu Arg Glu Leu Gly Phe
    130                 135                 140

AAG GTC TTC GTT AAC CTC AAC CAC TTC ACG CTT CCA ATA TGG CTC CAC     480
Lys Val Phe Val Asn Leu Asn His Phe Thr Leu Pro Ile Trp Leu His
145                 150                 155                 160

GAC CCG ATA GTG GCA AGG GAG AAG GCC CTC ACA AAC GAC AGA ATC GGC     528
Asp Pro Ile Val Ala Arg Glu Lys Ala Leu Thr Asn Asp Arg Ile Gly
                165                 170                 175

TGG GTC TCC CAG AGG ACA GTT GTT GAG TTT GCC AAG TAT GCT GCT TAC     576
Trp Val Ser Gln Arg Thr Val Val Glu Phe Ala Lys Tyr Ala Ala Tyr
            180                 185                 190

ATC GCC CAT GCG CTC GGA GAC CTC GTG GAC ACA TGG AGC ACC TTC AAC     624
Ile Ala His Ala Leu Gly Asp Leu Val Asp Thr Trp Ser Thr Phe Asn
        195                 200                 205

GAA CCT ATG GTA GTT GTG GAG CTC GGC TAC CTC GCC CCC TAC TCA GGA     672
Glu Pro Met Val Val Val Glu Leu Gly Tyr Leu Ala Pro Tyr Ser Gly
    210                 215                 220

TTT CCC CCG GGA GTC ATG AAC CCC GAG GCC GCG AAG CTG GCG ATC CTC     720
Phe Pro Pro Gly Val Met Asn Pro Glu Ala Ala Lys Leu Ala Ile Leu
225                 230                 235                 240

AAC ATG ATA AAC GCC CAC GCC TTG GCA TAT AAG ATG ATA AAG AGG TTC     768
Asn Met Ile Asn Ala His Ala Leu Ala Tyr Lys Met Ile Lys Arg Phe
                245                 250                 255
```

FIG. 12-1

AEPII 1a β-MANNOSIDASE (63GB1)(CONTINUED)

```
GAC ACC AAG AAG GCC GAT GAG GAT AGC AAG TCC CCT GCG GAC GTT GGC      816
Asp Thr Lys Lys Ala Asp Glu Asp Ser Lys Ser Pro Ala Asp Val Gly
            260                 265                 270
ATA ATT TAC AAC AAC ATC GGT GTT GCC TAC CCT AAA GAC CCT AAC GAT      864
Ile Ile Tyr Asn Asn Ile Gly Val Ala Tyr Pro Lys Asp Pro Asn Asp
            275                 280                 285
CCC AAG GAC GTT AAA GCA GCC GAA AAC GAC AAC TAC TTC CAC AGC GGA      912
Pro Lys Asp Val Lys Ala Ala Glu Asn Asp Asn Tyr Phe His Ser Gly
            290                 295                 300
CTG TTC TTT GAT GCC ATC CAC AAG GGT AAG CTC AAC ATA GAG TTC GAC      960
Leu Phe Phe Asp Ala Ile His Lys Gly Lys Leu Asn Ile Glu Phe Asp
305                 310                 315                 320
GGC GAA AAC TTT GTA AAA GTT AGA CAC CTA AAA GGC AAT GAC TGG ATA     1008
Gly Glu Asn Phe Val Lys Val Arg His Leu Lys Gly Asn Asp Trp Ile
            325                 330                 335
GGC CTC AAC TAC TAC ACC CGC GAG GTT GTT AGA TAT TCG GAG CCC AAG     1056
Gly Leu Asn Tyr Tyr Thr Arg Glu Val Val Arg Tyr Ser Glu Pro Lys
            340                 345                 350
TTC CCA AGT ATA CCC CTC ATA TCC TTC AAG GGC GTT CCC AAC TAC GGC     1104
Phe Pro Ser Ile Pro Leu Ile Ser Phe Lys Gly Val Pro Asn Tyr Gly
            355                 360                 365
TAC TCC TGC AGG CCC GGC ACG ACC TCC GCC GAT GGC ATG CCC GTC AGC     1152
Tyr Ser Cys Arg Pro Gly Thr Thr Ser Ala Asp Gly Met Pro Val Ser
            370                 375                 380
GAT ATC GGC TGG GAA GTC TAT CCC CAG GGA ATC TAC GAC TCG ATA GTC     1200
Asp Ile Gly Trp Glu Val Tyr Pro Gln Gly Ile Tyr Asp Ser Ile Val
385                 390                 395                 400
GAG GCC ACC AAG TAC AGT GTT CCT GTT TAC GTC ACC GAG AAC GGT GTT     1248
Glu Ala Thr Lys Tyr Ser Val Pro Val Tyr Val Thr Glu Asn Gly Val
            405                 410                 415
GCG GAT TCC GCG GAC ACG CTG AGG CCA TAC TAC ATA GTC AGC CAC GTC     1296
Ala Asp Ser Ala Asp Thr Leu Arg Pro Tyr Tyr Ile Val Ser His Val
            420                 425                 430
TCA AAG ATA GAG GAA GCC ATT GAG AAT GGA TAC CCC GTA AAA GGC TAC     1344
Ser Lys Ile Glu Glu Ala Ile Glu Asn Gly Tyr Pro Val Lys Gly Tyr
            435                 440                 445
ATG TAC TGG GCG CTT ACG GAT AAC TAC GAG TGG GCC CTC GGC TTC AGC     1392
Met Tyr Trp Ala Leu Thr Asp Asn Tyr Glu Trp Ala Leu Gly Phe Ser
            450                 455                 460
ATG AGG TTT GGT CTC TAC AAG GTC GAC CTC ATC TCC AAG GAG AGG ATC     1440
Met Arg Phe Gly Leu Tyr Lys Val Asp Leu Ile Ser Lys Glu Arg Ile
465                 470                 475                 480
CCG AGG GAG AGA AGC GTT GAG ATA TAT CGC AGG ATA GTG CAG TCC AAC     1488
Pro Arg Glu Arg Ser Val Glu Ile Tyr Arg Arg Ile Val Gln Ser Asn
            485                 490                 495
GGT GTT CCT AAG GAT ATC AAA GAG GAG TTC CTG AAG GGT GAG GAG AAA     1536
Gly Val Pro Lys Asp Ile Lys Glu Glu Phe Leu Lys Gly Glu Glu Lys
            500                 505                 510
TGA                                                                  1539
```

FIG. 12-2

OC1/4V ENDOGLUCANASE (33GP1)

```
ATG GTA GAA AGA CAC TTC AGA TAT GTT CTT ATT TGC ACC CTG TTT CTT      48
Met Val Glu Arg His Phe Arg Tyr Val Leu Ile Cys Thr Leu Phe Leu
 1               5                  10                  15

GTT ATG CTC CTA ATC TCA TCC ACT CAG TGT GGA AAA AAT GAA CCA AAC      96
Val Met Leu Leu Ile Ser Ser Thr Gln Cys Gly Lys Asn Glu Pro Asn
            20                  25                  30

AAA AGA GTG AAT AGC ATG GAA CAG TCA GTT GCT GAA AGT GAT AGC AAC     144
Lys Arg Val Asn Ser Met Glu Gln Ser Val Ala Glu Ser Asp Ser Asn
        35                  40                  45

TCA GCA TTT GAA TAC AAC AAA ATG GTA GGT AAA GGA GTA AAT ATT GGA     192
Ser Ala Phe Glu Tyr Asn Lys Met Val Gly Lys Gly Val Asn Ile Gly
    50                  55                  60

AAT GCT TTA GAA GCT CCT TTC GAA GGA GCT TGG GGA GTA AGA ATT GAG     240
Asn Ala Leu Glu Ala Pro Phe Glu Gly Ala Trp Gly Val Arg Ile Glu
65                  70                  75                  80

GAT GAA TAT TTT GAG ATA ATA AAG AAA AGG GGA TTT GAT TCT GTT AGG     288
Asp Glu Tyr Phe Glu Ile Ile Lys Lys Arg Gly Phe Asp Ser Val Arg
                85                  90                  95

ATT CCC ATA AGA TGG TCA GCA CAT ATA TCC GAA AAG CCA CCA TAT GAT     336
Ile Pro Ile Arg Trp Ser Ala His Ile Ser Glu Lys Pro Pro Tyr Asp
            100                 105                 110

ATT GAC AGG AAT TTC CTC GAA AGA GTT AAC CAT GTT GTC GAT AGG GCT     384
Ile Asp Arg Asn Phe Leu Glu Arg Val Asn His Val Val Asp Arg Ala
        115                 120                 125

CTT GAG AAT AAT TTA ACA GTA ATC ATC AAT ACG CAC CAT TTT GAA GAA     432
Leu Glu Asn Asn Leu Thr Val Ile Ile Asn Thr His His Phe Glu Glu
    130                 135                 140

CTC TAT CAA GAA CCG GAT AAA TAC GGC GAT GTT TTG GTG GAA ATT TGG     480
Leu Tyr Gln Glu Pro Asp Lys Tyr Gly Asp Val Leu Val Glu Ile Trp
145                 150                 155                 160

AGA CAG ATT GCA AAA TTC TTT AAA GAT TAC CCG GAA AAT CTG TTC TTT     528
Arg Gln Ile Ala Lys Phe Phe Lys Asp Tyr Pro Glu Asn Leu Phe Phe
                165                 170                 175

GAA ATC TAC AAC GAG CCT GCT CAG AAC TTG ACA GCT GAA AAA TGG AAC     576
Glu Ile Tyr Asn Glu Pro Ala Gln Asn Leu Thr Ala Glu Lys Trp Asn
            180                 185                 190

GCA CTT TAT CCA AAA GTG CTC AAA GTT ATC AGG GAG AGC AAT CCA ACC     624
Ala Leu Tyr Pro Lys Val Leu Lys Val Ile Arg Glu Ser Asn Pro Thr
        195                 200                 205

CGG ATT GTC ATT ATC GAT GCT CCA AAC TGG GCA CAC TAT AGC GCA GTG     672
Arg Ile Val Ile Ile Asp Ala Pro Asn Trp Ala His Tyr Ser Ala Val
    210                 215                 220
```

FIG. 13-1

OC1/4V ENDOGLUCANASE (33GP1)(CONTINUED)

```
AGA AGT CTA AAA TTA GTC AAC GAC AAA CGC ATC ATT GTT TCC TTC CAT      720
Arg Ser Leu Lys Leu Val Asn Asp Lys Arg Ile Ile Val Ser Phe His
225             230                 235                 240

TAC TAC GAA CCT TTC AAA TTC ACA CAT CAG GGT GCC GAA TGG GTT AAT      768
Tyr Tyr Glu Pro Phe Lys Phe Thr His Gln Gly Ala Glu Trp Val Asn
                245                 250                 255

CCC ATC CCA CCT GTT AGG GTT AAG TGG AAT GCC GAG GAA TGG GAA ATT      816
Pro Ile Pro Pro Val Arg Val Lys Trp Asn Gly Glu Glu Trp Glu Ile
                260                 265                 270

AAC CAA ATC AGA AGT CAT TTC AAA TAC GTG AGT GAC TGG GCA AAG CAA      864
Asn Gln Ile Arg Ser His Phe Lys Tyr Val Ser Asp Trp Ala Lys Gln
            275                 280                 285

AAT AAC GTA CCA ATC TTT CTT GGT GAA TTC GGT GCT TAT TCA AAA GCA      912
Asn Asn Val Pro Ile Phe Leu Gly Glu Phe Gly Ala Tyr Ser Lys Ala
        290                 295                 300

GAC ATG GAC TCA AGG GTT AAG TGG ACC GAA AGT GTG AGA AAA ATG GCG      960
Asp Met Asp Ser Arg Val Lys Trp Thr Glu Ser Val Arg Lys Met Ala
305                 310                 315                 320

GAA GAA TTT GGA TTT TCA TAC GCG TAT TGG GAA TTT TGT GCA GGA TTT     1008
Glu Glu Phe Gly Phe Ser Tyr Ala Tyr Trp Glu Phe Cys Ala Gly Phe
                325                 330                 335

GGC ATA TAC GAT AGA TGG TCT CAA AAC TGG ATC GAA CCA TTG GCA ACA     1056
Gly Ile Tyr Asp Arg Trp Ser Gln Asn Trp Ile Glu Pro Leu Ala Thr
                340                 345                 350

GCT GTG GTT GGC ACA GGC AAA GAG TAA                                 1083
Ala Val Val Gly Thr Gly Lys Glu
            355                 360
```

FIG. 13-2

THERMOTOGA MARITIMA PULLULANASE (6GP3)

```
ATG GAT CTT ACA AAG GTG GGG ATC ATA GTG AGG CTG AAC GAG TGG CAG      48
Met Asp Leu Thr Lys Val Gly Ile Ile Val Arg Leu Asn Glu Trp Gln
 1           5                  10                  15

GCA AAA GAC GTG GCA AAA GAC AGG TTC ATA GAG ATA AAA GAC GGA AAG      96
Ala Lys Asp Val Ala Lys Asp Arg Phe Ile Glu Ile Lys Asp Gly Lys
                 20                  25                  30

GCT GAA GTG TGG ATA CTC CAG GGA GTG GAA GAG ATT TTC TAC GAA AAA     144
Ala Glu Val Trp Ile Leu Gln Gly Val Glu Glu Ile Phe Tyr Glu Lys
             35                  40                  45

CCA GAC ACA TCT CCC AGA ATC TTC TTC GCA CAG GCA AGG TCG AAC AAG     192
Pro Asp Thr Ser Pro Arg Ile Phe Phe Ala Gln Ala Arg Ser Asn Lys
         50                  55                  60

GTG ATC GAG GCT TTT CTG ACC AAT CCT GTG GAT ACG AAA AAG AAA GAA     240
Val Ile Glu Ala Phe Leu Thr Asn Pro Val Asp Thr Lys Lys Lys Glu
 65                  70                  75                  80

CTC TTC AAG GTT ACT GTT GAC GGA AAA GAG ATT CCC GTC TCA AGA GTG     288
Leu Phe Lys Val Thr Val Asp Gly Lys Glu Ile Pro Val Ser Arg Val
                 85                  90                  95

GAA AAG GCC GAT CCC ACG GAC ATA GAC GTG ACG AAC TAC GTG AGA ATC     336
Glu Lys Ala Asp Pro Thr Asp Ile Asp Val Thr Asn Tyr Val Arg Ile
                100                 105                 110

GTC CTT TCT GAA TCC CTG AAA GAA GAA GAC CTC AGA AAA GAC GTG GAA     384
Val Leu Ser Glu Ser Leu Lys Glu Glu Asp Leu Arg Lys Asp Val Glu
             115                 120                 125

CTG ATC ATA GAA GGT TAC AAA CCG GCA AGA GTC ATC ATG ATG GAG ATC     432
Leu Ile Ile Glu Gly Tyr Lys Pro Ala Arg Val Ile Met Met Glu Ile
         130                 135                 140

CTG GAC GAC TAC TAT TAC GAT GGA GAG CTC GGA GCC GTA TAT TCT CCA     480
Leu Asp Asp Tyr Tyr Tyr Asp Gly Glu Leu Gly Ala Val Tyr Ser Pro
145                 150                 155                 160

GAG AAG ACG ATA TTC AGA GTC TGG TCC CCC GTT TCT AAG TGG GTA AAG     528
Glu Lys Thr Ile Phe Arg Val Trp Ser Pro Val Ser Lys Trp Val Lys
                 165                 170                 175

GTG CTT CTC TTC AAA AAC GGA GAA GAC ACA GAA CCG TAC CAG GTT GTG     576
Val Leu Leu Phe Lys Asn Gly Glu Asp Thr Glu Pro Tyr Gln Val Val
                 180                 185                 190

AAC ATG GAA TAC AAG GGA AAC GGG GTC TGG GAA GCG GTT GTT GAA GGC     624
Asn Met Glu Tyr Lys Gly Asn Gly Val Trp Glu Ala Val Val Glu Gly
             195                 200                 205

GAT CTC GAC GGA GTG TTC TAC CTC TAT CAG CTG GAA AAC TAC GGA AAG     672
Asp Leu Asp Gly Val Phe Tyr Leu Tyr Gln Leu Glu Asn Tyr Gly Lys
         210                 215                 220
```

FIG. 14-1

THERMOTOGA MARITIMA PULLULANASE (6GP3)(continued)

```
ATC ACA ACA ACC GTC GAT CCT TAT TCG AAA GCG GTT TAC GCA AAC AAC        720
Ile Arg Thr Thr Val Asp Pro Tyr Ser Lys Ala Val Tyr Ala Asn Asn
225                 230                 235                 240

CAA GAG AGC GCC GTT GTG AAT CTT GCC AGG ACA AAC CCA GAA GGA TGG        768
Gln Glu Ser Ala Val Val Asn Leu Ala Arg Thr Asn Pro Glu Gly Trp
                245                 250                 255

GAA AAC GAC AGG GGA CCG AAA ATC GAA GGA TAC GAA GAC GCG ATA ATC        816
Glu Asn Asp Arg Gly Pro Lys Ile Glu Gly Tyr Glu Asp Ala Ile Ile
            260                 265                 270

TAT GAA ATA CAC ATA GCG GAC ATC ACA GGA CTC GAA AAC TCC GGG GTA        864
Tyr Glu Ile His Ile Ala Asp Ile Thr Gly Leu Glu Asn Ser Gly Val
        275                 280                 285

AAA AAC AAA GGC CTC TAT CTC GGG CTC ACC GAA GAA AAC ACG AAA GGA        912
Lys Asn Lys Gly Leu Tyr Leu Gly Leu Thr Glu Glu Asn Thr Lys Gly
    290                 295                 300

CCG GGC GGT GTG ACA ACA GGC CTT TCG CAC CTT GTG GAA CTC GGT GTT        960
Pro Gly Gly Val Thr Thr Gly Leu Ser His Leu Val Glu Leu Gly Val
305                 310                 315                 320

ACA CAC GTT CAT ATA CTT CCT TTC TTT GAT TTC TAC ACA GGC GAC GAA       1008
Thr His Val His Ile Leu Pro Phe Phe Asp Phe Tyr Thr Gly Asp Glu
                325                 330                 335

CTC GAT AAA GAT TTC GAG AAG TAC TAC AAC TGG GGT TAC GAT CCT TAC       1056
Leu Asp Lys Asp Phe Glu Lys Tyr Tyr Asn Trp Gly Tyr Asp Pro Tyr
            340                 345                 350

CTG TTC ATG GTT CCG GAG GGC AGA TAC TCA ACC GAT CCC AAA AAC CCA       1104
Leu Phe Met Val Pro Glu Gly Arg Tyr Ser Thr Asp Pro Lys Asn Pro
        355                 360                 365

CAC ACG AGA ATC AGA GAA GTC AAA GAA ATG GTC AAA GCC CTT CAC AAA       1152
His Thr Arg Ile Arg Glu Val Lys Glu Met Val Lys Ala Leu His Lys
    370                 375                 380

CAC GGT ATA GGT GTG ATT ATG GAC ATG GTG TTC CCT CAC ACC TAC GGT       1200
His Gly Ile Gly Val Ile Met Asp Met Val Phe Pro His Thr Tyr Gly
385                 390                 395                 400

ATA GGC GAA CTC TCT GCG TTC GAT CAG ACC GTG CCG TAC TAC TTC TAC       1248
Ile Gly Glu Leu Ser Ala Phe Asp Gln Thr Val Pro Tyr Tyr Phe Tyr
                405                 410                 415

AGA ATC GAC AAG ACA GGT GCC TAT TTG AAC GAA AGC GGA TGT GGT AAC       1296
Arg Ile Asp Lys Thr Gly Ala Tyr Leu Asn Glu Ser Gly Cys Gly Asn
            420                 425                 430

GTC ATC GCA AGC GAA AGA CCC ATG ATG AGA AAA TTC ATA GTC GAT ACC       1344
Val Ile Ala Ser Glu Arg Pro Met Met Arg Lys Phe Ile Val Asp Thr
        435                 440                 445
```

FIG. 14-2

THERMOTOGA MARITIMA PULLULANASE (6GP3)(continued)

```
GTC ACC TAC TGG GTA AAG GAG TAT CAC ATA GAC GGA TTC AGG TTC GAT      1392
Val Thr Tyr Trp Val Lys Glu Tyr His Ile Asp Gly Phe Arg Phe Asp
    450             455                 460

CAG ATG GGT CTC ATC GAC AAA AAG ACA ATG CTC GAA GTC GAA AGA GCT      1440
Gln Met Gly Leu Ile Asp Lys Lys Thr Met Leu Glu Val Glu Arg Ala
465                 470                 475                 480

CTT CAT AAA ATC GAT CCA ACT ATC ATT CTC TAC GGC GAA CCG TGG GGT      1488
Leu His Lys Ile Asp Pro Thr Ile Ile Leu Tyr Gly Glu Pro Trp Gly
                485                 490                 495

GGA TGG GGA GCA CCG ATC AGG TTT GGA AAG AGC GAT GTC GCC GGC ACA      1536
Gly Trp Gly Ala Pro Ile Arg Phe Gly Lys Ser Asp Val Ala Gly Thr
            500                 505                 510

CAC GTG GCA GCT TTC AAC GAT GAG TTC AGA GAC CCA ATA AGG GGT TCC      1584
His Val Ala Ala Phe Asn Asp Glu Phe Arg Asp Ala Ile Arg Gly Ser
                515                 520                 525

GTG TTC AAC CCG AGC GTC AAG GGA TTC GTC ATG GGA GGA TAC GGA AAG      1632
Val Phe Asn Pro Ser Val Lys Gly Phe Val Met Gly Gly Tyr Gly Lys
            530                 535                 540

GAA ACC AAG ATC AAA AGG GGT GTT GTT GGA AGC ATA AAC TAC GAC GGA      1680
Glu Thr Lys Ile Lys Arg Gly Val Val Gly Ser Ile Asn Tyr Asp Gly545
550                 555                 560

AAA CTC ATC AAA AGT TTC GCC CTT GAT CCA GAA GAA ACT ATA AAC TAC      1728
Lys Leu Ile Lys Ser Phe Ala Leu Asp Pro Glu Glu Thr Ile Asn Tyr
                565                 570                 575

GCA GCG TGT CAC GAC AAC CAC ACA CTG TGG GAC AAG AAC TAC CTT GCC      1776
Ala Ala Cys His Asp Asn His Thr Leu Trp Asp Lys Asn Tyr Leu Ala
            580                 585                 590

GCC AAA GCT GAT AAG AAA AAG GAA TGG ACC GAA GAA GAA CTG AAA AAC      1824
Ala Lys Ala Asp Lys Lys Lys Glu Trp Thr Glu Glu Glu Leu Lys Asn
                595                 600                 605

GCC CAG AAA CTG GCT GGT GCG ATA CTT CTC ACT TCT CAA GGT GTT CCT      1872
Ala Gln Lys Leu Ala Gly Ala Ile Leu Leu Thr Ser Gln Gly Val Pro
            610                 615                 620

TTC CTC CAC GGA GGG CAG GAC TTC TGC AGG ACG ACG AAT TTC AAC GAC      1920
Phe Leu His Gly Gly Gln Asp Phe Cys Arg Thr Thr Asn Phe Asn Asp
625                 630                 635                 640

AAC TCC TAC AAC GCC CCT ATC TCG ATA AAC GGC TTC GAT TAC GAA AGA      1968
Asn Ser Tyr Asn Ala Pro Ile Ser Ile Asn Gly Phe Asp Tyr Glu Arg
                645                 650                 655

AAA CTT CAG TTC ATA GAC GTG TTC AAT TAC CAC AAG GGT CTC ATA AAA      2016
Lys Leu Gln Phe Ile Asp Val Phe Asn Tyr His Lys Gly Leu Ile Lys
                660                 665                 670
```

FIG. 14-3

THERMOTOGA MARITIMA PULLULANASE (6GP3)(continued)

```
CTC AGA AAA GAA CAC CCT GCT TTC AGG CTG AAA AAC GCT GAA GAG ATC      2064
Leu Arg Lys Glu His Pro Ala Phe Arg Leu Lys Asn Ala Glu Glu Ile
        675                 680                 685

AAA AAA CAC CTG GAA TTT CTC CCG GGC GGG AGA AGA ATA GTT GCG TTC      2112
Lys Lys His Leu Glu Phe Leu Pro Gly Gly Arg Arg Ile Val Ala Phe
        690                 695                 700

ATG CTT AAA GAC CAC GCA GGT GGT GAT CCC TGG AAA GAC ATC GTG GTG      2160
Met Leu Lys Asp His Ala Gly Gly Asp Pro Trp Lys Asp Ile Val Val
705                 710                 715                 720

ATT TAC AAT GGA AAC TTA GAG AAG ACA ACA TAC AAA CTG CCA GAA GGA      2208
Ile Tyr Asn Gly Asn Leu Glu Lys Thr Thr Tyr Lys Leu Pro Glu Gly
                725                 730                 735

AAA TGG AAT GTG GTT GTG AAC AGC CAG AAA GCC GGA ACA GAA GTG ATA      2256
Lys Trp Asn Val Val Val Asn Ser Gln Lys Ala Gly Thr Glu Val Ile
                740                 745                 750

GAA ACC GTC GAA GGA ACA ATA GAA CTC GAT CCG CTT TCC GCG TAC GTT      2304
Glu Thr Val Glu Gly Thr Ile Glu Leu Asp Pro Leu Ser Ala Tyr Val
        755                 760                 765

CTG TAC AGA GAG TGA                                                  2319
Leu Tyr Arg Glu
        770
```

FIG. 14-4

THERMOTOGA MARITIMA MSB8 (CLONE #6GP2) GLYCOSIDASE

```
CTT TTA TTG ATC GTT GAG CTC TCT TTC GTT CTC TTT GCA AGT GAC GAG     48
Leu Leu Leu Ile Val Glu Leu Ser Phe Val Leu Phe Ala Ser Asp Glu
 1           5                  10                  15

TTC GTG AAA GTG GAA AAC GGA AAA TTC GCT CTG AAC GGA AAA GAA TTC     96
Phe Val Lys Val Glu Asn Gly Lys Phe Ala Leu Asn Gly Lys Glu Phe
             20                  25                  30

AGA TTC ATT GGA AGC AAC AAC TAC TAC ATG CAC TAC AAG AGC AAC GGA    144
Arg Phe Ile Gly Ser Asn Asn Tyr Tyr Met His Tyr Lys Ser Asn Gly
         35                  40                  45

ATG ATA GAC AGT GTT CTG GAG AGT GCC AGA GAC ATG GGT ATA AAG GTC    192
Met Ile Asp Ser Val Leu Glu Ser Ala Arg Asp Met Gly Ile Lys Val
     50                  55                  60

CTC AGA ATC TGG GGT TTC CTC GAC GGG GAG AGT TAC TGC AGA GAC AAG    240
Leu Arg Ile Trp Gly Phe Leu Asp Gly Glu Ser Tyr Cys Arg Asp Lys
 65                  70                  75                  80

AAC ACC TAC ATG CAT CCT GAG CCC GGT GTT TTC GGG GTG CCA GAA GGA    288
Asn Thr Tyr Met His Pro Glu Pro Gly Val Phe Gly Val Pro Glu Gly
                 85                  90                  95

ATA TCG AAC GCC CAG AGC GGT TTC GAA AGA CTC GAC TAC ACA GTT GCG    336
Ile Ser Asn Ala Gln Ser Gly Phe Glu Arg Leu Asp Tyr Thr Val Ala
             100                 105                 110

AAA GCG AAA GAA CTC GGT ATA AAA CTT GTC ATT GTT CTT GTG AAC AAC    384
Lys Ala Lys Glu Leu Gly Ile Lys Leu Val Ile Val Leu Val Asn Asn
         115                 120                 125

TGG GAC GAC TTC GGT GGA ATG AAC CAG TAC GTG AGG TGG TTT GGA GGA    432
Trp Asp Asp Phe Gly Gly Met Asn Gln Tyr Val Arg Trp Phe Gly Gly
     130                 135                 140

ACC CAT CAC GAC GAT TTC TAC AGA GAT GAG AAG ATC AAA GAA GAG TAC    480
Thr His His Asp Asp Phe Tyr Arg Asp Glu Lys Ile Lys Glu Glu Tyr
145                 150                 155                 160

AAA AAG TAC GTC TCC TTT CTC GTA AAC CAT GTC AAT ACC TAC ACG GGA    528
Lys Lys Tyr Val Ser Phe Leu Val Asn His Val Asn Thr Tyr Thr Gly
                 165                 170                 175

GTT CCT TAC AGG GAA GAG CCC ACC ATC ATG GCC TGG GAG CTT GCA AAC    576
Val Pro Tyr Arg Glu Glu Pro Thr Ile Met Ala Trp Glu Leu Ala Asn
             180                 185                 190

GAA CCG CGC TGT GAG ACG GAC AAA TCG GGA ACG CTC GTT GAG TGG        624
Glu Pro Arg Cys Glu Thr Asp Lys Ser Gly Asn Thr Leu Val Glu Trp
         195                 200                 205

GTG AAG GAG ATG AGC TCC TAC ATA AAG AGT CTG GAT CCC AAC CAC CTC    672
Val Lys Glu Met Ser Ser Tyr Ile Lys Ser Leu Asp Pro Asn His Leu
     210                 215                 220
```

FIG. 15-1

```
GTG GCT GTG GGG GAC GAA GGA TTC TTC AGC AAC TAC GAA GGA TTC AAA      720
Val Ala Val Gly Asp Glu Gly Phe Phe Ser Asn Tyr Glu Gly Phe Lys
225                 230                 235                 240

CCT TAC GGT GGA GAA GCC GAG TGG GCC TAC AAC GGC TGG TCC GGT GTT      768
Pro Tyr Gly Gly Glu Ala Glu Trp Ala Tyr Asn Gly Trp Ser Gly Val
                245                 250                 255

GAC TGG AAG AAG CTC CTT TCG ATA GAG ACG GTG GAC TTC GGC ACG TTC      816
Asp Trp Lys Lys Leu Leu Ser Ile Glu Thr Val Asp Phe Gly Thr Phe
            260                 265                 270

CAC CTC TAT CCG TCC CAC TGG GGT GTC AGT CCA GAG AAC TAT GCC CAG      864
His Leu Tyr Pro Ser His Trp Gly Val Ser Pro Glu Asn Tyr Ala Gln
        275                 280                 285

TGG GGA GCG AAG TGG ATA GAA GAC CAC ATA AAG ATC GCA AAA GAG ATC      912
Trp Gly Ala Lys Trp Ile Glu Asp His Ile Lys Ile Ala Lys Glu Ile
290                 295                 300

GGA AAA CCC GTT GTT CTG GAA GAA TAT GGA ATT CCA AAG AGT GCG CCA      960
Gly Lys Pro Val Val Leu Glu Glu Tyr Gly Ile Pro Lys Ser Ala Pro
305                 310                 315                 320

GTT AAC AGA ACG GCC ATC TAC AGA CTC TGG AAC GAT CTG GTC TAC GAT     1008
Val Asn Arg Thr Ala Ile Tyr Arg Leu Trp Asn Asp Leu Val Tyr Asp
                325                 330                 335

CTC GGT GGA GAT GGA GCG ATG TTC TGG ATG CTC GCG GGA ATC GGG GAA     1056
Leu Gly Gly Asp Gly Ala Met Phe Trp Met Leu Ala Gly Ile Gly Glu
            340                 345                 350

GGT TCG GAC AGA GAC GAG AGA GGG TAC TAT CCG GAC TAC GAC GGT TTC     1104
Gly Ser Asp Arg Asp Glu Arg Gly Tyr Tyr Pro Asp Tyr Asp Gly Phe
        355                 360                 365

AGA ATA GTG AAC GAC GAC AGT CCA GAA GCG GAA CTG ATA AGA GAA TAC     1152
Arg Ile Val Asn Asp Asp Ser Pro Glu Ala Glu Leu Ile Arg Glu Tyr
370                 375                 380

GCG AAG CTG TTC AAC ACA GGT GAA GAC ATA AGA GAA GAC ACC TGC TCT     1200
Ala Lys Leu Phe Asn Thr Gly Glu Asp Ile Arg Glu Asp Thr Cys Ser
385                 390                 395                 400

TTC ATC CTT CCA AAA GAC GGC ATG GAG ATC AAA AAG ACC GTG GAA GTG     1248
Phe Ile Leu Pro Lys Asp Gly Met Glu Ile Lys Lys Thr Val Glu Val
                405                 410                 415

AGG GCT GGT GTT TTC GAC TAC AGC AAC ACG TTT GAA AAG TTG TCT GTC     1296
Arg Ala Gly Val Phe Asp Tyr Ser Asn Thr Phe Glu Lys Leu Ser Val
            420                 425                 430

AAA GTC GAA GAT CTG GTT TTT GAA AAT GAG ATA GAG CAT CTC GGA TAC     1344
Lys Val Glu Asp Leu Val Phe Glu Asn Glu Ile Glu His Leu Gly Tyr
        435                 440                 445

GGA ATT TAC GGC TTT GAT CTC GAC ACA ACC CGG ATC CCG GAT GGA GAA     1392
Gly Ile Tyr Gly Phe Asp Leu Asp Thr Thr Arg Ile Pro Asp Gly Glu
450                 455                 460
```

FIG. 15-2

```
CAT GAA ATG TTC CTT GAA GGC CAC TTT CAG GGA AAA ACG GTG AAA GAC        1440
His Glu Met Phe Leu Glu Gly His Phe Gln Gly Lys Thr Val Lys Asp
465                 470                 475                 480

TCT ATC AAA GCG AAA GTG GTG AAC GAA GCA CGG TAC GTG CTC GCA GAG        1488
Ser Ile Lys Ala Lys Val Val Asn Glu Ala Arg Tyr Val Leu Ala Glu
                485                 490                 495

GAA GTT GAT TTT TCC TCT CCA GAA GAG GTG AAA AAC TGG TGG AAC AGC        1536
Glu Val Asp Phe Ser Ser Pro Glu Glu Val Lys Asn Trp Trp Asn Ser
            500                 505                 510

GGA ACC TGG CAG GCA GAG TTC GGG TCA CCT GAC ATT GAA TGG AAC GGT        1584
Gly Thr Trp Gln Ala Glu Phe Gly Ser Pro Asp Ile Glu Trp Asn Gly
        515                 520                 525

GAG GTG GGA AAT GGA GCA CTG CAG CTG AAC GTG AAA CTG CCC GGA AAG        1632
Glu Val Gly Asn Gly Ala Leu Gln Leu Asn Val Lys Leu Pro Gly Lys
    530                 535                 540

AGC GAC TGG GAA GAA GTG AGA GTA GCA AGG AAG TTC GAA AGA CTC TCA        1680
Ser Asp Trp Glu Glu Val Arg Val Ala Arg Lys Phe Glu Arg Leu Ser
545                 550                 555                 560

GAA TGT GAG ATC CTC GAG TAC GAC ATC TAC ATT CCA AAC GTC GAG GGA        1728
Glu Cys Glu Ile Leu Glu Tyr Asp Ile Tyr Ile Pro Asn Val Glu Gly
                565                 570                 575

CTC AAG GGA AGG TTG AGG CCG TAC GCG GTT CTG AAC CCC GGC TGG GTG        1776
Leu Lys Gly Arg Leu Arg Pro Tyr Ala Val Leu Asn Pro Gly Trp Val
            580                 585                 590

AAG ATA GGC CTC GAC ATG AAC AAC GCG AAC GTG GAA AGT GCG GAG ATC        1824
Lys Ile Gly Leu Asp Met Asn Asn Ala Asn Val Glu Ser Ala Glu Ile
        595                 600                 605

ATC ACT TTC GGC GGA AAA GAG TAC AGA AGA TTC CAT GTA AGA ATT GAG        1872
Ile Thr Phe Gly Gly Lys Glu Tyr Arg Arg Phe His Val Arg Ile Glu
    610                 615                 620

TTC GAC AGA ACA GCG GGG GTG AAA GAA CTT CAC ATA GGA GTT GTC GGT        1920
Phe Asp Arg Thr Ala Gly Val Lys Glu Leu His Ile Gly Val Val Gly
625                 630                 635                 640

GAT CAT CTG AGG TAC GAT GGA CCG ATT TTC ATC GAT AAT GTG AGA CTT        1968
Asp His Leu Arg Tyr Asp Gly Pro Ile Phe Ile Asp Asn Val Arg Leu
                645                 650                 655

TAT AAA AGA ACA GGA GGT ATG TGA                                        1992
Tyr Lys Arg Thr Gly Gly Met
                660
```

FIG. 15-3

THERMOTOGA MARITIMA MSB8 (6gb4)

```
ATG AAA AGA ATC GAC CTG AAT GGT TTC TGG AGC GTT AGG GAT AAC GAA       48
Met Lys Arg Ile Asp Leu Asn Gly Phe Trp Ser Val Arg Asp Asn Glu
 1               5                  10                  15

GGG AGA TTT TCG TTT GAA GGG ACT GTG CCA GGG GTT GTC CAG GCA GAT       96
Gly Arg Phe Ser Phe Glu Gly Thr Val Pro Gly Val Val Gln Ala Asp
                20                  25                  30

CTG GTC AGA AAA GGT CTT CTT CCA CAC CCG TAC GTT GGG ATG AAC GAA      144
Leu Val Arg Lys Gly Leu Leu Pro His Pro Tyr Val Gly Met Asn Glu
         35                  40                  45

GAT CTC TTC AAG GAA ATA GAA GAC AGA GAG TGG ATC TAC GAG AGG GAG      192
Asp Leu Phe Lys Glu Ile Glu Asp Arg Glu Trp Ile Tyr Glu Arg Glu
     50                  55                  60

TTC GAG TTC AAA GAA GAT GTG AAA GAG GGG GAA CGT GTC GAT CTC GTT      240
Phe Glu Phe Lys Glu Asp Val Lys Glu Gly Glu Arg Val Asp Leu Val
 65                  70                  75                  80

TTT GAG GGC GTC GAC ACG CTG TCG GAT GTT TAT CTG AAC GGT GTT TAC      288
Phe Glu Gly Val Asp Thr Leu Ser Asp Val Tyr Leu Asn Gly Val Tyr
                 85                  90                  95

CTT GGA AGC ACC GAA GAC ATG TTC ATC GAG TAT CGC TTC GAT GTC ACG      336
Leu Gly Ser Thr Glu Asp Met Phe Ile Glu Tyr Arg Phe Asp Val Thr
            100                 105                 110

AAC GTG TTG AAA GAA AAG AAT CAC CTG AAG GTG TAC ATA AAA TCT CCC      384
Asn Val Leu Lys Glu Lys Asn His Leu Lys Val Tyr Ile Lys Ser Pro
        115                 120                 125

ATC AGA GTT CCG AAA ACT CTC GAG CAG AAC TAC GGG GTC CTC GGC GGT      432
Ile Arg Val Pro Lys Thr Leu Glu Gln Asn Tyr Gly Val Leu Gly Gly
    130                 135                 140

CCT GAA GAT CCC ATC AGA GGA TAC ATA AGA AAA GCC CAG TAT TCG TAC      480
Pro Glu Asp Pro Ile Arg Gly Tyr Ile Arg Lys Ala Gln Tyr Ser Tyr
145                 150                 155                 160

GGA TGG GAC TGG GGT GCC AGA ATC GTT ACA AGC GGT ATT TGG AAA CCC      528
Gly Trp Asp Trp Gly Ala Arg Ile Val Thr Ser Gly Ile Trp Lys Pro
                165                 170                 175

GTC TAC CTC GAG GTG TAC AGG GCA CGT CTT CAG GAT TCA ACG GCT TAT      576
Val Tyr Leu Glu Val Tyr Arg Ala Arg Leu Gln Asp Ser Thr Ala Tyr
            180                 185                 190

CTG TTG GAA CTT GAG GGG AAA GAT GCC CTT GTG AGG GTG AAC GGT TTC      624
Leu Leu Glu Leu Glu Gly Lys Asp Ala Leu Val Arg Val Asn Gly Phe
        195                 200                 205

GTA CAC GGG GAA GGA AAT CTC ATT GTG GAA GTT TAT GTA AAC GGT GAA      672
Val His Gly Glu Gly Asn Leu Ile Val Glu Val Tyr Val Asn Gly Glu
    210                 215                 220

AAG ATA GGG GAG TTT CCT GTT CTT GAA AAG AAC GGA GAA AAG CTC TTC      720
Lys Ile Gly Glu Phe Pro Val Leu Glu Lys Asn Gly Glu Lys Leu Phe
225                 230                 235                 240
```

FIG. 16-1

```
GAT GGA GTG TTC CAC CTG AAA GAT GTG AAA CTA TGG TAT CCG TGG AAC      768
Asp Gly Val Phe His Leu Lys Asp Val Lys Leu Trp Tyr Pro Trp Asn
            245                 250                 255

GTG GGG AAA CCG TAC CTG TAC GAT TTC GTT TTC GTG TTG AAA GAC TTA      816
Val Gly Lys Pro Tyr Leu Tyr Asp Phe Val Phe Val Leu Lys Asp Leu
            260                 265                 270

AAC GGA GAG ATC TAC AGA GAA GAA AAG AAA ATC GGT TTG AGA AGA GTC      864
Asn Gly Glu Ile Tyr Arg Glu Glu Lys Lys Ile Gly Leu Arg Arg Val
            275                 280                 285

AGA ATC GTT CAG GAG CCC GAT GAA GAA GGA AAA ACT TTC ATA TTC GAA      912
Arg Ile Val Gln Glu Pro Asp Glu Glu Gly Lys Thr Phe Ile Phe Glu
            290                 295                 300

ATC AAC GGT GAG AAA GTC TTC GCT AAG GGT GCT AAC TGG ATT CCC TCA      960
Ile Asn Gly Glu Lys Val Phe Ala Lys Gly Ala Asn Trp Ile Pro Ser
305                 310                 315                 320

GAA AAC ATC CTC ACG TGG TTG AAG GAG GAA GAT TAC GAA AAG CTC GTC     1008
Glu Asn Ile Leu Thr Trp Leu Lys Glu Glu Asp Tyr Glu Lys Leu Val
            325                 330                 335

AAA ATG GCA AGG AGT GCC AAT ATG AAC ATG CTC AGG GTC TGG GGA GGA     1056
Lys Met Ala Arg Ser Ala Asn Met Asn Met Leu Arg Val Trp Gly Gly
            340                 345                 350

GGA ATC TAC GAG AGA GAG ATC TTC TAC AGA CTC TGT GAT GAA CTC GGT     1104
Gly Ile Tyr Glu Arg Glu Ile Phe Tyr Arg Leu Cys Asp Glu Leu Gly
            355                 360                 365

ATC ATG GTG TGG CAG GAT TTC ATG TAC GCG TGT CTT GAA TAT CCG GAT     1152
Ile Met Val Trp Gln Asp Phe Met Tyr Ala Cys Leu Glu Tyr Pro Asp
            370                 375                 380

CAT CTT CCG TGG TTC AGA AAA CTC GCG AAC GAA GAG GCA AGA AAG ATT     1200
His Leu Pro Trp Phe Arg Lys Leu Ala Asn Glu Glu Ala Arg Lys Ile
385                 390                 395                 400

GTG AGA AAA CTC AGA TAC CAT CCC TCC ATT GTT CTC TGG TGC GGA AAC     1248
Val Arg Lys Leu Arg Tyr His Pro Ser Ile Val Leu Trp Cys Gly Asn
            405                 410                 415

AAC GAA AAC AAC TGG GGA TTC GAT GAA TGG GGA AAT ATG GCC AGA AAA     1296
Asn Glu Asn Asn Trp Gly Phe Asp Glu Trp Gly Asn Met Ala Arg Lys
            420                 425                 430

GTG GAT GGT ATC AAC CTC GGA AAC AGG CTC TAC CTC TTC GAT TTT CCT     1344
Val Asp Gly Ile Asn Leu Gly Asn Arg Leu Tyr Leu Phe Asp Phe Pro
            435                 440                 445

GAG ATT TGT GCC GAA GAA GAC CCG TCC ACT CCC TAT TGG CCA TCC AGT     1392
Glu Ile Cys Ala Glu Glu Asp Pro Ser Thr Pro Tyr Trp Pro Ser Ser
450                 455                 460

CCA TAC GGC GGT GAA AAA GCG AAC AGC GAA AAG GAA GGA GAC AGG CAC     1440
Pro Tyr Gly Gly Glu Lys Ala Asn Ser Glu Lys Glu Gly Asp Arg His
465                 470                 475                 480
```

FIG. 16-2

```
GTC TGG TAC GTG TGG AGT GGC TGG ATG AAC TAC GAA AAC TAC GAA AAA    1488
Val Trp Tyr Val Trp Ser Gly Trp Met Asn Tyr Glu Asn Tyr Glu Lys
            485                     490                 495

GAC ACC GGA AGG TTC ATC AGC GAG TTT GGA TTT CAG GGT GCT CCC CAT    1536
Asp Thr Gly Arg Phe Ile Ser Glu Phe Gly Phe Gln Gly Ala Pro His
            500                     505                 510

CCA GAG ACG ATA GAG TTC TTT TCA AAA CCC GAG GAA AGA GAG ATA TTC    1584
Pro Glu Thr Ile Glu Phe Phe Ser Lys Pro Glu Glu Arg Glu Ile Phe
            515                     520                 525

CAT CCC GTC ATG CTG AAG CAC AAC AAA CAG GTG GAA GGA CAG GAA AGA    1632
His Pro Val Met Leu Lys His Asn Lys Gln Val Glu Gly Gln Glu Arg
            530                     535                 540

TTG ATC AGG TTC ATA TTC GGA AAT TTT GGA AAG TGT AAA GAT TTC GAC    1680
Leu Ile Arg Phe Ile Phe Gly Asn Phe Gly Lys Cys Lys Asp Phe Asp
545                     550                 555                 560

AGT TTT GTG TAT CTG TCC CAG CTC AAC CAG GCG GAG GCG ATC AAG TTC    1728
Ser Phe Val Tyr Leu Ser Gln Leu Asn Gln Ala Glu Ala Ile Lys Phe
            565                     570                 575

GGT GTT GAA CAC TGG CGA AGC AGG AAG TAC AAA ACG GCC GGC GCT CTC    1776
Gly Val Glu His Trp Arg Ser Arg Lys Tyr Lys Thr Ala Gly Ala Leu
            580                     585                 590

TTC TGG CAG TTC AAC GAC AGC TGG CCG GTC TTC AGC TGG TCC GCA GTC    1824
Phe Trp Gln Phe Asn Asp Ser Trp Pro Val Phe Ser Trp Ser Ala Val
            595                     600                 605

GAT TAC TTC AAA AGG CCC AAA GCT CTC TAC TAC TAT GCG AGA AGA TTC    1872
Asp Tyr Phe Lys Arg Pro Lys Ala Leu Tyr Tyr Tyr Ala Arg Arg Phe
            610                     615                 620

TTC GCT GAA GTT CTA CCC GTT TTG AAG AAG AGA GAC AAC AAA ATA GAA    1920
Phe Ala Glu Val Leu Pro Val Leu Lys Lys Arg Asp Asn Lys Ile Glu
625                     630                 635                 640

CTG CTG GTG GGT GAG CGA TCT GAG GGA GAC AAA AGA AGT CTC TCT CAG    1968
Leu Leu Val Gly Glu Arg Ser Glu Gly Asp Lys Arg Ser Leu Ser Gln
            645                     650                 655

GCT TGC AGC CTA CGA GAA GAA GGG AGA AAA GGT ATT CGA AAA GAC TTA    2016
Ala Cys Ser Leu Arg Glu Glu Gly Arg Lys Gly Ile Arg Lys Asp Leu
            660                     665                 670

CAG AAC GGT ACT CCC AGC AGA CGG TGT GAG TTT GGT TGA                2055
Gln Asn Gly Thr Pro Ser Arg Arg Cys Glu Phe Gly
            675                     680
```

FIG. 16-3

BANKIA GOULDI (37gp4)

```
ATG AAA AAA AAT CTA CTA ATG TTT AAA AGG CTT ACG TAT CTA CCT TTG      48
Met Lys Lys Asn Leu Leu Met Phe Lys Arg Leu Thr Tyr Leu Pro Leu
 1               5                  10                  15

TTT TTA ATG CTG CTC TCA CTA AGT TCA GTA GCT CAA TCT CCT GTA GAA      96
Phe Leu Met Leu Leu Ser Leu Ser Ser Val Ala Gln Ser Pro Val Glu
                20                  25                  30

AAA CAT GGC CGT TTA CAA GTT GAC GGA AAC CGC ATT CTT AAT GCG TCT     144
Lys His Gly Arg Leu Gln Val Asp Gly Asn Arg Ile Leu Asn Ala Ser
            35                  40                  45

GGA GAA ATT ACG AGC TTA GCT GGT AAC AGC CTC TTT TGG AGT AAT GCT     192
Gly Glu Ile Thr Ser Leu Ala Gly Asn Ser Leu Phe Trp Ser Asn Ala
    50                  55                  60

GGA GAC ACC TCC GAT TTT TAT AAT GCA GAA ACT GTT GAT TTT TTA GCA     240
Gly Asp Thr Ser Asp Phe Tyr Asn Ala Glu Thr Val Asp Phe Leu Ala
65                  70                  75                  80

GAA AAC TGG AAT AGC TCA CTT ATT AGA ATA GCT ATG GGC GTA AAA GAA     288
Glu Asn Trp Asn Ser Ser Leu Ile Arg Ile Ala Met Gly Val Lys Glu
                85                  90                  95

AAT TGG GAT GGC GGA AAT GGC TAT ATT GAT AGT CCG CAG GAG CAA GAA     336
Asn Trp Asp Gly Gly Asn Gly Tyr Ile Asp Ser Pro Gln Glu Gln Glu
            100                 105                 110

GCT AAA ATT AGA AAA GTT ATT GAT GCA GCT ATT GCT AAC GGC ATA TAT     384
Ala Lys Ile Arg Lys Val Ile Asp Ala Ala Ile Ala Asn Gly Ile Tyr
    115                 120                 125

GTA ATA ATA GAC TGG CAC ACT CAC GAA GCA GAG TTA TAC ACA GAT GAG     432
Val Ile Ile Asp Trp His Thr His Glu Ala Glu Leu Tyr Thr Asp Glu
130                 135                 140

GCT GTT GAC TTT TTT ACC AGA ATG GCA GAC CTA TAC GGA GAT ACT CCC     480
Ala Val Asp Phe Phe Thr Arg Met Ala Asp Leu Tyr Gly Asp Thr Pro
145                 150                 155                 160

AAT GTA ATG TAT GAA ATT TAT AAC GAG CCT ATA TAC CAA AGT TGG CCT     528
Asn Val Met Tyr Glu Ile Tyr Asn Glu Pro Ile Tyr Gln Ser Trp Pro
                165                 170                 175

GTT ATT AAG AAT TAT GCA GAG CAA GTA ATT GCT GGT ATA CGT TCT AAA     576
Val Ile Lys Asn Tyr Ala Glu Gln Val Ile Ala Gly Ile Arg Ser Lys
            180                 185                 190

GAC CCA GAT AAT TTA ATA ATT GTA GGT ACT AGC AAT TAT TCT CAG CAA     624
Asp Pro Asp Asn Leu Ile Ile Val Gly Thr Ser Asn Tyr Ser Gln Gln
    195                 200                 205

GTT GAT GTA GCA TCA GCA GAC CCA ATA TCT GAT ACT AAT GTG GCA TAT     672
Val Asp Val Ala Ser Ala Asp Pro Ile Ser Asp Thr Asn Val Ala Tyr
210                 215                 220
```

FIG. 17-1

```
ACT TTA CAT TTT TAT GCA GCA TTT AAC CCG CAT GAT AAC TTA AGA AAT    720
Thr Leu His Phe Tyr Ala Ala Phe Asn Pro His Asp Asn Leu Arg Asn
225                 230                 235                 240

GTA GCA CAG ACA GCA TTA GAT AAT AAT GTT GCT TTG TTT GTT ACA GAA    768
Val Ala Gln Thr Ala Leu Asp Asn Asn Val Ala Leu Phe Val Thr Glu
            245                 250                 255

TGG GGT ACA ATT TTA AAT ACC GGA CAA GGA GAA CCA GAC AAA GAA AGC    816
Trp Gly Thr Ile Leu Asn Thr Gly Gln Gly Glu Pro Asp Lys Glu Ser
        260                 265                 270

ACT AAT ACT TGG ATG GCC TTT TTG AAA GAA AAA GGT ATA AGT CAC GCT    864
Thr Asn Thr Trp Met Ala Phe Leu Lys Glu Lys Gly Ile Ser His Ala
    275                 280                 285

AAT TGG TCT TTG AGT GAC AAA GCT TTT CCT GAA ACA GGG TCT GTA GTT    912
Asn Trp Ser Leu Ser Asp Lys Ala Phe Pro Glu Thr Gly Ser Val Val
290                 295                 300

CAA GCA GGA CAA GGT GTA TCT GGT TTA ATT AGC AAT AAA CTT ACA GCC    960
Gln Ala Gly Gln Gly Val Ser Gly Leu Ile Ser Asn Lys Leu Thr Ala
305                 310                 315                 320

TCT GGT GAA ATT GTA AAA AAC ATC ATC CAA AAC TGG GAT ACA GAG ACC   1008
Ser Gly Glu Ile Val Lys Asn Ile Ile Gln Asn Trp Asp Thr Glu Thr
            325                 330                 335

TCT ACA GGA CCT AAA ACA ACA CAA TGT AGT ACT ATA GAA TGT ATT AGA   1056
Ser Thr Gly Pro Lys Thr Thr Gln Cys Ser Thr Ile Glu Cys Ile Arg
        340                 345                 350

GCT GCA ATG GAA ACA GCA CAA GCA GGA GAT GAA ATT ATA ATT GCC CCT   1104
Ala Ala Met Glu Thr Ala Gln Ala Gly Asp Glu Ile Ile Ile Ala Pro
    355                 360                 365

GGA AAC TAC AAT TTT CAA GAC AAG ATA CAA GGT GCC TTT AAC CGT AGT   1152
Gly Asn Tyr Asn Phe Gln Asp Lys Ile Gln Gly Ala Phe Asn Arg Ser
370                 375                 380

GTT TAC CTT TAT GGT AGT GCT AAC GGA AAC AGT ACA AAC CCT ATT ATA   1200
Val Tyr Leu Tyr Gly Ser Ala Asn Gly Asn Ser Thr Asn Pro Ile Ile
385                 390                 395                 400

TTA AGA GGC GAA AGC GCT ACA AAC CCT CCT GTT TTC TCA GGA TTA GAT   1248
Leu Arg Gly Glu Ser Ala Thr Asn Pro Pro Val Phe Ser Gly Leu Asp
            405                 410                 415

TAT AAC AAT GGC TAC CTA TTA AGT ATT GAA GGT GAT TAT TGG AAT ATT   1296
Tyr Asn Asn Gly Tyr Leu Leu Ser Ile Glu Gly Asp Tyr Trp Asn Ile
        420                 425                 430

AAA GAT ATA GAG TTT AAA ACT GGG TCT AAA GGT ATT GTT CTT GAC AAT   1344
Lys Asp Ile Glu Phe Lys Thr Gly Ser Lys Gly Ile Val Leu Asp Asn
    435                 440                 445

TCT AAT GGT AGT AAA TTA AAA AAC CTT GTT GTT CAT GAT ATT GGA GAA   1392
Ser Asn Gly Ser Lys Leu Lys Asn Leu Val Val His Asp Ile Gly Glu
450                 455                 460
```

FIG. 17-2

```
GAA GCT ATT CAC TTG CGT GAT GGA TCT AGC AAT AAT AGT ATA GAT GGT    1440
Glu Ala Ile His Leu Arg Asp Gly Ser Ser Asn Asn Ser Ile Asp Gly
465                 470                 475                 480

TGC ACT ATA TAC AAT ACA GGT AGA ACT AAA CCT GGT TTT GGT GAA GGT    1488
Cys Thr Ile Tyr Asn Thr Gly Arg Thr Lys Pro Gly Phe Gly Glu Gly
                485                 490                 495

TTA TAT GTA GGC TCA GAT AAA GGA CAA CAT GAC ACT TAT GAA AGA GCT    1536
Leu Tyr Val Gly Ser Asp Lys Gly Gln His Asp Thr Tyr Glu Arg Ala
                500                 505                 510

TGT AAC AAT AAC ACT ATT GAA AAC TGT ACC GTT GGA CCC AAT GTA ACA    1584
Cys Asn Asn Asn Thr Ile Glu Asn Cys Thr Val Gly Pro Asn Val Thr
            515                 520                 525

GCA GAA GGC GTA GAT GTT AAG GAA GGT ACA ATG AAC ACT ATT ATA AGA    1632
Ala Glu Gly Val Asp Val Lys Glu Gly Thr Met Asn Thr Ile Ile Arg
        530                 535                 540

AAT TGC GTG TTT TCT GCA GAA GGA ATT TCA GGA GAA AAT AGC TCA GAT    1680
Asn Cys Val Phe Ser Ala Glu Gly Ile Ser Gly Glu Asn Ser Ser Asp
545                 550                 555                 560

GCT TTT ATT GAT TTA AAA GGA GCC TAT GGT TTT GTA TAC AGA AAC ACG    1728
Ala Phe Ile Asp Leu Lys Gly Ala Tyr Gly Phe Val Tyr Arg Asn Thr
                565                 570                 575

TTT AAT GTT GAT GGT TCT GAA GTA ATA AAT ACT GGA GTA GAC TTT TTA    1776
Phe Asn Val Asp Gly Ser Glu Val Ile Asn Thr Gly Val Asp Phe Leu
                580                 585                 590

GAT AGA GGT ACA GGA TTT AAT ACA GGT TTT AGA AAT GCA ATA TTT GAA    1824
Asp Arg Gly Thr Gly Phe Asn Thr Gly Phe Arg Asn Ala Ile Phe Glu
            595                 600                 605

AAT ACA TAT AAC CTT GGC AGT AGA GCT TCA GAA ATT TCA ACT GCT CGT    1872
Asn Thr Tyr Asn Leu Gly Ser Arg Ala Ser Glu Ile Ser Thr Ala Arg
        610                 615                 620

AAA AAA CAA GGT TCT CCT GAA CAA ACT CAC GTT TGG GAT AAT ATT AGA    1920
Lys Lys Gln Gly Ser Pro Glu Gln Thr His Val Trp Asp Asn Ile Arg
625                 630                 635                 640

AAC CCT AAT TCT GTT GAT TTT CCA ATA AGT GAT GGT ACA GAA AAT CTA    1968
Asn Pro Asn Ser Val Asp Phe Pro Ile Ser Asp Gly Thr Glu Asn Leu
                645                 650                 655

GTA AAT AAA TTC TGC CCA GAT TGG AAT ATA GAA CCA TGT AAT CCT GTA    2016
Val Asn Lys Phe Cys Pro Asp Trp Asn Ile Glu Pro Cys Asn Pro Val
                660                 665                 670

GAC GAA ACC AAC CAA GCA CCT ACA ATA AGC TTC CTA TCT CCT GTT AAC    2064
Asp Glu Thr Asn Gln Ala Pro Thr Ile Ser Phe Leu Ser Pro Val Asn
            675                 680                 685

AAT ATT ACT TTA GTT GAA GGT TAT AAT TTA CAA GTT GAA GTT AAT GCT    2112
Asn Ile Thr Leu Val Glu Gly Tyr Asn Leu Gln Val Glu Val Asn Ala
        690                 695                 700

ACT GAT GCA GAT GGA ACT ATT GAT AAT GTA AAA CTT TAT ATA GAT AAC    2160
Thr Asp Ala Asp Gly Thr Ile Asp Asn Val Lys Leu Tyr Ile Asp Asn
705                 710                 715                 720
```

FIG. 17-3

```
AAT TTA GTT AGG CAA ATA AAT TCT ACT TCA TAT AAA TGG GGC CAT TCT   2208
Asn Leu Val Arg Gln Ile Asn Ser Thr Ser Tyr Lys Trp Gly His Ser
            725                 730                 735
GAT TCT CCA AAT ACA GAT GAA CTT AAT GGT CTT ACA GAA GGA ACT TAT   2256
Asp Ser Pro Asn Thr Asp Glu Leu Asn Gly Leu Thr Glu Gly Thr Tyr
            740                 745                 750
ACC TTA AAA GCA ATT GCA ACT GAT AAC GAC GGG GCT TCT ACA GAA ACG   2304
Thr Leu Lys Ala Ile Ala Thr Asp Asn Asp Gly Ala Ser Thr Glu Thr
            755                 760                 765
CAA TTT ACG TTA ACT GTA ATA ACA GAA CAA AGT CCG TCT GAG AAT TGT   2352
Gln Phe Thr Leu Thr Val Ile Thr Glu Gln Ser Pro Ser Glu Asn Cys
    770                 775                 780
GAC TTT AAT ACA CCT TCT TCA ACT GGT TTA GAA GAT TTT GAC ATT AAA   2400
Asp Phe Asn Thr Pro Ser Ser Thr Gly Leu Glu Asp Phe Asp Ile Lys
785                 790                 795                 800
AAG TTT TCT AAC GTT TTT GAG TTA GGA TCT GGC GGA CCA TCT TTA AGT   2448
Lys Phe Ser Asn Val Phe Glu Leu Gly Ser Gly Gly Pro Ser Leu Ser
            805                 810                 815
AAT TTA AAA ACA TTT ACT ATT AAT TGG AAT TCG CAA TAC AAT GGG TTA   2496
Asn Leu Lys Thr Phe Thr Ile Asn Trp Asn Ser Gln Tyr Asn Gly Leu
            820                 825                 830
TAT CAA TTT TCA ATA AAC ACA AAC AAC GGT GTA CCT GAT TAT TAT ATA   2544
Tyr Gln Phe Ser Ile Asn Thr Asn Asn Gly Val Pro Asp Tyr Tyr Ile
            835                 840                 845
AAT TTA AAA CCA AAA ATT ACC TTT CAG TTT AAA AAT GCA AAT CCA GAA   2592
Asn Leu Lys Pro Lys Ile Thr Phe Gln Phe Lys Asn Ala Asn Pro Glu
    850                 855                 860
ATA TCT ATT AGC AAT AGC TTA ATT CCT AAT TTT GAT GGT GAT TAC TGG   2640
Ile Ser Ile Ser Asn Ser Leu Ile Pro Asn Phe Asp Gly Asp Tyr Trp
865                 870                 875                 880
GTA ACA TCA GAT AAC GGT AAT TTT GTG ATG GTA TCT AAA ACT AAT AAT   2688
Val Thr Ser Asp Asn Gly Asn Phe Val Met Val Ser Lys Thr Asn Asn
                885                 890                 895
TTT ACG ATA TAC TTT AGT AAT GAC GCT ACT GCT CCT ATT TGT AAT GTT   2736
Phe Thr Ile Tyr Phe Ser Asn Asp Ala Thr Ala Pro Ile Cys Asn Val
            900                 905                 910
ACG CCT AGT AAC CAA ATA AGT AAA ATT ACT GAT GAT TCT AGT ATT AAT   2784
Thr Pro Ser Asn Gln Ile Ser Lys Ile Thr Asp Asp Ser Ser Ile Asn
            915                 920                 925
TTT AAG CTT TAC CCT AAT CCT GCT TTA GAC GAA ACT ATT TTT GTG AGC   2832
Phe Lys Leu Tyr Pro Asn Pro Ala Leu Asp Glu Thr Ile Phe Val Ser
    930                 935                 940
GCT GAA GAT GAA AAA CTA GCT TTG GTG CTT GTA CC AGT               2870
Ala Glu Asp Glu Lys Leu Ala Leu Val Leu Val Pro
945                 950                 955
```

FIG. 17-4

PYROCOCCUS FURIOSUS VC1 (7EG1)

```
ATG AGC AAG AAA AAG TTC GTC ATC GTA TCT ATC TTA ACA ATC CTT TTA    48
Met Ser Lys Lys Lys Phe Val Ile Val Ser Ile Leu Thr Ile Leu Leu
 1               5                  10                  15

GTA CAG GCA ATA TAT TTT GTA GAA AAG TAT CAT ACC TCT GAG GAC AAG    96
Val Gln Ala Ile Tyr Phe Val Glu Lys Tyr His Thr Ser Glu Asp Lys
                20                  25                  30

TCA ACT TCA AAT ACC TCA TCT ACA CCA CCC CAA ACA ACA CTT TCC ACT   144
Ser Thr Ser Asn Thr Ser Ser Thr Pro Pro Gln Thr Thr Leu Ser Thr
         35                  40                  45

ACC AAG GTT CTC AAG ATT AGA TAC CCT GAT GAC GGT GAG TGG CCA GGA   192
Thr Lys Val Leu Lys Ile Arg Tyr Pro Asp Asp Gly Glu Trp Pro Gly
     50                  55                  60

GCT CCT ATT GAT AAG GAT GGT GAT GGG AAC CCA GAA TTC TAC ATT GAA   240
Ala Pro Ile Asp Lys Asp Gly Asp Gly Asn Pro Glu Phe Tyr Ile Glu
 65                  70                  75                  80

ATA AAC CTA TGG AAC ATT CTT AAT GCT ACT GGA TTT GCT GAG ATG ACG   288
Ile Asn Leu Trp Asn Ile Leu Asn Ala Thr Gly Phe Ala Glu Met Thr
                 85                  90                  95

TAC AAT TTA ACC AGC GGC GTC CTT CAC TAC GTC CAA CAA CTT GAC AAC   336
Tyr Asn Leu Thr Ser Gly Val Leu His Tyr Val Gln Gln Leu Asp Asn
            100                 105                 110

ATT GTC TTG AGG GAT AGA AGT AAT TGG GTG CAT GGA TAC CCC GAA ATA   384
Ile Val Leu Arg Asp Arg Ser Asn Trp Val His Gly Tyr Pro Glu Ile
        115                 120                 125

TTC TAT GGA AAC AAG CCA TGG AAT GCA AAC TAC GCA ACT GAT GGC CCA   432
Phe Tyr Gly Asn Lys Pro Trp Asn Ala Asn Tyr Ala Thr Asp Gly Pro
    130                 135                 140

ATA CCA TTA CCC AGT AAA GTT TCA AAC CTA ACA GAC TTC TAT CTA ACA   480
Ile Pro Leu Pro Ser Lys Val Ser Asn Leu Thr Asp Phe Tyr Leu Thr
145                 150                 155                 160

ATC TCC TAT AAA CTT GAG CCC AAG AAC GGC CTG CCA ATT AAC TTC GCA   528
Ile Ser Tyr Lys Leu Glu Pro Lys Asn Gly Leu Pro Ile Asn Phe Ala
                165                 170                 175

ATA GAA TCC TGG TTA ACG AGA GAA GCT TGG AGA ACA ACA GGA ATT AAC   576
Ile Glu Ser Trp Leu Thr Arg Glu Ala Trp Arg Thr Thr Gly Ile Asn
            180                 185                 190

AGC GAT GAG CAA GAA GTA ATG ATA TGG ATT TAC TAT GAC GGA TTA CAA   624
Ser Asp Glu Gln Glu Val Met Ile Trp Ile Tyr Tyr Asp Gly Leu Gln
        195                 200                 205

CCG GCT GGC TCC AAA GTT AAG GAG ATT GTA GTC CCA ATA ATA GTT AAC   672
Pro Ala Gly Ser Lys Val Lys Glu Ile Val Val Pro Ile Ile Val Asn
    210                 215                 220
```

FIG. 18-1

```
GGA ACA CCA GTA AAT GCT ACA TTT GAA GTA TGG AAG GCA AAC ATT GGT      720
Gly Thr Pro Val Asn Ala Thr Phe Glu Val Trp Lys Ala Asn Ile Gly
225             230                 235                 240

TGG GAG TAT GTT GCA TTT AGA ATA AAG ACC CCA ATC AAA GAG GGA ACA      768
Trp Glu Tyr Val Ala Phe Arg Ile Lys Thr Pro Ile Lys Glu Gly Thr
                245                 250                 255

GTG ACA ATT CCA TAC GGA GCA TTT ATA AGT GTT GCA GCC AAC ATT TCA      816
Val Thr Ile Pro Tyr Gly Ala Phe Ile Ser Val Ala Ala Asn Ile Ser
                260                 265                 270

AGC TTA CCA AAT TAC ACA GAA CTT TAC TTA GAG GAC GTG GAG ATT GGA      864
Ser Leu Pro Asn Tyr Thr Glu Leu Tyr Leu Glu Asp Val Glu Ile Gly
        275                 280                 285

ACT GAG TTT GGA ACG CCA AGC ACT ACC TCC GCC CAC CTA GAG TGG TGG      912
Thr Glu Phe Gly Thr Pro Ser Thr Thr Ser Ala His Leu Glu Trp Trp
        290                 295                 300

ATC ACA AAC ATA ACA CTA ACT CCT CTA GAT AGA CCT CTT ATT TCC TAA      960
Ile Thr Asn Ile Thr Leu Thr Pro Leu Asp Arg Pro Leu Ile Ser
305                 310                 315
```

FIG. 18-2

GLYCOSIDASE ENZYMES

CROSS REFERENCES TO RELATED APPLICATIONS

This application is a divisional of U.S. patent application Ser. No. 13/548,583, filed on Jul. 13, 2012; which is a divisional of U.S. patent application Ser. No. 13/397,026, filed Feb. 15, 2012; which is a divisional of U.S. patent application Ser. No. 12/860,691, filed Aug. 20, 2010, now U.S. Pat. No. 8,119,383; which is a divisional of U.S. patent application Ser. No. 11/866,279, filed Oct. 2, 2007; which is a divisional of U.S. patent application Ser. No. 09/134,078, filed Aug. 13, 1998, now U.S. Pat. No. 6,368,844, which is a continuation of U.S. patent application Ser. No. 08/949,026, filed Oct. 10, 1997, now abandoned, which claims priority under 35 USC §119(e)(1) of prior U.S. provisional application No. 60/056,916, filed Dec. 6, 1996, all of which are hereby incorporated by reference.

REFERENCE TO SEQUENCE LISTING SUBMITTED VIA EFS-WEB

This application is being transmitted by EFS-Web, as authorized and set forth in MPEP §502.05, including a sequence listing submitted under 37 C.F.R. §1.821 in ASCII text file (.txt) format.

BACKGROUND OF THE INVENTION

This invention relates to newly identified polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been putatively identified as glucosidases, α-galactosidases, β-galactosidases, β-mannosidases, β-mannanases, endoglucanases, and pullulanases.

The glycosidic bond of β-galactosides can be cleaved by different classes of enzymes: (i) phospho-β-galactosidases (EC3.2.1.85) are specific for a phosphorylated substrate generated via phosphoenolpyruvate phosphotransferase system (PTS)-dependent uptake; (ii) typical β-galactosidases (EC 3.2.1.23), represented by the *Escherichia coli* LacZ enzyme, which are relatively specific for β-galactosides; and (iii) β-glucosidases (EC 3.2.1.21) such as the enzymes of *Agrobacterium faecalis, Clostridium thermocellum, Pyrococcus furiosus* or *Sulfolobus solfataricus* (Day, A. G. and Withers, S. G., (1986) Purification and characterization of a β-glucosidase from *Alcaligenes faecalis*. Can. J. Biochem. Cell. Biol. 64, 914-922; Kengen, S. W. M., et al. (1993) Eur. J. Biochem., 213, 305-312; Ait, N., Cruezet, N. and Cattaneo, J. (1982) Properties of β-glucosidase purified from *Clostridium thermocellum*. J. Gen. Microbiol. 128, 569-577; Grogan, D. W. (1991) Evidence that β-galactosidase of *Sulfolobus solfataricus* is only one of several activities of a thermostable β-D-glycosidase. Appl. Environ. Microbiol. 57, 1644-1649). Members of the latter group, although highly specific with respect to the β-anomeric configuration of the glycosidic linkage, often display a rather relaxed substrate specificity and hydrolyse β-glucosides as well as β-fucosides and β-galactosides.

Generally, α-galactosidases are enzymes that catalyze the hydrolysis of galactose groups on a polysaccaride backbone or hydrolyze the cleavage of di- or oligosaccharides comprising galactose.

Generally, β-mannanases are enzymes that catalyze the hydrolysis of mannose groups internally on a polysaccaride backbone or hydrolyze the cleavage of di- or oligosaccaharides comprising mannose groups. β-mannosidases hydrolyze non-reducing, terminal mannose residues on a mannose-containing polysaccharide and the cleavage of di- or oligosaccaharides comprising mannose groups.

Guar gum is a branched galactomannan polysaccharide composed of β-1,4 linked mannose backbone with α-1,6 linked galactose sidechains. The enzymes required for the degradation of guar are β-mannanase, β-mannosidase and α-galactosidase. β-mannanase hydrolyses the mannose backbone internally and β-mannosidase hydrolyses non-reducing, terminal mannose residues, α-galactosidase hydrolyses α-linked galactose groups.

Galactomannan polysaccharides and the enzymes that degrade them have a variety of applications. Guar is commonly used as a thickening agent in food and is utilized in hydraulic fracturing in oil and gas recovery. Consequently, galactomannanases are industrially relevant for the degradation and modification of guar. Furthermore, a need exists for thermostable galactomannases that are active in extreme conditions associated with drilling and well stimulation.

There are other applications for these enzymes in various industries, such as in the beet sugar industry. 20-30% of the domestic U.S. sucrose consumption is sucrose from sugar beets. Raw beet sugar can contain a small amount of raffinose when the sugar beets are stored before processing and rotting begins to set in. Raffinose inhibits the crystallization of sucrose and also constitutes a hidden quantity of sucrose. Thus, there is merit to eliminating raffinose from raw beet sugar. α-Galactosidase has also been used as a digestive aid to break down raffinose, stachyose, and verbascose in such foods as beans and other gassy foods.

β-Galactosidases which are active and stable at high temperatures appear to be superior enzymes for the production of lactose-free dietary milk products (Chaplin, M. F. and Bucke, C. (1990) In: Enzyme Technology, pp. 159-160, Cambridge University Press, Cambridge, UK). Also, several studies have demonstrated the applicability of β-galactosidases to the enzymatic synthesis of oligosaccharides via transglycosylation reactions (Nilsson, K. G. I. (1988) Enzymatic synthesis of oligosaccharides. Trends Biotechnol. 6, 156-264; Cote, G. L. and Tao, B. Y. (1990) Oligosaccharide synthesis by enzymatic transglycosylation. Glycoconjugate J. 7, 145-162). Despite the commercial potential, only a few β-galactosidases of thermophiles have been characterized so far. Two genes reported are β-galactoside-cleaving enzymes of the hyperthermophilic bacterium *Thermotoga maritima*, one of the most thermophilic organotrophic eubacteria described to date (Huber, R., Langworthy, T. A., Konig, H., Thomm, M., Woese, C. R., Sleytr, U. B. and Stetter, K. O. (1986) T martima sp. nov. represents a new genus of unique extremely thermophilic eubacteria growing up to 90° C., Arch. Microbiol. 144, 324-333) one of the most thermophilic organotrophic eubacteria described to date. The gene products have been identified as a β-galactosidase and a β-glucosidase.

Pullulanase is well known as a debranching enzyme of pullulan and starch. The enzyme hydrolyzes α-1,6-glucosidic linkages on these polymers. Starch degradation for the production or sweeteners (glucose or maltose) is a very important industrial application of this enzyme. The degradation of starch is developed in two stages. The first stage involves the liquefaction of the substrate with α-amylase, and the second stage, or saccharification stage, is performed by β-amylase with pullulanase added as a debranching enzyme, to obtain better yields.

Endoglucanases can be used in a variety of industrial applications. For instance, the endoglucanases of the present invention can hydrolyze the internal β-1,4-glycosidic bonds in cellulose, which may be used for the conversion of plant biomass into fuels and chemicals. Endoglucanases also have applications in detergent formulations, the textile industry, in animal feed, in waste treatment, and in the fruit juice and brewing industry for the clarification and extraction of juices.

The polynucleotides and polypeptides of the present invention have been identified as glucosidases, α-galactosidases, β-galactosidases, β-mannosidases, β-mannanases, endoglucanases, and pullulanases as a result of their enzymatic activity.

In accordance with one aspect of the present invention, there are provided novel enzymes, as well as active fragments, analogs and derivatives thereof.

In accordance with another aspect of the present invention, there are provided isolated nucleic acid molecules encoding the enzymes of the present invention including mRNAs, cDNAs, genomic DNAs as well as active analogs and fragments of such enzymes.

In accordance with another aspect of the present invention there are provided isolated nucleic acid molecules encoding mature polypeptides expressed by the DNA contained in ATCC Deposit No. 97379.

In accordance with yet a further aspect of the present invention, there is provided a process for producing such polypeptides by recombinant techniques comprising culturing recombinant prokaryotic and/or eukaryotic host cells, containing a nucleic acid sequence of the present invention, under conditions promoting expression of said enzymes and subsequent recovery of said enzymes.

In accordance with yet a further aspect of the present invention, there is provided a process for utilizing such enzymes, or polynucleotides encoding such enzymes for hydrolyzing lactose to galactose and glucose for use in the food processing industry, the pharmaceutical industry, for example, to treat intolerance to lactose, as a diagnostic reporter molecule, in corn wet milling, in the fruit juice industry, in baking, in the textile industry and in the detergent industry.

In accordance with yet a further aspect of the present invention, there is provided a process for utilizing such enzymes for hydrolyzing guar gum (a galactomannan polysaccharide) to remove non-reducing terminal mannose residues. Further polysaccharides such as galactomannan and the enzymes according to the invention that degrade them have a variety of applications. Guar gum is commonly used as a thickening agent in food and also is utilized in hydraulic fracturing in oil and gas recovery. Consequently, mannanases are industrially relevant for the degradation and modification of guar gums. Furthermore, a need exists for thermostable mannases that are active in extreme conditions associated with drilling and well stimulation.

In accordance with yet a further aspect of the present invention, there are also provided nucleic acid probes comprising nucleic acid molecules of sufficient length to specifically hybridize to a nucleic acid sequence of the present invention.

In accordance with yet a further aspect of the present invention, there is provided a process for utilizing such enzymes, or polynucleotides encoding such enzymes, for in vitro purposes related to scientific research, for example, to generate probes for identifying similar sequences which might encode similar enzymes from other organisms by using certain regions, i.e., conserved sequence regions, of the nucleotide sequence.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 is an illustration of the full-length DNA (SEQ ID NO:1) and corresponding deduced amino acid sequence (SEQ ID NO:15) of M11TL-29G of the present invention. Sequencing was performed using a 378 automated DNA sequencer for all sequences of the present invention (Applied Biosystems, Inc.).

FIG. 2 is an illustration of the full-length DNA (SEQ ID NO:2) and corresponding deduced amino acid sequence (SEQ ID NO:16) of OC1/4V-33B/G.

FIG. 3 is an illustration of the full-length DNA (SEQ ID NO:3) and corresponding deduced amino acid sequence (SEQ ID NO:17) of F1-12G.

FIG. 4 are illustrations of the full-length DNA (SEQ ID NO:4) and corresponding deduced amino acid sequence (SEQ ID NO:18) of 9N2-3 1 B/G.

FIG. 5 are illustrations of the full-length DNA (SEQ ID NO:5) and corresponding deduced amino acid sequence (SEQ ID NO:19) of MSB8-6G.

FIG. 6 are illustrations of the full-length DNA (SEQ ID NO:6) and corresponding deduced amino acid sequence (SEQ ID NO:20) of AEDII12RA-18B/G.

FIG. 7 is an illustration of the full-length DNA (SEQ ID NO:7) and corresponding deduced amino acid sequence (SEQ ID NO:21) of GC74-22G.

FIG. 8 is an illustration of the full-length DNA (SEQ ID NO:8) and corresponding deduced amino acid sequence (SEQ ID NO:22) of VC1-7G1.

FIG. 9 is an illustration of the full-length DNA (SEQ ID NO:9) and corresponding deduced amino acid sequence (SEQ ID NO:23) of 37GP1.

FIG. 10 is an illustration of the full-length DNA (SEQ ID NO:10) and corresponding deduced amino acid sequence (SEQ ID NO:24) of 6GC2.

FIG. 11 is an illustration of the full-length DNA (SEQ ID NO:11) and corresponding deduced amino acid sequence (SEQ ID NO:25) of 6GP2.

FIG. 12 is an illustration of the full-length DNA (SEQ ID NO:12) and corresponding deduced amino acid sequence (SEQ ID NO:26) of 63GB1.

FIG. 13 is an illustration of the full-length DNA (SEQ ID NO:13) and corresponding deduced amino acid sequence (SEQ ID NO:27) of OC1/4V 33GP1.

FIG. 14 is an illustration of the full-length DNA (SEQ ID NO:14) and corresponding deduced amino acid sequence (SEQ ID NO:28) of 6GP3.

FIG. 15 is an illustration of the full-length DNA (SEQ ID NO:57) and corresponding deduced amino acid sequence (SEQ ID NO:61) of *Thermotoga maritima* MSB8-6GP2.

FIG. 16 is an illustration of the full-length DNA (SEQ ID NO:58) and corresponding deduced amino acid sequence (SEQ ID NO:62) of *Thermotoga maritima* MSB8-6GP4.

FIG. 17 is an illustration of the full-length DNA (SEQ ID NO:59) and corresponding deduced amino acid sequence (SEQ ID NO:63) of *Banki gouldi* 37GP4.

FIG. 18 is an illustration of the full-length DNA (SEQ ID NO:60) and corresponding deduced amino acid sequence (SEQ ID NO:64) of *Pyrococcus furiosus* VC1-7EG1.

SUMMARY OF THE INVENTION

In accordance with an aspect of the present invention, there are provided isolated nucleic acids (polynucleotides) which encode for the mature enzymes having the deduced amino acid sequences of Figures. 1-18 (SEQ ID NOS: 15-28 and 61-64).

In accordance with another aspect of the present invention, there are provided isolated polynucleotides encoding the enzymes of the present invention. The deposited material is a mixture of genomic clones comprising DNA encoding an enzyme of the present invention. Each genomic clone comprising the respective DNA has been inserted into a pBluescript vector (Stratagene, La Jolla, Calif.). The deposit has been deposited with the American Type Culture Collection, 12301 Parklawn Drive, Rockville, Md. 20852, USA, on Dec. 13, 1995 and assigned ATCC Deposit No. 97379.

The deposit(s) have been made under the terms of the Budapest Treaty on the International Recognition of the deposit of micro-organisms for purposes of patent procedure. The strains will be irrevocably and without restriction or condition released to the public upon the issuance of a patent. These deposits are provided merely as convenience to those of skill in the art and are not an admission that a deposit be required under 35 U.S.C. §112. The sequences of the polynucleotides contained in the deposited materials, as well as the amino acid sequences of the polypeptides encoded thereby, are controlling in the event of any conflict with any description of sequences herein. A license may be required to make, use or sell the deposited materials, and no such license is hereby granted.

The publications discussed herein are provided solely for their disclosure prior to the filing date of the present application. Nothing herein is to be construed as an admission that the invention is not entitled to antedate such disclosure by virtue of prior invention.

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences.

DETAILED DESCRIPTION OF THE INVENTION

The polynucleotides of this invention were originally recovered from genomic gene libraries derived from the following organisms:

M11TL is a new species of *Desulfurococcus* isolated from Diamond Pool in Yellowstone National Park. The organism grows optimally at 85-88° C., pH 7.0 in a low salt medium containing yeast extract, peptone, and gelatin as substrates with a $N_2/CO_2$ gas phase.

OC1/4V is from the genus *Thermotoga*. The organism was isolated from Yellowstone National Park. It grows optimally at 75° C. in a low salt medium with cellulose as a substrate and $N_2$ in gas phase.

*Pyrococcus furiosus* VC1 is from the genus *Pyrococcus*. VC1 was isolated from Vulcano, Italy. It grows optimally at 100° C. in a high salt medium (marine) containing elemental sulfur, yeast extract, peptone and starch as substrates and $N_2$ in gas phase.

*Staphylothermus marinus* F1 is from the genus *Staphylothermus*. F1 was isolated from Vulcano, Italy. It grows optimally at 85° C., pH 6.5 in high salt medium (marine) containing elemental sulfur and yeast extract as substrates and $N_2$ in gas phase.

*Thermococcus* 9N-2 is from the genus *Thermococcus* 9N-2 was isolated from diffuse vent fluid in the East Pacific Rise. It is a strict anaerobe that grows optimally at 87° C.

*Thermotoga maritima* MSB8 is from the genus *Thermotoga*, and was isolated from Vulcano, Italy. MSB8 grows optimally at 85° C. pH 6.5 in a high salt medium (marine) containing starch and yeast extract as substrates and $N_2$ in gas phase.

*Thermococcus alcaliphilus* AEDII12RA is from the genus *Thermococcus*. AEDII12RA grows optimally at 85° C., pH 9.5 in a high salt medium (marine) containing polysulfides and yeast extract as substrates and $N_2$ in gas phase.

*Thermococcus chitonophagus* GC74 is from the genus *Thermococcus*. GC74 grows optimally at 85° C., pH 6.0 in a high salt medium (marine) containing chitin, meat extract, elemental sulfur and yeast extract as substrates and $N_2$ in gas phase. AEPII 1a grows optimally at 85° C. at pH 6.5 in marine medium under anaerobic conditions. It has many substrates. *Bankia gouldi* is from the genus *Bankia*.

Accordingly, the polynucleotides and enzymes encoded thereby are identified by the organism from which they were isolated, and are sometimes hereinafter referred to as "M11TL" (FIG. 1 and SEQ ID NOS:1 and 15), "OC1/4V-33B/G" (FIG. 2 and SEQ ID NOS:2 and 16), "F1-12G" (FIG. 3 and SEQ ID NOS:3 and 17), "9N2-31 B/G" (FIG. 4 and SEQ ID NOS:4 and 18), "MSB8" (FIG. 5 and SEQ ID NOS:5 and 19), "AEDII12RA-18B/G" (FIG. 6 and SEQ ID NOS:6 and 20), "GC74-22G" (FIG. 7 and SEQ ID NOS:7 and 21), "VC1-7G1" (FIG. 8 and SEQ ID NOS:8 and 22), "37GP1" (FIG. 9 and SEQ ID NOS: 9 and 23), "6GC2" (FIG. 10 and SEQ ID NOS: 10 and 24), "6GP2" (FIG. 11 and SEQ ID NOS:11 and 25), "AEPII 1a" (FIG. 12 and SEQ ID NOS:12 and 26), "OC1/4V" (FIG. 13 and SEQ ID NOS:13 and 27), and "6GP3" (FIG. 14 and SEQ ID NOS:28), "MSB8-6GP2" (FIG. 15 and SEQ ID NOS:57 and 61), "MSB8-6GP4" (FIG. 16 and SEQ ID NOS:58 and 62), "VC1-7EG1" (FIG. 17 and SEQ ID NOS:59 and 63), and 37GP4 (FIG. 18 and SEQ ID NOS:60 and 64).

The polynucleotides and polypeptides of the present invention show identity at the nucleotide and protein level to known genes and proteins encoded thereby as shown in Table 1.

TABLE 1

| Clone | Gene/Protein with Closest Homology | Protein Identity | Nucleic Acid Identity |
|---|---|---|---|
| M11TL-29G (DNA SEQ ID NO: 1, Protein SEQ ID NO: 15) | Sulfolobus sulfataricus DSM 1616/P1, β- galactosidase | 51% | 55% |
| OC1/4V-33B/G (DNA SEQ ID NO: 2, Protein SEQ ID NO: 16) | Caldocellum saccharolyticum, β-glucosidase | 52% | 57% |
| Staphylothermus marinus F1-12G (DNA SEQ ID NO: 3, Protein SEQ ID NO: 17) | Bacillus polymyxa, β-galactosidase | 36% | 48% |
| Thermococcus 9N2-31B/G (DNA SEQ ID NO: 4, Protein SEQ ID NO: 18) | Sulfolobus sulfataricus ATCC 49255/MT4, β-galactosidase | 51% | 50% |
| Thermotoga maritima MSB8-6G (DNA SEQ ID NO: 5, Protein SEQ ID NO: 19) | Clostridium thermocellum bglB | 45% | 53% |
| Thermococcus AEDII12RA-18B/G (DNA SEQ ID NO: 6, Protein SEQ ID NO: 20) | Bacillus polymyxa, β-galactosidase | 34% | 48% |
| Thermococcus chitonophagus GC74-22G (DNA SEQ ID NO: 7, Protein SEQ ID NO: 21) | Sulfolobus sulfataricus ATCC 49255/MT4, β-galactosidase | 46% | 54% |
| Pyrococcus furiosus VC1-7G1 (DNA SEQ ID NO: 8, Protein SEQ ID NO: 22) | Sulfolobus sulfataricus/MT-4 β-galactosidase | 46.4% | 52.5% |
| Thermotoga maritima α-galactosidase (6GC2) (DNA SEQ ID NO: 10, Protein SEQ ID NO: 24) | Pediococcus pentosaceaus α-galactosidase | 49% | 29% |
| Thermotoga maritima β-mannanase (6GP2) (DNA SEQ ID NO: 11, Protein SEQ ID NO: 25) | Aspergillus aculeatus mannanase | 56% | 37% |
| AEPII 1a β-mannosidase (63GB1) (DNA SEQ ID NO: 12, Protein SEQ ID NO: 26) | Sulfolobus solfactaricus β-galactosidase | 78% | 56% |
| OC1/4V endoglucanase (33GP1) (DNA SEQ ID NO: 13, Protein SEQ ID NO: 27) | Clostridium thermocellum endo-1,4-β-endoglucanase | 65% | 43% |
| Thermotoga maritima pullulanase (6GP3) (DNA SEQ ID NO: 14, Protein SEQ ID NO: 28) | Caldocellum saccharolyticum α- destrom 6 glucanohydralase | 72% | 53% |
| Bankia gouldi mix Endoglucanase (37GP1) (DNA SEQ ID NO: 9, Protein SEQ ID NO: 23) | None available | | |

The polynucleotides and enzymes of the present invention show homology to each other as shown in Table 2.

TABLE 2

| Clone | Gene/Protein with Closest Homology | Protein Identity | Nucleic Acid Identity |
|---|---|---|---|
| Staphylothermus marinus F1-12G (DNA SEQ ID NO: 3, Protein SEQ ID NO: 17) | Thermococcus AEDII12RA-18B/G, β- galactosidase, glucosidase (DNA SEQ ID NO: 6, Protein SEQ ID NO: 20) | 55% | 57% |
| Thermococcus 9N2-31B/G (DNA SEQ ID NO: 4, Protein SEQ ID NO: 18) | Thermococcus chitonophagus GC74-22G-glucosidase (DNA SEQ ID NO: 7, Protein SEQ ID NO: 21) | 74% | 66% |
| Pyrococcus furiosus VC1-7G1 (DNA SEQ ID NO: 8, Protein SEQ ID NO: 22) | Pyrococcus furiosus VC1-7B/G β-galactosidase | 46.4% | 54% |

All the clones identified in Tables 1 and 2 encode polypeptides which have α-glycosidase or β-glycosidase activity.

This invention, in addition to the isolated nucleic acid molecules encoding the enzymes of the present invention, also provide substantially similar sequences. Isolated nucleic acid sequences are substantially similar if: (i) they are capable of hybridizing under conditions hereinafter described, to the polynucleotides of SEQ ID NOS: 1-14 and 57-60; (ii) or they encode DNA sequences which are degenerate to the polynucleotides of SEQ ID NOS: 1-14 and 57-60. Degenerate DNA sequences encode the amino acid sequences of SEQ ID NOS: 15-28 and 61-64, but have variations in the nucleotide coding sequences. As used herein, substantially similar refers to the sequences having similar identity to the sequences of the instant invention. The nucleotide sequences that are substantially the same can be identified by hybridization or by sequence comparison. Enzyme sequences that are substantially the same can be identified by one or more of the following: proteolytic digestion, gel electrophoresis and/or microsequencing.

One means for isolating the nucleic acid molecules encoding the enzymes of the present invention is to probe a gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated to one skilled in the art that the polynucleotides of SEQ ID NOS: 1-14 and 57-60 or fragments thereof (comprising at least 12 contiguous nucleotides), are particularly useful probes. Other particularly useful probes for this purpose are hybridizable fragments to the sequences of SEQ ID NOS: 1-14 and 57-60 (i.e., comprising at least 12 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/mL polyriboadenylic acid. Approximately $2\times10^7$ cpm (specific activity $4\text{-}9\times10^8$ cpm/ug) of $^{32}P$ end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at Tm 10° C. for the oligonucleotide probe. The membrane is then exposed to autoradiographic film for detection of hybridization signals.

Stringent conditions means hybridization will occur only if there is at least 90% identity, preferably at least 95% identity and most preferably at least 97% identity between the sequences. Further, it is understood that a section of a 100 bps sequence that is 95 bps in length has 95% identity with the 1090 bps sequence from which it is obtained. See J. Sambrook et al., *Molecular Cloning, A Laboratory Manual, 2d Ed.*, Cold Spring Harbor Laboratory (1989) which is hereby incorporated by reference in its entirety. Also, it is understood that a fragment of a 100 bps sequence that is 95 bps in length has 95% identity with the 100 bps sequence from which it is obtained.

As used herein, a first DNA (RNA) sequence is at least 70% and preferably at least 80% identical to another DNA (RNA) sequence if there is at least 70% and preferably at least a 80% or 90% identity, respectively, between the bases of the first sequence and the bases of the another sequence, when properly aligned with each other, for example when aligned by BLASTN.

"Identity" as the term is used herein, refers to a polynucleotide sequence which comprises a percentage of the same bases as a reference polynucleotide (SEQ ID NOS: 1-14 and 57-60). For example, a polynucleotide which is at least 90% identical to a reference polynucleotide, has polynucleotide bases which are identical in 90% of the bases which make up the reference polynucleotide and may have different bases in 10% of the bases which comprise that polynucleotide sequence.

The present invention relates polynucleotides which differ from the reference polynucleotide such that the changes are silent changes, for example the changes do not alter the amino acid sequence encoded by the polynucleotide. The present invention also relates to nucleotide changes which result in amino acid substitutions, additions, deletions, fusions and truncations in the polypeptide encoded by the reference polynucleotide. In a preferred aspect of the invention these polypeptides retain the same biological action as the polypeptide encoded by the reference polynucleotide.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other sources or to screen such sources for related sequences.

The polynucleotides of this invention were recovered from genomic gene libraries from the organisms listed in Table 1. For example, gene libraries can be generated in the Lambda ZAP II cloning vector (Stratagene Cloning Systems). Mass excisions can be performed on these libraries to generate libraries in the pBluescript phagemid. Libraries are thus generated and excisions performed according to the protocols/methods hereinafter described.

The excision libraries are introduced into the *E. coli* strain BW14893 F'kan1A. Expression clones are then identified using a high temperature filter assay. Expression clones encoding several glucanases and several other glycosidases are identified and repurified. The polynucleotides, and enzymes encoded thereby, of the present invention, yield the activities as described above.

The coding sequences for the enzymes of the present invention were identified by screening the genomic DNAs prepared for the clones having glucosidase or galactosidase activity.

An example of such an assay is a high temperature filter assay wherein expression clones were identified by use of high temperature filter assays using buffer Z (see recipe below) containing 1 mg/ml of the substrate 5-bromo-4-chloro-3-indolyl-β-D-glucopyranoside (XGLU) (Diagnostic Chemicals Limited or Sigma) after introducing an excision library into the *E. coli* strain BW14893 F'kan1A. Expression clones encoding XGLUases were identified and repurified from M11TL, OC 1/4V, *Pyrococcus furiosus* VC 1, Staphylothemus marinus F1, *Thermococcus* 9N-2, *Thermotoga maritima* MSB8, *Thermococcus alcaliphilus* AEDII12RA, and *Thermococcus chitonophagus* GC74.

Z-buffer: (referenced in Miller, J. H. (1992) A Short Course in Bacterial Genetics, p. 445.)

| per liter: | |
|---|---|
| $Na_2HPO_4$—$7H_2O$ | 16.1 g |
| $NaH_2PO_4$—$7H_2O$ | 5.5 g |
| KCl | 0.75 g |
| $MgSO_4$—$7H_2O$ | 0.246 g |
| β-mercaptoethanol | 2.7 ml |
| Adjust pH to 7.0 | |

High Temperature Filter Assay (1) The f factor f'kan (from *E. coli* strain CSH118)(1) was introduced into the pho-pnh-lac-strain BW14893 (2). BW13893 (2). The filamentous phage library was plated on the resulting strain, BW14893 F'kan. (Miller, J. H. (1992) A Short Course in Bacterial Genetics; Lee, K. S., Metcalf, et al., (1992) Evidence for two phosphonate degradative pathways in *Enterobacter Aerogenes*, J. Bacteriol., 174: 2501-2510.

(2) After growth on 100 mm LB plates containing 100 μg/ml ampicillin, 80 μg/ml nethicillin and 1 mM IPTG, colony lifts were performed using Millipore HATF membrane filters.

(3) The colonies transferred to the filters were lysed with chloroform vapor in 150 mm glass petri dishes.

(4) The filters were transferred to 100 mm glass petri dishes containing a piece of Whatman 3 MM filter paper saturated with buffer.

(a) when testing for galactosidase activity (XGALase), 3 MM paper was saturated with Z buffer containing 1 mg/ml XGAL (ChemBridge Corporation). After transferring filter bearing lysed colonies to the glass petri dish, placed dish in oven at 80-85° C.

(b) when testing for glucosidase (XGLUase), 3 MM paper was saturated with Z buffer containing 1 mg/ml XGLU. After transferring filter bearing lysed colonies to the glass petri dish, placed dish in oven at 80-85° C.

(5) 'Positives' were observed as blue spots on the filter membranes. Used the following filter rescue technique to retrieve plasmid from lysed positive colony. Used pasteur pipette (or glass capillary tube) to core blue spots on the filter membrane. Placed the small filter disk in an Eppendorf tube containing 20 μl water. Incubated the Eppendorf tube at 75° C. for 5 minutes followed by vortexing to elute plasmid DNA off filter. This DNA was transformed into electrocompetent *E. coli* cells DH1OB for *Thermotoga maritima* MSB8-6G (DNA SEQ ID NO:5, Protein SEQ ID NO:19), *Staphylothermus marinus* F1-12G (DNA SEQ ID NO:3, Protein SEQ ID NO:17), *Thermococcus* AEDII12RA-18B/G (DNA SEQ ID NO:6, Protein SEQ ID NO:20), *Thermococcus chitonophagus* GC74-22G (DNA SEQ ID NO:7, Protein SEQ ID NO:21), M11TL (DNA SEQ ID NO:1, Protein SEQ ID NO:15) and OC1/4V (DNA SEQ ID NO:2, Protein SEQ ID NO:16). Electrocompetent BW14893 F'kan1A *E. coli* were used for *Thermococcus* 9N2-31B/G (DNA SEQ ID NO:4, Protein SEQ ID NO:18), and *Pyrococcus furiosus* VC1-7G1 (DNA SEQ ID NO:8, Protein SEQ ID NO:22). Repeated filter-lift assay on transformation plates to identify 'positives'. Return transformation plates to 37° C. incubator after filter lift to regenerate colonies. Inoculate 3 ml LB liquid containing 100 μg/ml ampicillin with repurified positives and incubate at 37° C. overnight. Isolate plasmid DNA from these cultures and sequence plasmid insert. In some instances where the plates used for the initial colony lifts contained non-confluent colonies, a specific colony corresponding to a blue spot on the filter could be identified on a regenerated plate and repurified directly, instead of using the filter rescue technique.

Another example of such an assay is a variation of the high temperature filter assay wherein colony-laden filters are heat-killed at different temperatures (for example, 105° C. for 20 minutes) to monitor thermostability. The 3 MM paper is saturated with different buffers (i.e., 100 mM NaCl, 5 mM MgCl2, 100 mM Tris-Cl (pH 9.5)) to determine enzyme lot activity under different buffer conditions.

A β-glucosidase assay may also be employed, wherein GlcpfβNp is used as an artificial substrate (aryl-β-glucosidase). The increase in absorbance at 405 nm as a result of p-nitrophenol (pNp) liberation was followed on a Hitachi U-1100 spectrophotometer, equipped with a thermostatted cuvette holder. The assays may be performed at 80° C. or 90° C. in closed 1-ml quartz cuvette. A standard reaction mixture contains 150 mM trisodium substrate, pH 5.0 (at 80° C.), and 0.95 mM pNp derivative pNp=0.561 mM$^{-1}$ cm$^{-1}$). The reaction mixture is allowed to reach the desired temperature, after which the reaction is started by injecting an appropriate amount of enzyme (1.06 ml final volume).

1 U β-glucosidase activity is defined as that amount required to catalyze the formation of 1.0 μmol pNp/min. D-cellobiose may also be used as a substrate.

An ONPG assay for β-galactosidase activity is described by Miller, J. H. (1992) A Short Course in Bacterial Genetics and Mill, J. H. (1992) Experiments in Molecular Genetics, the contents of which are hereby incorporated by reference in their entirety.

A quantitative fluorometric assay for β-galactosidase specific activity is described by: Youngman P., (1987) Plasmid Vectors for Recovering and Exploiting Tn917 Transpositions in *Bacillus* and other Gram-Positive Bacteria. In Plasmids: A Practical approach (ed. K. Hardy) pp 79-103. IRL Press, Oxford. A description of the procedure can be found in Miller (1992) p. 75-77, the contents of which are incorporated by reference herein in their entirety.

The polynucleotides of the present invention may be in the form of DNA which DNA includes cDNA, genomic DNA, and synthetic DNA. The DNA may be double-stranded or single-stranded, and if single stranded may be the coding strand or non-coding (anti-sense) strand. The coding sequences which encodes the mature enzymes may be identical to the coding sequences shown in FIGS. 1-18 (SEQ ID NOS: 1-14 and 57-60) or may be a different coding sequence which coding sequence, as a result of the redundancy or degeneracy of the genetic code, encodes the same mature enzymes as the DNA of FIGS. 1-18 (SEQ ID NOS: 1-14 and 57-60).

The polynucleotide which encodes for the mature enzyme of FIGS. 1-18 (SEQ ID NOS: 15-28 and 61-64) may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence.

The present invention further relates to variants of the hereinabove described polynucleotides which encode for fragments, analogs and derivatives of the enzymes having the deduced amino acid sequences of FIGS. 1-18 (SEQ ID NOS: 15-28 and 61-64). The variant of the polynucleotide may be a naturally occurring allelic variant of the polynucleotide or a non-naturally occurring variant of the polynucleotide.

Thus, the present invention includes polynucleotides encoding the same mature enzymes as shown in FIGS. 1-18 (SEQ ID NOS: 15-28 and 61-64) as well as variants of such polynucleotides which variants encode for a fragment, derivative or analog of the enzymes of FIGS. 1-18 (SEQ ID NOS: 15-28 and 61-64). Such nucleotide variants include deletion variants, substitution variants and addition or insertion variants.

As hereinabove indicated, the polynucleotides may have a coding sequence which is a naturally occurring allelic variant of the coding sequences shown in FIGS. 1-18 (SEQ ID NOS: 1-14 and 57-60). As known in the art, an allelic variant is an alternate form of a polynucleotide sequence which may have a substitution, deletion or addition of one or more nucleotides, which does not substantially alter the function of the encoded enzyme.

Fragments of the full length gene of the present invention may be used as a hybridization probe for a cDNA or a genomic library to isolate the full length DNA and to isolate other DNAs which have a high sequence similarity to the gene or similar biological activity. Probes of this type preferably have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of genomic DNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode enzymes which either retain substantially the same biological function or activity as the mature enzyme encoded by the DNA of FIGS. 1-18 (SEQ ID NOS: 1-14 and 57-60).

Alternatively, the polynucleotide may have at least 15 bases, preferably at least 30 bases, and more preferably at least 50 bases which hybridize to any part of a polynucleotide of the present invention and which has an identity thereto, as hereinabove described, and which may or may not retain activity. For example, such polynucleotides may be employed as probes for the polynucleotides of SEQ ID NOS: 1-14 and 57-60, for example, for recovery of the polynucleotide or as a diagnostic probe or as a PCR primer.

Thus, the present invention is directed to polynucleotides having at least a 70% identity, preferably at least 90% identity and more preferably at least a 95% identity to a polynucleotide which encodes the enzymes of SEQ ID NOS: 15-28 and 61-64 as well as fragments thereof, which fragments have at least 15 bases, preferably at least 30 bases and most preferably at least 50 bases, which fragments are at least 90% identical, preferably at least 95% identical and most preferably at least 97% identical under stringent conditions to any portion of a polynucleotide of the present invention.

The present invention further relates to enzymes which have the deduced amino acid sequences of FIGS. 1-18 (SEQ ID NOS: 15-28 and 61-64) as well as fragments, analogs and derivatives of such enzyme.

The terms "fragment," "derivative" and "analog" when referring to the enzymes of FIGS. 1-18 (SEQ ID NOS: 15-28 and 61-64) means enzymes which retain essentially the same biological function or activity as such enzymes. Thus, an analog includes a proprotein which can be activated by cleavage of the proprotein portion to produce an active mature enzyme.

The enzymes of the present invention may be a recombinant enzyme, a natural enzyme or a synthetic enzyme, preferably a recombinant enzyme.

The fragment, derivative or analog of the enzymes of FIGS. 1-18 (SEQ ID NOS: 15-28 and 61-64) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzymes and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector anchor such polynucleotides or enzymes could be part of a composition, and still be isolated in that such vector or composition is not part of its natural environment.

The enzymes of the present invention include the enzymes of SEQ ID NOS: 15-28 and 61-64 (in particular the mature enzyme) as well as enzymes which have at least 70% similarity (preferably at least 70% identity) to the enzymes of SEQ ID NOS: 15-28 and 61-64 and more preferably at least 90% similarity (more preferably at least 90% identity) to the enzymes of SEQ ID NOS: 15-28 and 61-64 and still more preferably at least 95% similarity (still more preferably at least 95% identity) to the enzymes of SEQ ID NOS: 15-28 and 61-64 and also include portions of such enzymes with such portion of the enzyme generally containing at least 30 amino acids and more preferably at least 50 amino acids.

As known in the art "similarity" between two enzymes is determined by comparing the amino acid sequence and its conserved amino acid substitutes of one enzyme to the sequence of a second enzyme.

A variant, i.e. a "fragment", "analog" or "derivative" polypeptide, and reference polypeptide may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Bacillus subtilis; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pD10, psiX174, pBluescript II KS; pNH8A, pNH16a, pNH18A, pNH46A (Stratagene); ptrc99a, pKK223-3, pKK233-3, pDR540, pRIT5 (Pharmacia); Eukaryotic: pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin by 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEMI (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

β-galactosidase hydrolyzes lactose to galactose and glucose. Accordingly, the OC1/4V (DNA SEQ ID NO:2, Protein SEQ ID NO:16), 9N2-31B/G (DNA SEQ ID NO:4, Protein SEQ ID NO:18), AEDII12RA-18B/G (DNA SEQ ID NO:6, Protein SEQ ID NO:20) and F1-12G (DNA SEQ ID NO:3, Protein SEQ ID NO:17) enzymes may be employed in the food processing industry for the production of low lactose content milk and for the production of galactose or glucose from lactose contained in whey obtained in a large amount as a by-product in the production of cheese. Generally, it is desired that enzymes used in food processing, such as the aforementioned β-galactosidases, be stable at elevated temperatures to help prevent microbial contamination.

These enzymes may also be employed in the pharmaceutical industry. The enzymes are used to treat intolerance to lactose. In this case, a thermostable enzyme is desired, as well. Thermostable β-galactosidases also have uses in diagnostic applications, where they are employed as reporter molecules.

Glucosidases act on soluble cellooligosaccharides from the non-reducing end to give glucose as the sole product. Glucanases (endo- and exo-) act in the depolymerization of cellulose, generating more non-reducing ends (endo-glucanases, for instance, act on internal linkages yielding cellobiose, glucose and cellooligosaccharides as products). β-glucosidases are used in applications where glucose is the desired product. Accordingly, M11TL-29G (DNA SEQ ID NO:1, Protein SEQ ID NO:15), F1-12G (DNA SEQ ID NO:3, Protein SEQ ID NO:17), GC74-22G (DNA SEQ ID NO:7, Protein SEQ ID NO:21), MSB8-6G (DNA SEQ ID NO:5, Protein SEQ ID NO:19), OC1/4V 33G/B (DNA SEQ ID NO:2, Protein SEQ ID NO:16), OC1/4V 33GP1 (DNA SEQ ID NO:13, Protein SEQ ID NO:27), VC1-7G1 (DNA SEQ ID NO:8, Protein SEQ ID NO:22), 9N2-31B/G (DNA SEQ ID NO:4, Protein SEQ ID NO:18) and AEDII12RA18B/G (DNA SEQ ID NO:6, Protein SEQ ID NO:20) may be employed in a wide variety of industrial applications, including in corn wet milling for the separation of starch and gluten, in the fruit industry for clarification and equipment maintenance, in baking for viscosity reduction, in the textile industry for the processing of blue jeans, and in the detergent industry as an additive. For these and other applications, thermostable enzymes are desirable.

Antibodies generated against the enzymes corresponding to a sequence of the present invention can be obtained by direct injection of the enzymes into an animal or by administering the enzymes to an animal, preferably a nonhuman.

The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, 1975, Nature, 256:495-497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against the enzyme of the present invention may be used in screening for similar enzymes from other organisms and samples. Such screening techniques are known in the art, for example, one such screening assay is described in "Methods for Measuring Cellulase Activities", Methods in enzymology, Vol 160, pp. 87-116, which is hereby incorporated by reference in its entirety.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456-457 (1973).

Example 1

Bacterial Expression and Purification of Glucosidase Enzymes

DNA encoding the enzymes of the present invention, SEQ ID NOS: 1-14 and 57-60 were initially amplified from a pBluescript vector containing the DNA by the PCR technique using the primers noted herein. The amplified sequences were then inserted into the respective PQE vector listed beneath the primer sequences, and the enzyme was expressed according to the protocols set forth herein. The 5' and 3' primer sequences for to the respective genes are as follows:

```
Thermococcus AEDII12RA-18B/G
                                        (SEQ ID NO: 29)
5'CCGAGAATTCATTAAAGAGGAGAAATTAACTATGGTGAATGCTAT

GATTGTC 3'

SEQ ID NO: 30)
3'CGGAAGATCTTCATAGCTCCGGAAGCCCATA 5'
```

Vector: pQE12; and contains the following restriction enzyme sites 5' EcoRI and 3' Blg II.

```
OC1/4V-33B/G
                                        (SEQ ID NO: 31)
5'CCGAGAATTCATTAAAGAGGAGAAATTAACTATGATAAGAAGGTC

CGATTTTCC 3'

(SEQ ID NO: 32)
3'CGGAAGATCTTTAAGATTTTAGAAATTCCTT 5'
```

Vector: pQE12; and contains the following restriction enzyme sites 5' EcoRI and 3' Bgl II.

```
Thermococcus 9N2-31B/G
                                        (SEQ ID NO: 33)
5'CCGAGAATTCATTAAAGAGGAGAAATTAACTATG

CTACCAGAAGGCTTTCTC 3'

(SEQ ID NO: 34)
3'CGGAGGTACCTCACCCAAGTCCGAACTTCTC 5'
```

Vector: pQE30; and contains the following restriction enzyme sites 5' EcoRI and 3' KpnI.

```
Staphylothermus marinus F1-12G
                                        (SEQ ID NO: 35)
5'CCGAGAATTCATTAAAGAGGAGAAATTAACT

ATGATAAGGTTTCCTGATTAT 3'

(SEQ ID NO: 36)
3'CGGAAGATCTTTATTCGAGGTTCTTTAATCC 5'
```

Vector: pQE12; and contains the following restriction enzyme sites 5' EcoRI and 3' Bgl II.

*Thermococcus chitonophagus* GC74-22G
(SEQ ID NO: 37)
5'CCGAGAATTCATTCATTAAAGAGGAGAAATTAA

CTATGCTTCCAGGAGAACTTTCTC 3'

(SEQ ID NO: 38)
3'CGGAGGATCCCTACCCCTCCTCTAAGATCTC 5'

Vector: pQE12; and contains the following restriction enzyme sites 5' EcoRI and 3' BamHI.

M11TL
(SEQ ID NO: 39)
5'AATAATCTAGAGCATGCAATTCCCCAAA

GACTTCATGATAG 3'

(SEQ ID NO: 40)
3'AATAAAAGCTTACTGGATCAGTGTAAGATGCT 5'

Vector: pQE70; and contains the following restriction enzyme sites 5' SphI and 3' Hind III.

*Thermotoga maritima* MSB8-6G
(SEQ ID NO: 41)
5'CCGACAATTGATTAAAGAGGAGAAAATTAACTA

TGGAAAGGATCGATGAAATT 3'

(SEQ ID NO: 42)
3'CGGAGGTACCTCATGGTTTGAATCTCTTCTC 5'

Vector: pQE12; and contains the following restriction enzyme sites 5' EcoRI and 3' KpnI.

*Pyrococcus furiosus* VC1-7G1
(SEQ ID NO: 43)
5'CCGACAATTGATTAAAGAGGAGAAATTAACTAT

GTTCCCTGAAAAGTTCCTT 3'

(SEQ ID NO: 44)
3'CGGAGGTACCTCATCCCCTCAGCAATTCCTC 5'

Vector: pQE12; and contains the following restriction enzyme sites 5' EcoRI and 3' Kpn I.

*Bankia gouldi* endoglucanase (37GP1)
(SEQ ID NO: 45)
5'AATAAGGATCCGTTTAGCGACGCTCGC 3'

(SEQ ID NO: 46)
3'AATAAAAGCTTCCGGGTTGTACAGCGGTA

ATAGGC 5'

Vector: pQE52; and contains the following restriction enzyme sites 5' Bam HI and 3' Hind III.

*Thermotoga maritima* α:-galactosidase (6GC2)
(SEQ ID NO: 47)
5'TTTATTGAATTCATTAAAGAGGAGAAATT

AACTATGATCTGTGTGGAAATATTCGGAAAG 3'

(SEQ ID NO: 48)
3'TCTATAAAGCTTTCATTCTCTCTCACCC

TCTTCGTAGAAG 5'

Vector: pQET; and contains the following restriction enzyme sites 5' EcoRI and 3' Hind III.

*Thermotoga maritima* β-mannanase (6GP2)
(SEQ ID NO: 49)
5'TTTATTCAATTGATTAAAGAGGAGAAATTAAC

TATGGGGATTGGTGGCGACGAC 3'

(SEQ ID NO: 50)
3'TTTATTAAGCTTATCTTTTCATATTCACATACCTCC 5'

Vector: pQEt; and contains the following restriction enzyme sites 5' Hind III and 3' EcoRI.

AEPII 1α β-mannanase (63GB1)
(SEQ ID NO: 51)
5'TTTATTGAATTCATTAAAGAGGAGAAATTA

ACTATGCTACCAGAAGAGTTCCTATGGGGC 3'

(SEQ ID NO: 52)
3'TTATTAAGCTTCTCATCAACGGCTATGGTCTTCATTTC 5'

Vector: pQEt; and contains the following restriction enzyme sites 5' Hind III and 3' EcoRL.

0C1/4V endoglucanase (33GP1)
(SEQ ID NO: 53)
5'AAAAAACAATTGAATTCATTAAAGAGGAGAAATTA

ACTATGGTAGAAAGACACTTCAGATATGTT-CTT 3'

(SEQ ID NO: 54)
3'TTTTTCGGATCCAATTCTTCATTTACTCTTTGCCTG 5'

Vector: pQEt; and contains the following restriction enzyme sites 5' BamHI and 3' EcoRI.

*Thermotoga maritima* pullulanase (6GP3)
(SEQ ID NO: 55)
5'TTTTGGAATTCATTAAAGAGGAGAAATTAAC

TATGGAACTGATCATAGAAGGTTAC 3'

(SEQ ID NO: 56)
3'ATAAGAAGCTTTTCACTCTCTGTACAGAACGTACGC 5'

Vector: pQEt; and contains the following restriction enzyme sites 5' EcoRI and 3' Hind III.

*Thermotoga maritima* MSB8-6GP2
(SEQ ID NO: 65)
5'CCGACAATTGATTAAAGAGGAGAAATTAA

CTATGGAAAGGATCGATGAAATT 3'

(SEQ ID NO: 66)
3'CGGAGGTACCTCATGGTTTGAATCTCTTCTC 5'

Vector: pQE12; and contains the following restriction enzyme sites 5' EcoRI and 3' KpnI.

*Pyrococcus furiosus* VC1-7EG1
(SEQ ID NO: 67)
5'CCGACAATTGATTAAAGAGGAGAAATTAA

CTATGTTCCCTGAAAAGTTCCTT 3'

(SEQ ID NO: 68)
3'CGGAGGTACCTCATCCCCTCAGCAATTCCTC 5'

Vector: pQE12; and contains the following restriction enzyme sites 5' EcoRI and 3' Kpn I.

```
Bankia gouldi endoglucanase (37GP4)
                                   (SEQ ID NO: 69)
5'AATAAGGATCCGTTTAGCGACGCTCGC 3'

(SEQ ID NO: 70)
3'AATAAAAGCTTCCGGGTTGTACAGCGGTAATAGGC 5'
```

Vector: pQE52; and contains the following restriction enzyme sites 5' Bam HI and 3' Hind III.
Thermotoga maritima MSB8-6GP4
(SEQ ID NO: 71)
(SEQ ID NO: 72)
Vector: and contains the following restriction enzyme sites 5' and 3'.

The restriction enzyme sites indicated correspond to the restriction enzyme sites on the bacterial expression vector indicated for the respective gene (Qiagen, Inc. Chatsworth, Calif.). The pQE vector encodes antibiotic resistance (Amp'), a bacterial origin of replication (ori), an IPTG-regulatable promoter operator (P/O), a ribosome binding site (RBS), a 6-His tag and restriction enzyme sites.

The pQE vector was digested with the restriction enzymes indicated. The amplified sequences were ligated into the respective pQE vector and inserted in frame with the sequence encoding for the RBS. The ligation mixture was then used to transform the E. coli strain M15/pREP4 (Qiagen, Inc.) by electroporation. M15/pREP4 contains multiple copies of the plasmid pREP4, which expresses the lacd repressor and also confers kanamycin resistance (Kan'). Transformants were identified by their ability to grow on LB plates and ampicillin/kanamycin resistant colonies were selected. Plasmid DNA was isolated and confirmed by restriction analysis. Clones containing the desired constructs were grown overnight (0/N) in liquid culture in LB media supplemented with both Amp (100 ug/ml) and Kan (25 ug/ml). The 0/N culture was used to inoculate a large culture at a ratio of 1:100 to 1:250. The cells were grown to an optical density 600 ($O.D._{-600}$) of between 0.4 and 0.6. IPTG ("Isopropyl-B-D-thiogalacto pyranoside") was then added to a final concentration of 1 mM. IPTG induces by inactivating the lad repressor, clearing the P/O leading to increased gene expression. Cells were grown an extra 3 to 4 hours. Cells were then harvested by centrifugation.

The primer sequences set out above may also be employed to isolate the target gene from the deposited material by hybridization techniques described above.

Example 2

Isolation of a Selected Clone from the Deposited Genomic Clones

A clone is isolated directly by screening the deposited material using the oligonucleotide primers set forth in Example 1 for the particular gene desired to be isolated. The specific oligonucleotides are synthesized using an Applied Biosystems DNA synthesizer. The oligonucleotides are labeled with $^{32}$P-ATP using T4 polynucleotide kinase and purified according to a standard protocol (Maniatis et al., Molecular Cloning: A Laboratory Manual, Cold Spring Harbor Press, Cold Spring, N.Y., 1982). The deposited clones in the pBluescript vectors may be employed to transform bacterial hosts which are then plated on 1.5% agar plates to the density of 20,000-50,000 pfu/150 mm plate. These plates are screened using Nylon membranes according to the standard screening protocol (Stratagene, 1993). Specifically, the Nylon membrane with denatured and fixed DNA is prehybridized in 6×SSC, 20 mM $NaH_2PO_4$, 0.4% SDS, 5×Denhardt's 500 µg/ml denatured, sonicated salmon sperm DNA; and 6×SSC, 0.1% SDS. After one hour of prehybridization, the membrane is hybridized with hybridization buffer 6×SSC, 20 mM $NaH_2PO_4$, 0.4% SDS, 500 ug/ml denatured, sonicated salmon sperm DNA with 1×10$^6$ cpm/ml $^{32}$P-probe overnight at 42° C. The membrane is washed at 45-50° C. with washing buffer 6×SSC, 0.1% SDS for 20-30 minutes dried and exposed to Kodak X-ray film overnight. Positive clones are isolated and purified by secondary and tertiary screening. The purified clone is sequenced to verify its identity to the primer sequence.

Once the clone is isolated, the two oligonucleotide primers corresponding to the gene of interest are used to amplify the gene from the deposited material. A polymerase chain reaction is carried out in 25 µl of reaction mixture with 0.5 ug of the DNA of the gene of interest. The reaction mixture is 1.5-5 mM $MgCl_2$, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with the Perkin-Elmer Cetus automated thermal cycler. The amplified product is analyzed by agarose gel electrophoresis and the DNA band with expected molecular weight is excised and purified. The PCR product is verified to be the gene of interest by subcloning and sequencing the DNA product. The ends of the newly purified genes are nucleotide sequenced to identify full length sequences. Complete sequencing of full length genes is then performed by Exonuclease III digestion or primer walking.

Example 3

Screening for Galactosidase Activity

Screening procedures for ca-galactosidase protein activity may be assayed for as follows:

Substrate plates were provided by a standard plating procedure. Dilute XL1-Blue MRF E. coli host of (Stratagene Cloning Systems, La Jolla, Calif.) to $O.D._{-600}=1.0$ with NZY media. In 15 ml tubes, inoculate 200 µl diluted host cells with phage. Mix gently and incubate tubes at 37° C. for 15 min. Add approximately 3.5 ml LB top agarose (0.7%) containing 1 mM IPTG to each tube and pour onto all NYZ plate surface. Allow to cool and incubate at 37° C. overnight. The assay plates are obtained as substrate p-Nitrophenyl cc-galactosidase (Sigma) (200 mg/100 ml) (100 mM NaCl, 100 mM Potassium-Phosphate) 1% (w/v) agarose. The plaques are overlayed with nitrocellulose and incubated at 4° C. for 30 minutes whereupon the nitrocellulose is removed and overlayed onto the substrate plates. The substrate plates are then incubated at 70° C. for 20 minutes.

Example 4

Screening of Clones for Mannanase Activity

A solid phase screening assay was utilized as a primary screening method to test clones for β-mannanase activity.

A culture solution of the Y1090-E. coli host strain (Stratagene Cloning Systems, La Jolla, Calif.) was diluted to $O.D._{-600}=1.0$ with NZY media. The amplified library from Thermotoga maritima lambda gt11 library was diluted in SM (phage dilution buffer): 5×10$^7$ pfu/µl diluted 1:1000 then 1:100 to 5×10$^2$ pfu/4 Then 8 µl of phage dilution (5×10$^2$ pfu/µl) was plated in 200 µl host cells. They were then incubated in 15 ml tubes at 37° C. for 15 minutes.

Approximately 4 ml of molten, LB top agarose (0.7%) at approximately 52° C. was added to each tube and the mixture was poured onto the surface of LB agar plates. The agar plates were then incubated at 37° C. for five hours. The plates were replicated and induced with 10 mM IPTG-soaked Duralon-UV™ nylon membranes (Stratagene Cloning Systems, La Jolla, Calif.) overnight. The nylon membranes and plates were marked with a needle to keep their orientation and the nylon membranes were then removed and stored at 4° C.

An Azo-galactomannan overlay was applied to the LB plates containing the lambda plaques. The overlay contains 1% agarose, 50 mM potassium-phosphate buffer pH 7, 0.4% Azocarob-galactomannan. (Megazyme, Australia). The plates were incubated at 72° C. The Azocarob-galactomannan treated plates were observed after 4 hours then returned to incubation overnight. Putative positives were identified by clearing zones on the Azocarob-galactomannan plates. Two positive clones were observed.

The nylon membranes referred to above, which correspond to the positive clones were retrieved, oriented over the plate and the portions matching the locations of the clearing zones for positive clones were cut out. Phage was eluted from the membrane cut-out portions by soaking the individual portions in 500 µl SM (phage dilution buffer) and 25 µl CHCl$_3$.

Example 5

Screening of Clones for Mannosidase Activity

A solid phase screening assay was utilized as a primary screening method to test clones for β-mannosidase activity.

A culture solution of the Y1090-*E. coli* host strain (Stratagene Cloning Systems, La Jolla, Calif.) was diluted to O.D.$_{-600}$=1.0 with NZY media. The amplified library from AEPII 1a lambda gt11 library was diluted in SM (phage dilution buffer): 5×10$^7$ pfu/µl diluted 1:1000 then 1:100 to 5×10$^2$ pfu/µl. Then 8 µl of phage dilution (5×10$^2$ pfu/µl) was plated in 200 µl host cells. They were then incubated in 15 ml tubes at 37° C. for 15 minutes.

Approximately 4 ml of molten, LB top agarose (0.7%) at approximately 52° C. was added to each tube and the mixture was poured onto the surface of LB agar plates.

The agar plates were then incubated at 37° C. for five hours. The plates were replicated and induced with 10 mM IPTG-soaked Duralon-UV™ nylon membranes (Stratagene Cloning Systems, La Jolla, Calif.) overnight. The nylon membranes and plates were marked with a needle to keep their orientation and the nylon membranes were then removed and stored at 4° C.

A p-nitrophenyl-β-D-manno-pyranoside overlay was applied to the LB plates containing the lambda plaques. The overlay contains 1% agarose, 50 mM potassium-phosphate buffer pH 7, 0.4% p-nitrophenyl-β-D-manno-pyranoside. (Megazyme, Australia). The plates were incubated at 72° C. The p-nitrophenyl-β-D-manno-p-yranoside treated plates were observed after 4 hours then returned to incubation overnight. Putative positives were identified by clearing zones on the p-nitrophenyl-β-D-manno-pyranoside plates. Two positive clones were observed.

The nylon membranes referred to above, which correspond to the positive clones were retrieved, oriented over the plate and the portions matching the locations of the clearing zones for positive clones were cut out. Phage was eluted from the membrane cut-out portions by soaking the individual portions in 500 µl SM (phage dilution buffer) and 25 µl CHCl$_3$.

Example 6

Screening for Pullulanase Activity

Screening procedures for pullulanase protein activity may be assayed for as follows:

Substrate plates were provided by a standard plating procedure. Host cells are diluted to O.D.$_{-600}$=1.0 with NZY or appropriate media. In 15 ml tubes, inoculate 200 µl diluted host cells with phage. Mix gently and incubate tubes at 37° C. for 15 min. Add approximately 3.5 ml LB top agarose (0.7%) is added to each tube and the mixture is plated, allowed to cool, and incubated at 37° C. for about 28 hours. Overlays of 4.5 mls of the following substrate are poured:

| | 100 ml total volume |
|---|---|
| 0.5 g | Red Pullulan Red (Megazyme, Australia) |
| 1.0 g | Agarose |
| 5 ml | Buffer (Tris-HCL pH 7.2 @ 75° C.) |
| 2 ml | 5M NaCl |
| 5 ml | CaCl$_2$ (100 mM) |
| 85 ml | dH$_2$O |

Plates are cooled at room temperature, and then incubated at 75° C. for 2 hours. Positives are observed as showing substrate degradation.

Example 7

Screening for Endoglucanase Activity

Screening procedures for endoglucanase protein activity may be assayed for as follows:

1. The gene library is plated onto 6 LB/GelRite/0.1% CMC/NZY agar plates (~4,800 plaque forming units/plate) in *E. coli* host with LB agarose as top agarose. The plates are incubated at 37° C. overnight.
2. Plates are chilled at 4° C. for one hour.
3. The plates are overlayed with Duralon membranes (Stratagene) at room temperature for one hour and the membranes are oriented and lifted off the plates and stored at 4° C.
4. The top agarose layer is removed and plates are incubated at 37° C. for ~3 hours.
5. The plate surface is rinsed with NaCl.
6. The plate is stained with 0.1% Congo Red for 15 minutes.
7. The plate is destained with 1M NaCl.

What is claimed is:

1. A method of producing a recombinant polypeptide comprising an amino acid sequence having at least 75%, 80%, 85%, 90%, 95%, 97%, 99%, or 100% sequence identity to the amino acid sequence of SEQ ID NO:16; or an amino acid sequence encoded by a nucleic acid having at least 75%, 80%, 85%, 90%, 95%, 97%, 99%, or 100% sequence identity to the polynucleotide sequence of SEQ ID NO:2, wherein the polypeptide has glycosidase activity the method comprising:
   (a) providing a nucleic acid operably linked to a promoter; and
   (b) expressing the nucleic acid of (a) under conditions that allow expression of the polypeptide, thereby producing a recombinant polypeptide.

2. A method of producing a recombinant polypeptide comprising an amino acid sequence having at least 75%, 80%, 85%, 90%, 95%, 97%, 99%, or 100% sequence identity to the amino acid sequence of SEQ ID NO:16; or an amino acid sequence encoded by a nucleic acid having at least 75%, 80%, 85%, 90%, 95%, 97%, 99%, or 100% sequence identity to the polynucleotide sequence of SEQ ID NO:2, wherein the polypeptide has glycosidase activity the method comprising:
   (a) providing a nucleic acid sequence operatively linked to a heterologous regulatory sequence; and
   (b) expressing the nucleic acid of (a) under conditions that allow expression of the polypeptide, thereby producing a recombinant polypeptide.

3. A vector comprising a polynucleotide encoding the polypeptide produced by the method of claim 1 or 2 operably linked to a heterologous promoter.

* * * * *

SEQUENCE LISTING

<160> NUMBER OF SEQ ID NOS: 72

<210> SEQ ID NO 1
<211> LENGTH: 1446
<212> TYPE: DNA
<213> ORGANISM: Desulfurococcus sp.

<400> SEQUENCE: 1
ttgaaattcc ccaaagactt catgataggc tactcatctt caccgtttca atttgaagct    60

```
ggtattcccg ggtccgagga tccgaatagt gattggtggg tatgggtgca tgatccggag     120
aacacagcag ctggactagt cagcggcgat tttcccgaga acgcccagg ttactggaat     180 ttaaaccaaa atgaccacga cctggctgag aagctggggg ttaacactat tagagtaggc     240
gttgagtgga gtaggatttt tccaaagcca actttcaatg ttaaagtccc tgtagagaga     300
gatgagaacg gcagcattgt tcacgtagat gtcgatgata aagcggttga aagacttgat     360
gaattagcca acaaggaggc cgtaaaccat tacgtagaaa tgtataaaga ctgggttgaa     420
agaggtagaa aacttatact caatttatac cattggcccc tgcctctctg gcttcacaac     480
ccaatcatgg tgagaagaat gggcccggac agagcgccct caggctggct taacgaggag     540
tccgtggtgg agtttgccaa atacgccgca tacattgctt ggaaaatggg cgagctacct     600
gttatgtgga gcaccatgaa cgaacccaac gtcgtttatg agcaaggata catgttcgtt     660 aaaggggggtt tcccacccgg ctacttgagt ttggaagctg ctgataaggc caggagaaat     720
atgatccagg ctcatgcacg ggcctatgac aatattaaac gcttcagtaa gaaacctgtt     780
ggactaatat acgcttttcca atggttcgaa ctattagagg gtccagcaga agtatttgat     840
aagtttaaga gctctaagtt atactatttc acagacatag tatcgaaggg tagttcaatc     900
atcaatgttg aatacaggag agatcttgcc aataggctag actggttggg cgttaactac     960
tatagccgtt tagtctacaa aatcgtcgat gacaaaccta taatcctgca cgggtatgga    1020
ttcctttgta cacctggggg gatcagcccg gctgaaaatc cttgtagcga ttttgggtgg    1080
gaggtgtatc ctgaaggact ctacctactt ctaaaagaac tttacaaccg atacggggta    1140
gacttgatcg tgaccgagaa cggtgtttca gacagcaggg atgcgttgag accggcatac    1200
ctggtctcgc atgtttacag cgtatggaaa gccgctaacg agggcattcc cgtcaaaggc    1260
tacctccact ggagcttgac agacaattac gagtgggccc agggcttcag gcagaaattc    1320
ggtttagtca tggttgactt caaaactaag aaaaggtatc tccgcccaag cgccctagtg    1380
ttccgggaga tcgcaacgca taacggaata ccggatgagc tacagcatct tacactgatc    1440
cagtaa                                                               1446
```

<210> SEQ ID NO 2
<211> LENGTH: 1317
<212> TYPE: DNA
<213> ORGANISM: Thermotoga sp.

<400> SEQUENCE: 2

```
atgataagaa ggtccgattt tccaaaagat tttatcttcg gaacggctac ggcagcatac      60
cagattgaag gtgcagcaaa cgaagatggc agagggccat caatttggga tgtcttttca     120
cacacgcctg gcaaaaccct gaacggtgac acaggagacg ttgcgtgtga ccattatcac     180
cgatacaagg aagatatcca gctgatgaaa gaaatagggt tagacgctta caggttctct     240
atctcctggc ccagaattat gccagatggg aagaacatca accaaaaggg tgtggatttc     300
tacaacagac tcgttgatga gcttttgaag aatgatatca taccattcgt aacactctat     360
cactgggact taccctacgc acttttatgaa aaaggtggat ggcttaaccc agatatagcg     420
ctctatttca gagcatacgc aacgtttatg ttcaacgaac tcgtgatcg tgtgaaacat     480 tggattacac tgaacgaacc atggtgttct tctttctcgg ttattacac gggagagcat     540 gccccgggtc atcaaaattt acaagaagcg ataatcgcgg cgcacaacct gttgagggaa     600
catggacatg ccgtccaggc gtccagagaa gaagtaaaag atggggaagt tggcttaacc     660
```

```
aacgttgtga tgaaaataga accgggcgat gcaaaacccg aaagtttctt ggtcgcaagt    720
cttgttgata agttcgttaa tgcatggtcc catgaccctg ttgttttcgg aaaatatccc    780
gaagaagcag ttgcacttta tacggaaaaa gggttgcaag ttctcgatag cgatatgaat    840
attatttcga ctcctataga cttcttggt gtgaattatt acacaagaac acttgttgtt    900
tttgatatga acaatcctct tggattttcg tatgttcagg gagaccttcc caaaacggag    960
atgggatggg aaatctaccc gcagggatta tttgatatgc tggtctatct gaaggaaaga   1020
tataaactac cactttatat cacagagaac gggatggctg acctgataaa attggaaaac   1080
ggaagagttc atgataatta ccgaattgaa tatttggaaa agcactttga aaagcactt    1140 gaagcaatca atgcagatgt tgatttgaaa ggttacttca tttggtcttt gatggataac   1200
ttcgaatggg cgtgcggata ctccaaacgt ttcggtataa tctacgtaga ttacaatacc   1260
ccaaaaagga tattgaaaga ttcagcgatg tggttgaagg aatttctaaa atcttaa      1317
```

<210> SEQ ID NO 3
<211> LENGTH: 1266
<212> TYPE: DNA
<213> ORGANISM: Staphylothermus marinus

<400> SEQUENCE: 3

```
ttgataaggt ttcctgatta tttcttgttt ggaacagcta catcatcgca ccagatcgag     60
ggtaataaca tatttaatga ttggtgggag tgggagacta aaggcaggat taaggtgaga    120
tcgggtaagg catgtaatca ttgggaactc tataagaag acatagagct tatggctgag    180
ctgggatata atgcttatag gttctccata gagtggagta gaatatttcc cagaaaagat    240
catatagatt atgagtcgct taataagtat aaggaaatag ttaatctact tagaaaatac    300
gggatagaac ctgtaatcac tcttcaccac ttcacaaacc cgcaatggtt tatgaaaatt    360
ggtggatgga ctagggaaga gaacataaaa tattttataa aatatgtaga acttatagct    420
tccgagataa aagacgtgaa aatatggatc actattaatg aaccaataat atatgttta    480 caaggatata tttccggcga atggccacct ggaattaaaa atttaaaaat agctgatcaa    540
gtaactaaga atcttttaaa agcacataat gaagcctata atatacttca taaacacggt    600
attgtaggca tagctaaaaa catgatagca tttaaaccag gatctaatag aggaaaagac    660
attaatattt tcataaagt cgataaagca ttcaactggg gatttctcaa cggaatatta    720 agggagaac tagaaactct ccgtggaaaa taccgagttg agcccggaaa tattgatttc    780
ataggcataa actattattc atcatatatt gtaaaatata cttggaatcc ttttaaacta    840 catattaag tcgaaccatt agatacaggt ctatggacaa ctatgggtta ctgcatatat    900
cctagaggaa tatatgaagt tgtaatgaaa actcatgaga atacggcaa agaaataatc    960 attacagaga acggtgttgc agtagaaaat gatgaattaa ggattttatc cattatcagg   1020
cacttacaat acttatataa agccatgaat gaaggagcaa aggtgaaagg atatttctac   1080
tggagcttca tggataattt tgagtgggat aaaggattta accaaggtt cggactagta   1140 gaagttgatt ataagacttt tgagagaaaa cctagaaaaa gcgcatatgt atatagtcaa   1200
atagcacgta ccaagactat aagtgatgaa tacctagaaa aatatggatt aaagaacctc   1260
gaataa                                                             1266
```

<210> SEQ ID NO 4
<211> LENGTH: 1530
<212> TYPE: DNA
<213> ORGANISM: Thermococcus sp.

```
<400> SEQUENCE: 4
atgctaccag aaggctttct ctggggcgtg tcccagtccg ctttcagtt cgagatgggc      60 gacaagctca ggaggaacat tgatccgaac acagactggt ggaagtgggt cagggatccc     120
ttcaacataa agagggaact cgtcagcggc gacctgcccg aggaggggat aaacaactac     180
gaactttacg agaaggatca ccgcctcgcc agagacctcg gtctgaacgt ttacaggatt     240
ggaatagagt ggagcaggat ctttccctgg ccaacgtggt tgtggaggt tgacgttgag      300 cgggacagct acggactcgt gaaggacgtc aaaatcgata agacacgct cgaagagctc      360 gacgagatag cgaatcatca ggagatagcc tactaccgcc gcgttataga gcacctcagg     420
gagctgggct tcaaggtcat cgtgaacctc aaccacttca cgctcccct ctggcttcac      480 gatccgataa tcgcgaggga aaggcccctc accaacggta ggattggctg gtcgggcag      540 gagagcgtgg tggagttcgc caagtacgcg gcgtacatcg cgaacgcact cggggacctc     600
gttgatatgt ggagcaccct caacgagccg atggtcgttg tggagctcgg ttacctcgcg     660
ccctactccg gctttccgcc gggggttatg aaccccgagg cggcaaagct ggcaatcctc     720
aacatgataa acgcccacgc actggcctac aagatgataa agaagttcga cagggtaaag     780
gccgataagg attcccgctc cgaggccgag gtcgggataa tctacaacaa cataggcgtt     840
gcctatccat acgactccaa cgacccaaag gacgtgaaag ctgcagaaaa cgacaactac     900
ttccacagcg ggctcttctt cgacgcaatc cacaagggca agctcaacat cgagttcgac     960
ggtgagacct tcgtcaaagt tcggcatctc aggggggaacg actggatagg cgttaactac    1020
tacacgagag aagtcgtcag gtattcggag cccaagttcc cgagcatacc cctgatatcc    1080
ttccggggag ttcacaacta cggctacgcc tgcaggcccg ggagttcttc cgccgacgga    1140
aggcccgtaa gcgacatcgg ctgggagatc tatccggagg ggatctacga ctcgataaga    1200
gaggccaaca atacggggt cccggtttac gtcaccgaaa acggaatagc cgattcaact    1260
gacaccctgc ggccgtacta cctcgcgagc catgtagcga agattgagga ggcgtacgag    1320
gcgggttacg acgtcagggg ctacctctac tgggcgctga ccgacaacta cgagtgggcc    1380
ctcggtttca ggatgaggtt cggcctctat aaagtggatc tcataaccaa ggagagaaca    1440
ccgcgggagg aaagcgtaaa ggtttatagg ggcatcgtgg agaacaacgg agtgagcaag    1500
gaaatccggg agaagttcgg acttgggtga                                      1530

<210> SEQ ID NO 5
<211> LENGTH: 2166
<212> TYPE: DNA
<213> ORGANISM: Thermotoga maritima

<400> SEQUENCE: 5
atggaaagga tcgatgaaat tctctctcag ttaactacag aggaaaaggt gaagctcgtt      60 gtggggggttg gtcttccagg acttttttggg aacccacatt ccagagtggc gggtgcggct    120
ggagaaacac atcccgttcc aagacttgga attcctgcgt ttgtcctggc agatggtccc     180
gcaggactca gaataaaatcc cacaagggaa acgatgaaaa acacttacta cacgacggca    240
tttcccgttg aaatcatgct cgcttctacc tggaacagaa ccttctgga agaagtggga     300 aaagccatgg gagaagaagt tagggaatac ggtgtcgatg tgcttcttgc acctgcgatg     360
aacattcaca gaaaccctct tgtggaagg aatttcgagt actactcaga agatcctgtc     420 cttttccggtg aaatggcttc agcctttgtc aagggagttc aatctcaagg ggtgggagcc    480
```

```
tgcataaaac actttgtcgc gaacaaccag gaaacgaaca ggatggtagt ggacacgatc    540
gtgtccgagc gagccctcag agaaatatat ctgaaaggtt ttgaaattgc tgtcaagaaa    600
gcaagaccct ggaccgtgat gagcgcttac aacaaactga atggaaaata ctgttcacag    660
aacgaatggc ttttgaagaa ggttctcagg gaagaatggg gatttggcgg tttcgtgatg    720
agcgactggt acgcgggaga caaccctgta gaacagctca aggccggaaa cgatatgatc    780
atgcctggga aagcgtatca ggtgaacaca gaaagaagag atgaaataga gaaatcatg    840 gaggcgttga aggagggaaa attgagtgag gaggttctcg atgagtgtgt gagaaacatt    900
ctcaaagttc ttgtgaacgc gccttccttc aaagggtaca ggtactcaaa caagccggat    960
ctcgaatctc acgcggaagt cgcctacgaa gcaggtgcgg agggtgttgt ccttcttgag   1020
aacaacggtg ttcttccgtt cgatgaaaat acccatgtcg ccgtctttgg caccggtcaa   1080
atcgaaacaa taagggagg aacgggaagt ggagacaccc atccgagata cacgatctct   1140
atccttgaag gcataaaaga aagaaacatg aagttcgacg aagaactcgc ttccacttat   1200
gaggagtaca taaaaaagat gagagaaaca gaggaatata aacccagaac cgactcttgg   1260
ggaacggtca taaaaccgaa actcccagag aatttcctct cagaaaaaga gataaagaaa   1320
cctccaaaga aaaacgatgt tgcagttgtt gtgatcagta ggatctccgg tgagggatac   1380
gacagaaagc cggtgaaagg tgacttctac ctctccgatg acgagctgga actcataaaa   1440
accgtctcga aagaattcca cgatcagggt aagaaagttg tggttcttct gaacatcgga   1500
agtcccatcg aagtcgcaag ctggagagac cttgtggatg aattcttct cgtctggcag   1560 gcgggacagg agatgggaag aatagtggcc gatgttcttg tgggaaagat taatccctcc   1620
ggaaaacttc caacgacctt cccgaaggat tactcggacg ttccatcctg gacgttccca   1680
ggagagccaa aggacaatcc gcaaagagtg gtgtacgagg aagacatcta cgtgggatac   1740
aggtactacg acaccttcgg tgtggaacct gcctacgaat cggctacgg cctctcttac   1800 acaaagtttg aatacaaaga tttaaaaatc gctatcgacg tgagacgct cagagtgtcg   1860 tacacgatca caaacactgg ggacagagct ggaaaggaag tctcacaggt ctacatcaaa   1920
gctccaaaag gaaaaataga caaacccttc caggagctga aagcgtttca caaacaaaa   1980 cttttgaacc cgggtgaatc agaagaaatc tccttggaaa ttcctctcag agatcttgcg   2040
agtttcgatg ggaaagaatg ggttgtcgag tcaggagaat acgaggtcag ggtcggtgca   2100
tcttcgaggg atataaggtt gagagatatt tttctggttg agggagagaa gagattcaaa   2160
ccatga                                                              2166

<210> SEQ ID NO 6
<211> LENGTH: 1365
<212> TYPE: DNA
<213> ORGANISM: Thermococcus alcaliphilus

<400> SEQUENCE: 6
atgatccact gcccggttaa agggattata tctgaggctc gcggcataac catcacaata    60
gatttaagtt ttcaaggcca ataaataat ttggtgaatg ctatgattgt ctttccggag   120
ttcttcctct ttggaaccgc cacatcttct catcagatcg agggagataa taatggaac    180 gactggtggt attatgagga gataggtaag ctcccctaca aatccggtaa agcctgcaat    240
cactgggagc tttacaggga agatatagag ctaatggcac agctcggcta caatgcctac    300
cgcttttcga tagagtggag ccgtctcttc ccggaagagg gcaaattcaa tgaagaagcc    360
ttcaaccgct accgtgaaat aattgaaatc ctccttgaga aggggattac tccaaacgtt   420
```

```
acactgcacc acttcacatc accgctgtgg ttcatgcgga agggaggctt tttgaaggaa      480
gaaaacctca agtactggga gcagtacgtt gataaagccg cggagctcct caagggagtc      540
aagcttgtag ctacattcaa cgagccgatg gtctatgtta tgatgggcta cctcacagcc      600
tactggccgc ccttcatcaa gagtcccttt aaagccttta agttgccgc aaacctcctt      660 aaggcccatg caatggcata tgatatcctc catggtaact ttgatgtggg gatagttaaa      720
aacatcccca taatgctccc tgcaagcaac agagagaaag acgtagaagc tgcccaaaag      780
gcggataacc tctttaactg gaacttcctt gatgcaatat ggagcggaaa atataaagga      840
gcttttggaa cttacaaaac tccagaaagc gatgcagact tcatagggat aaactactac      900
acagccagcg aggtaaggca tagctggaat ccgctaaagt ttttcttcga tgccaagctt      960
gcagacttaa gcgagagaaa aacagatatg ggttggagtg tctatccaaa gggcatatac     1020
gaagctatag caaaggtttc acactacgga aagccaatgt acatcacgga aacgggata     1080 gctaccttag acgatgagtg gaggatagag tttatcatcc agcacctcca gtacgttcac     1140
aaagccttaa acgatggctt tgacttgaga ggctacttct attggtcttt tatggataac     1200
ttcgagtggg ctgagggttt tagaccacgc ttgggctgg tcgaggtgga ctacacgacc     1260 tcaagagga gaccgagaaa gagtgcttac atatatggag aaattgcaag ggaaaagaaa     1320
ataaaagacg aactgctggc aaagtatggg cttccggagc tatga                   1365

<210> SEQ ID NO 7
<211> LENGTH: 1536
<212> TYPE: DNA
<213> ORGANISM: Thermococcus chitonophagus

<400> SEQUENCE: 7
ttgcttccag agaactttct ctggggagtt tcacagtccg gattccagtt tgaaatgggg       60
gacagactga ggaggcacat tgatccaaac acagattggt ggtactgggt aagagatgaa      120
tataatatca aaaaaggact agtaagtggg gatcttcccg aagacggtat aaattcatat      180
gaattatatg agagagacca agaaattgca aaggatttag gctcaacac atataggatc      240 ggaattgaat ggagcagagt atttccatgg ccaacgactt tgtcgacgt ggagtatgaa      300 attgatgagt cttacgggtt ggtaaaggat gtgaagattt ctaaagacgc attagaaaaa      360
cttgatgaaa tcgctaacca aagggaaata atatattata ggaaccctaat aaattcccta      420 agaaagaggg gttttaaggt aatactaaac ctaaatcatt ttaccctccc aatatggctt      480
catgatccta tcgaatctag agaaaaagcc ctgaccaata agaaacgg atgggtaagc      540 gaaaggagtg ttatagagtt tgcaaaattt gccgcgtatt tagcatataa attcggagac      600
atagtagaca tgtggagcac atttaatgaa cctatggtgg tcgccgagtt ggggtattta      660
gccccatact caggattccc cccgggagtc atgaatccag aagcagcaaa gttagttatg      720
ctacatatga taaacgccca tgctttagca tataggatga taaagaaatt tgacagaaaa      780
aaagctgatc cagaatcaaa agaaccagct gaaataggaa ttatatacaa taacatcggc      840
gtcacatatc cgtttaatcc gaaagactca aaggatctac aagcatccga taatgccaat      900
ttcttccaca gtgggctatt cttaacggct atccacaggg gaaaattaaa tatcgaattt      960
gacggagaga catttgttta ccttccatat ttaaagggca atgattggct gggagtgaat     1020
tattatacaa gagaagtcgt taaataccaa gatcccatgt ttccaagtat ccctctcata     1080
agcttcaagg gcgttccaga ttatggatac ggatgtagac caggaacgac gtcaaaggac     1140
```

```
ggtaatcctg ttagtgacat tggatgggag gtatatccca aaggcatgta cgactctata    1200
gtagctgcca atgaatatgg agttcctgta tacgtaacag aaaacggaat agcagattca    1260
aaagatgtat taaggcccta ttacatcgca tctcacattg aagccatgga agaggcttac    1320
gaaaatggtt atgacgtgag aggatactta cactgggcat taaccgataa ttacgaatgg    1380
gccttagggt tcagaatgag gtttggcttg tacgaagtaa acttgataac caaagagaga    1440
aaacccagga aaaagagtgt aagagtattc agagagatag ttattaataa tgggctaaca    1500
agcaacatca ggaaagagat cttagaggag gggtag                              1536

<210> SEQ ID NO 8
<211> LENGTH: 1533
<212> TYPE: DNA
<213> ORGANISM: Pyrococcus furiosus

<400> SEQUENCE: 8
atgttccctg aaaagttcct ttgggggtgtg gcacaatcgg gttttcagtt tgaaatgggg      60
gataaactca ggaggaatat tgacactaac actgattggg ggcactgggt aagggataag    120
acaaatatag agaaggcct cgttagtgga gatcttcccg aggaggggat taacaattac     180
gagctttatg agaaggacca tgagattgca agaaagctgg gtcttaatgc ttacagaata    240
ggcatagagt ggagcagaat attcccatgg ccaacgacat ttattgatgt tgattatagc    300
tataatgaat catataacct tatagaagat gtaaagatca ccaaggacac tttggaggag    360
ttagatgaga tcgccaacaa gagggaggtg gcctactata ggtcagtcat aaacagcctg    420
aggagcaagg ggtttaaggt tatagttaat ctaaatcact tcacccttcc atattggttg    480
catgatccca ttgaggctag ggagagggcg ttaactaata gaggaacgg ctgggttaac     540 ccaagaacag ttatagagtt tgcaaagtat gccgcttaca tagcctataa gtttggagat    600
atagtggata tgtggagcac gtttaatgag cctatggtgg ttgttgagct tggctaccta    660
gccccctact ctggcttccc tccagggggtt ctaaatccag aggccgcaaa gctggcgata    720
cttcacatga taaatgcaca tgctttagct tataggcaga taaagaagtt tgacactgag    780
aaagctgata aggattctaa agagcctgca gaagttggta taatttacaa caacattgga    840
gttgcttatc ccaaggatcc gaacgattcc aaggatgtta aggcagcaga aaacgacaac    900
ttcttccact cagggctgtt cttcgaggcc atacacaaag gaaaacttaa tatagagttt    960
gacggtgaaa cgtttatatga tgccccctat ctaaagggca atgactggat aggggttaat   1020
tactacacaa gggaagtagt tacgtatcag gaaccaatgt ttccttcaat cccgctgatc    1080
acctttaagg gagttcaagg atatggctat gcctgcagac ctggaactct gtcaaaggat    1140
gacagacccg tcagcgacat aggatgggaa ctctatccag aggggatgta cgattcaata    1200
gttgaagctc acaagtacgg cgttccagtt tacgtgacgg agaacggaat agcggattca    1260
aaggacatcc taagacctta ctacatagcg agccacataa agatgataga aaggcctttt    1320
gaggatgggt atgaagttaa gggctacttc cactgggcat taactgacaa cttcgagtgg    1380
gctctcgggt ttagaatgcg ctttggcctc tacgaagtca acctaattac aaaggagaga    1440
attcccaggg agaagagcgt gtcgatattc agagagatag tagccaataa tggtgttacg    1500
aaaaagattg aagaggaatt gctgagggga tga                                  1533

<210> SEQ ID NO 9
<211> LENGTH: 1614
<212> TYPE: DNA
<213> ORGANISM: Bankia gouldi
```

<400> SEQUENCE: 9

```
atgagaatac gtttagcgac gctcgcgctc tgcgcagcgc tgagcccagt caccttttgca      60
gataatgtaa ccgtacaaat cgacgccgac ggcggtaaaa aactcatcag ccgagcccctt     120
tacggcatga ataactccaa cgcagaaagc cttaccgata ctgactggca gcgttttcgc     180
gatgcaggtg tgcgcatgct gcgggaaaat ggcggcaaca acagcaccaa atataactgg     240
caactgcacc tgagcagtca tccggattgg tacaacaatg tctacgccgg caacaacaac     300
tgggacaacc gggtagccct gattcaggaa aacctgcccg gcgccgacac catgtgggca     360
ttccagctca tcggtaaggt cgcggcgact tctgcctaca actttaacga ttgggaattc     420
aaccagtcgc aatggtggac cggcgtcgct cagaatctcg ctggcggcgg tgaacccaat     480
ctggacggcg gcgcgaagc gctggttgaa ggagacccca atctctacct catggattgg     540
tcgccagccg acactgtggg tattctcgac cactggtttg gcgtaaacgg gctgggcgtg     600
cggcgtggca agccaaata ctggagtatg gataacgagc ccggcatctg ggttggcacc     660
cacgacgatg tagtgaaaga acaaacgccg gtagaagatt tcctgcacac ctatttcgaa     720
accgccaaaa aagcccgcgc caaatttccc ggtattaaaa tcaccggtcc ggtgcccgct     780
aatgagtggc agtggtatgc ctggggcggt ttctcggtac cccaggaaca agggtttatg     840
agctggatgg agtatttcat caagcgggtg tctgaagagc aacgcgcaag tggtgttcgc     900
ctcctcgatg tactcgatct gcactactac cccggcgctt acaatgcgga agatatcgtg     960
caattacatc gcacgttctt cgaccgcgac tttgtttcac tggatgccaa cggggtgaaa    1020
atggtagaag gtggctggga tgacagcatc aacaaggaat atatttttcgg gcgagtgaac    1080
gattggctcg aggaatatat ggggccagac catggtgtaa ccctgggctt aaccgaaatg    1140
tgcgtgcgca atgtgaatcc gatgactacc gccatctggt atgcctccat gctcggcacc    1200
ttcgcggata acggcgtcga atattcacc ccatggtgct ggaacaccgg aatgtgggaa    1260
acactccacc tcttcagccg ctacaacaaa ccttatcggg tcgcctccag ctccagtctt    1320
gaagagtttg tcagcgccta cagctccatt aacgaagcag aagacgccat gacggtactt    1380
ctggtgaatc gttccactag cgagacccac accgccactg tcgctatcga cgatttccca    1440
ctggatggcc cctaccgcac cctgcgctta cacaacctgc cggggaggaa aaccttcgta    1500
tctcaccgag acaacgccct ggaaaaaggt acagtgcgcg ccagcgacaa tacgtaaca    1560
ctggagttgc ccctctgtc cgttactgca atattgctca aggcccggcc ctaa           1614
```

<210> SEQ ID NO 10
<211> LENGTH: 1668
<212> TYPE: DNA
<213> ORGANISM: Thermotoga maritima

<400> SEQUENCE: 10

```
gtgatctgtg tggaaatatt cggaaagacc ttcagagagg gaagattcgt tctcaaagag      60
aaaaacttca cagttgagtt cgcggtggag aagatacacc ttggctggaa gatctccggc     120
agggtgaagg gaagtccggg aaggcttgag gttcttcgaa cgaaagcacc ggaaaaggta     180
cttgtgaaca actggcagtc ctgggaccg tgcaggtgg tcgatgcctt ttctttcaaa      240
ccacctgaaa tagatccgaa ctggagatac accgcttcgg tggtgcccga tgtacttgaa     300
aggaaccctcc agagcgacta tttcgtggct gaagaaggaa aagtgtacgg ttttctgagt     360
tcgaaaatcg cacatccttt cttcgctgtg gaagatgggg aacttgtggc atacctcgaa     420
```

-continued

| | |
|---|---|
| tatttcgatg tcgagttcga cgactttgtt cctcttgaac ctctcgttgt actcgaggat | 480 |
| cccaacacac cccttcttct ggagaaatac gcggaactcg tcggaatgga aaacaacgcg | 540 |
| agagttccaa aacacacacc cactggatgg tgcagctggt accattactt ccttgatctc | 600 |
| acctgggaag agaccctcaa gaacctgaag ctcgcgaaga atttcccgtt cgaggtcttc | 660 |
| cagatagacg acgcctacga aaaggacata ggtgactggc tcgtgacaag aggagacttt | 720 |
| ccatcggtgg aagagatggc aaaagttata gcggaaaacg gtttcatccc gggcatatgg | 780 |
| accgccccgt tcagtgtttc tgaaacctcg gatgtattca acgaacatcc ggactgggta | 840 |
| gtgaaggaaa acgagagcc gaagatggct tacagaaact ggaacaaaaa gatatacgcc | 900 |
| ctcgatcttt cgaaagatga ggttctgaac tggcttttcg atctcttctc atctctgaga | 960 |
| aagatgggct acaggtactt caagatcgac tttctcttcg cgggtgccgt tccaggagaa | 1020 |
| agaaaaaaga acataacacc aattcaggcg ttcagaaaag ggattgagac gatcagaaaa | 1080 |
| gcggtgggag aagattcttt catcctcgga tgcggctctc cccttcttcc cgcagtggga | 1140 |
| tgcgtcgacg ggatgaggat aggacctgac actgcgccgt tctggggaga acatatagaa | 1200 |
| gacaacggag ctcccgctgc aagatgggcg ctgagaaacg ccataacgag gtacttcatg | 1260 |
| cacgacaggt tctggctgaa cgaccccgac tgtctgatac tgagagagga gaaacggat | 1320 |
| ctcacacaga aggaaaagga gctctactcg tacacgtgtg gagtgctcga caacatgatc | 1380 |
| atagaaagcg atgatctctc gctcgtcaga gatcatggaa aaaaggttct gaaagaaacg | 1440 |
| ctcgaactcc tcggtggaag accacggggtt caaaacatca tgtcggagga tctgagatac | 1500 |
| gagatcgtct cgtctggcac tctctcagga aacgtcaaga tcgtggtcga tctgaacagc | 1560 |
| agagagtacc acctggaaaa agaaggaaag tcctcccctga aaaaaagagt cgtcaaaaga | 1620 |
| gaagacggaa gaaacttcta cttctacgaa gagggtgaga gagaatga | 1668 |

<210> SEQ ID NO 11
<211> LENGTH: 2043
<212> TYPE: DNA
<213> ORGANISM: Thermotoga maritima

<400> SEQUENCE: 11

| | |
|---|---|
| atggggattg gtggcgacga ctcctggagc ccgtcagtat cggcggaatt cctttttattg | 60 |
| atcgttgagc tctcttttcgt tctctttgca agtgacgagt tcgtgaaagt ggaaaacgga | 120 |
| aaattcgctc tgaacggaaa agaattcaga ttcattggaa gcaacaacta ctacatgcac | 180 |
| tacaagagca acggaatgat agacagtgtt ctggagagtg ccagagacat gggtataaag | 240 |
| gtcctcagaa tctggggttt cctcgacggg gagagttact gcagagacaa gaacacctac | 300 |
| atgcatcctg agcccggtgt tttcggggtg ccagaaggaa tatcgaacgc ccagagcggt | 360 |
| ttcgaaagac tcgactacac agttgcgaaa gcgaaagaac tcggtataaa acttgtcatt | 420 |
| gttcttgtga caactggga cgacttcggt ggaatgaacc agtacgtgag gtggtttgga | 480 |
| ggaacccatc acgacgattt ctacagagat gagaagatca agaagagta caaaaagtac | 540 |
| gtctcccttc tcgtaaaacca tgtcaatacc tacacgggag ttccttacag ggaagagccc | 600 |
| accatcatgg cctgggagct tgcaaacgaa ccgcgctgtg agacgacaa atcggggaac | 660 |
| acgctcgttg agtgggtgaa ggagatgagc tcctacataa agagtctgga tcccaaccac | 720 |
| ctcgtggctg tggggacga aggattcttc agcaactacg aaggattcaa accttacggt | 780 |
| ggagaagccg agtgggccta caacggctgg tccggtgttg actggaagaa gctcccttcg | 840 |
| atagagacgg tggacttcgg cacgttccac ctctatccgt cccactgggg tgtcagtcca | 900 |

```
gagaactatg cccagtgggg agcgaagtgg atagaagacc acataaagat cgcaaaagag    960
atcggaaaac ccgttgttct ggaagaatat ggaattccaa agagtgcgcc agttaacaga   1020
acggccatct acagactctg aacgatctg gtctacgatc tcggtggaga tggagcgatg   1080
ttctggatgc tcgcgggaat cggggaaggt tcggacagag acgagagagg gtactatccg   1140
gactacgacg gtttcagaat agtgaacgac gacagtccag aagcggaact gataagagaa   1200
tacgcgaagc tgttcaacac aggtgaagac ataagagaag acacctgctc tttcatcctt   1260
ccaaaagacg gcatggagat caaaaagacc gtggaagtga gggctggtgt tttcgactac   1320
agcaacacgt ttgaaaagtt gtctgtcaaa gtcaagatc tggttttga aaatgagata    1380
gagcatctcg gatacggaat ttacggcttt gatctcgaca caacccggat cccggatgga   1440
gaacatgaaa tgttccttga aggccacttt cagggaaaaa cggtgaaaga ctctatcaaa   1500
gcgaaagtgg tgaacgaagc acggtacgtg ctcgcagagg aagttgattt tcctctctcca  1560
gaagaggtga aaaactggtg gaacagcgga acctggcagg cagagttcgg gtcacctgac   1620
attgaatgga acggtgaggt gggaaatgga gcactgcagc tgaacgtgaa actgcccgga   1680
aagagcgact gggaagaagt gagagtagca aggaagttcg aaagactctc agaatgtgag   1740
atcctcgagt acgacatcta cattccaaac gtcgagggac tcaagggaag gttgaggccg   1800
tacgcggttc tgaaccccgg ctgggtgaag ataggcctcg acatgaacaa cgcgaacgtg   1860
gaaagtgcgg agatcatcac tttcggcgga aaagagtaca aagattcca tgtaagaatt   1920
gagttcgaca aacagcggg ggtgaaagaa cttcacatag gagttgtcgg tgatcatctg    1980
aggtacgatg gaccgatttt catcgataat gtgagacttt ataaaagaac aggaggtatg   2040
tga                                                                 2043

<210> SEQ ID NO 12
<211> LENGTH: 1539
<212> TYPE: DNA
<213> ORGANISM: Thermococcus chitonophagus

<400> SEQUENCE: 12
atgctaccag aagagttcct atggggcgtt gggcagtcag gctttcagtt cgaaatgggc     60
gacaagctca ggaggcacat cgatccaaat accgactggt ggaagtgggt tcgcgatcct   120
ttcaacataa aaaaggagct tgtgagtggg gaccttcccg aggacggcat caacaactac   180
gaacttttg aaaacgatca caagctcgct aaaggccttg gactcaacgc atacaggatt    240
ggaatagagt ggagcagaat cttttccctgg ccgacgtgga cggtcgatac cgaggtcgag   300
ttcgacactt acggtttagt aaaggacgtt aagatagaca agtccaccct tgctgaactc   360
gacaggctgg ccaacaagga ggaggtaatg tactacaggc gcgttattca gcatttgagg   420
gagctcggct tcaaggtctt cgttaacctc aaccacttca cgcttccaat atggctccac   480
gacccgatag tggcaaggga aaggccctc acaaacgaca gaatcggctg ggtctcccag   540
aggacagttg ttgagtttgc caagtatgct gcttacatcg cccatgcgct cggagacctc   600
gtggacacat ggagcacctt caacgaacct atggtagttg tggagctcgg ctacctcgcc   660
ccctactcag gatttccccc gggagtcatg aaccccgagg ccgcgaagct ggcgatcctc   720
aacatgataa acgcccacgc cttggcatat aagatgataa agaggttcga caccaagaag   780
gccgatgagg atagcaagtc ccctgcggac gttggcataa tttacaacaa catcggtgtt   840
gcctacccta agacccctaa cgatcccaag gacgttaaag cagccgaaaa cgacaactac   900
```

```
ttccacagcg gactgttctt tgatgccatc cacaagggta agctcaacat agagttcgac    960
ggcgaaaact ttgtaaaagt tagacaccta aaaggcaatg actggatagg cctcaactac   1020
tacacccgcg aggttgttag atattcggag cccaagttcc caagtatacc cctcatatcc   1080
ttcaagggcg ttcccaacta cggctactcc tgcaggcccg gcacgacctc cgccgatggc   1140
atgcccgtca gcgatatcgg ctgggaagtc tatccccagg gaatctacga ctcgatagtc   1200
gaggccacca agtacagtgt tcctgtttac gtcaccgaga acggtgttgc ggattccgcg   1260
gacacgctga ggccatacta catagtcagc cacgtctcaa agatagagga agccattgag   1320
aatggatacc ccgtaaaagg ctacatgtac tgggcgctta cggataacta cgagtgggcc   1380
ctcggcttca gcatgaggtt tggtctctac aaggtcgacc tcatctccaa ggagaggatc   1440
ccgagggaga gaagcgttga gatatatcgc aggatagtgc agtccaacgg tgttcctaag   1500
gatatcaaag aggagttcct gaagggtgag agaaatga                           1539

<210> SEQ ID NO 13
<211> LENGTH: 1083
<212> TYPE: DNA
<213> ORGANISM: Thermotoga sp.

<400> SEQUENCE: 13
atggtagaaa gacacttcag atatgttctt atttgcaccc tgtttcttgt tatgctccta    60
atctcatcca ctcagtgtgg aaaaaatgaa ccaaacaaaa gagtgaatag catggaacag   120
tcagttgctg aaagtgatag caactcagca tttgaataca acaaaatggt aggtaaagga   180
gtaaatattg gaaatgcttt agaagctcct ttcgaaggag cttggggagt aagaattgag   240
gatgaatatt ttgagataat aaagaaaagg ggatttgatt ctgttaggat tcccataaga   300
tggtcagcac atatatccga aaagccacca tatgatattg acaggaattt cctcgaaaga   360
gttaaccatg ttgtcgatag ggctcttgag aataatttaa cagtaatcat caatacgcac   420
cattttgaag aactctatca agaaccggat aaatacggcg atgttttggt ggaaatttgg   480
agacagattg caaaattctt taagattac ccggaaaatc tgttctttga aatctacaac   540
gagcctgctc agaacttgac agctgaaaaa tggaacgcac tttatccaaa agtgctcaaa   600
gttatcaggg agagcaatcc aaacccggatt gtcattatcg atgctccaaa ctgggcacac   660
tatagcgcag tgagaagtct aaaattagtc aacgacaaac gcatcattgt ttccttccat   720
tactacgaac cttccaaatt cacacatcag ggtgccgaat gggttaatcc catcccacct   780
gttagggtta gtggaatgg cgaggaatgg gaaattaacc aaatcagaag tcatttcaaa   840
tacgtgagtg actgggcaaa gcaaaataac gtaccaatct ttcttggtga attcggtgct   900
tattcaaaag cagacatgga ctcaagggtt aagtggaccg aaagtgtgag aaaaatggcg   960
gaagaatttg attttcata cgcgtattgg gaattttgtg caggatttgg catatacgat  1020
agatggtctc aaaactggat cgaaccattg gcaacagctg tggttggcac aggcaaagag  1080
taa                                                                1083

<210> SEQ ID NO 14
<211> LENGTH: 2319
<212> TYPE: DNA
<213> ORGANISM: Thermotoga maritima

<400> SEQUENCE: 14
atggatctta caaaggtggg gatcatagtg aggctgaacg agtggcaggc aaaagacgtg    60
gcaaaagaca ggttcataga gataaaagac ggaaaggctg aagtgtggat actccaggga   120
```

```
gtggaagaga ttttctacga aaaaccagac acatctccca gaatcttctt cgcacaggca    180
aggtcgaaca aggtgatcga ggcttttctg accaatcctg tggatacgaa aagaaagaa     240 ctcttcaagg ttactgttga cggaaaagag attcccgtct caagagtgga aaaggccgat    300
cccacggaca tagacgtgac gaactacgtg agaatcgtcc tttctgaatc cctgaaagaa    360
gaagacctca gaaaagacgt ggaactgatc atagaaggtt acaaaccggc aagagtcatc    420
atgatggaga tcctggacga ctactattac gatggagagc tcggagccgt atattctcca    480
gagaagacga tattcagagt ctggtccccc gtttctaagt gggtaaaggt gcttctcttc    540
aaaaacggag aagacacaga accgtaccag gttgtgaaca tggaatacaa gggaaacggg    600
gtctgggaag cggttgttga aggcgatctc gacggagtgt tctacctcta tcagctggaa    660
aactacggaa agatcagaac aaccgtcgat ccttattcga aagcggttta cgcaaacagc    720
aaaaagagcg ccgttgtgaa tcttgccagg acaaacccag aaggatggga aaacgacagg    780
ggaccgaaaa tcgaaggata cgaagacgcg ataatctatg aaatacacat agcggacatc    840
acaggactcg aaaactccgg ggtaaaaaac aaaggcctct atctcgggct caccgaagaa    900
aacacgaaag gaccgggcgg tgtgacaaca ggccttttcgc accttgtgga actcggtgtt    960
acacacgttc atatacttcc tttctttgat ttctacacag gcgacgaact cgataaagat   1020
ttcgagaagt actacaactg gggttacgat ccttacctgt tcatggttcc ggagggcaga   1080
tactcaaccg atcccaaaaa cccacacacg agaatcagag aagtcaaaga atggtcaaa   1140 gcccttcaca aacacggtat aggtgtgatt atggacatgg tgttccctca cacctacggt   1200
ataggcgaac tctctgcgtt cgatcagacg gtgccgtact acttctacag aatcgacaag   1260
acaggtgcct atttgaacga aagcggatgt ggtaacgtca tcgcaagcga agacccatg   1320 atgagaaaat tcatagtcga taccgtcacc tactgggtaa aggagtatca catagacgga   1380
ttcaggttcg atcagatggg tctcatcgac aaaaagacaa tgctcgaagt cgaaagagct   1440
cttcataaaa tcgatccaac tatcattctc tacggcgaac cgtggggtgg atggggagca   1500
ccgatcaggt ttggaaagag cgatgtcgcc ggcacacacg tggcagcttt caacgatgag   1560
ttcagagacg caataagggg ttccgtgttc aacccgagcg tcaagggatt cgtcatggga   1620
ggatacggaa aggaaaccaa gatcaaaagg ggtgttgttg aagcataaa ctacgacgga   1680 aaactcatca aaagtctcgc ccttgatcca gaagaaacta taaactacgc agcgtgtcac   1740
gacaaccaca cactgtggga caagaactac cttgccgcca agctgataa gaaaaaggaa   1800 tggaccgaag aagaactgaa aaacgcccag aaactggctg gtgcgatact tctcacttct   1860
caaggtgttc ctttcctcca cggagggcag gacttctgca ggacgaagaa tttcaacgac   1920
aactcctaca cgcccctat ctcgataaac ggcttcgatt acgaaagaaa acttcagttc   1980
atagacgtgt tcaattacca caagggtctc ataaaactca gaaagaaca ccctgctttc   2040 aggctgaaaa acgctgaaga gatcaaaaaa cacctggaat ttctcccggg cgggagaaga   2100
atagttgcgt tcatgcttaa agaccacgca ggtggtgatc cctggaaaga catcgtggtg   2160
atttacaatg gaaacttaga gaagacaaca tacaaactgc cagaaggaaa atggaatgtg   2220
gttgtgaaca gccagaaagc cggaacgaaa gtgatagaaa ccgtcgaagg aacaatagaa   2280
ctcgatccgc tttccgcgta cgttctgtac agagagtga                          2319

<210> SEQ ID NO 15
<211> LENGTH: 481
<212> TYPE: PRT
```

<213> ORGANISM: Desulfurococcus sp.

<400> SEQUENCE: 15

```
Leu Lys Phe Pro Lys Asp Phe Met Ile Gly Tyr Ser Ser Ser Pro Phe
  1               5                  10                  15

Gln Phe Glu Ala Gly Ile Pro Gly Ser Glu Asp Pro Asn Ser Asp Trp
             20                  25                  30

Trp Val Trp Val His Asp Pro Glu Asn Thr Ala Ala Gly Leu Val Ser
         35                  40                  45

Gly Asp Phe Pro Glu Asn Gly Pro Gly Tyr Trp Asn Leu Asn Gln Asn
     50                  55                  60

Asp His Asp Leu Ala Glu Lys Leu Gly Val Asn Thr Ile Arg Val Gly
 65                  70                  75                  80

Val Glu Trp Ser Arg Ile Phe Pro Lys Pro Thr Phe Asn Val Lys Val
                 85                  90                  95

Pro Val Glu Arg Asp Glu Asn Gly Ser Ile Val His Val Asp Val Asp
            100                 105                 110

Asp Lys Ala Val Glu Arg Leu Asp Glu Leu Ala Asn Lys Glu Ala Val
            115                 120                 125

Asn His Tyr Val Glu Met Tyr Lys Asp Trp Val Glu Arg Gly Arg Lys
130                 135                 140

Leu Ile Leu Asn Leu Tyr His Trp Pro Leu Pro Leu Trp Leu His Asn
145                 150                 155                 160

Pro Ile Met Val Arg Arg Met Gly Pro Asp Arg Ala Pro Ser Gly Trp
                165                 170                 175

Leu Asn Glu Glu Ser Val Val Glu Phe Ala Lys Tyr Ala Ala Tyr Ile
            180                 185                 190

Ala Trp Lys Met Gly Glu Leu Pro Val Met Trp Ser Thr Met Asn Glu
        195                 200                 205

Pro Asn Val Val Tyr Glu Gln Gly Tyr Met Phe Val Lys Gly Gly Phe
    210                 215                 220

Pro Pro Gly Tyr Leu Ser Leu Glu Ala Ala Asp Lys Ala Arg Arg Asn
225                 230                 235                 240

Met Ile Gln Ala His Ala Arg Ala Tyr Asp Asn Ile Lys Arg Phe Ser
                245                 250                 255

Lys Lys Pro Val Gly Leu Ile Tyr Ala Phe Gln Trp Phe Glu Leu Leu
            260                 265                 270

Glu Gly Pro Ala Glu Val Phe Asp Lys Phe Ser Ser Lys Leu Tyr
        275                 280                 285

Tyr Phe Thr Asp Ile Val Ser Lys Gly Ser Ser Ile Ile Asn Val Glu
    290                 295                 300

Tyr Arg Arg Asp Leu Ala Asn Arg Leu Asp Trp Leu Gly Val Asn Tyr
305                 310                 315                 320

Tyr Ser Arg Leu Val Tyr Lys Ile Val Asp Asp Lys Pro Ile Ile Leu
                325                 330                 335

His Gly Tyr Gly Phe Leu Cys Thr Pro Gly Gly Ile Ser Pro Ala Glu
            340                 345                 350

Asn Pro Cys Ser Asp Phe Gly Trp Glu Val Tyr Pro Glu Gly Leu Tyr
        355                 360                 365

Leu Leu Leu Lys Glu Leu Tyr Asn Arg Tyr Gly Val Asp Leu Ile Val
    370                 375                 380

Thr Glu Asn Gly Val Ser Asp Ser Arg Asp Ala Leu Arg Pro Ala Tyr
385                 390                 395                 400
```

-continued

Leu Val Ser His Val Tyr Ser Val Trp Lys Ala Ala Asn Glu Gly Ile
                405                 410                 415

Pro Val Lys Gly Tyr Leu His Trp Ser Leu Thr Asp Asn Tyr Glu Trp
            420                 425                 430

Ala Gln Gly Phe Arg Gln Lys Phe Gly Leu Val Met Val Asp Phe Lys
        435                 440                 445

Thr Lys Lys Arg Tyr Leu Arg Pro Ser Ala Leu Val Phe Arg Glu Ile
450                 455                 460

Ala Thr His Asn Gly Ile Pro Asp Glu Leu Gln His Leu Thr Leu Ile
465                 470                 475                 480

Gln

<210> SEQ ID NO 16
<211> LENGTH: 438
<212> TYPE: PRT
<213> ORGANISM: Thermotoga sp.

<400> SEQUENCE: 16

Met Ile Arg Arg Ser Asp Phe Pro Lys Asp Phe Ile Phe Gly Thr Ala
1               5                   10                  15

Thr Ala Ala Tyr Gln Ile Glu Gly Ala Ala Asn Glu Asp Gly Arg Gly
            20                  25                  30

Pro Ser Ile Trp Asp Val Phe Ser His Thr Pro Gly Lys Thr Leu Asn
        35                  40                  45

Gly Asp Thr Gly Asp Val Ala Cys Asp His Tyr His Arg Tyr Lys Glu
    50                  55                  60

Asp Ile Gln Leu Met Lys Glu Ile Gly Leu Asp Ala Tyr Arg Phe Ser
65                  70                  75                  80

Ile Ser Trp Pro Arg Ile Met Pro Asp Gly Lys Asn Ile Asn Gln Lys
                85                  90                  95

Gly Val Asp Phe Tyr Asn Arg Leu Val Asp Glu Leu Leu Lys Asn Asp
            100                 105                 110

Ile Ile Pro Phe Val Thr Leu Tyr His Trp Asp Leu Pro Tyr Ala Leu
        115                 120                 125

Tyr Glu Lys Gly Gly Trp Leu Asn Pro Asp Ile Ala Leu Tyr Phe Arg
    130                 135                 140

Ala Tyr Ala Thr Phe Met Phe Asn Glu Leu Gly Asp Arg Val Lys His
145                 150                 155                 160

Trp Ile Thr Leu Asn Glu Pro Trp Cys Ser Ser Phe Ser Gly Tyr Tyr
                165                 170                 175

Thr Gly Glu His Ala Pro Gly His Gln Asn Leu Gln Glu Ala Ile Ile
            180                 185                 190

Ala Ala His Asn Leu Leu Arg Glu His Gly His Ala Val Gln Ala Ser
        195                 200                 205

Arg Glu Glu Val Lys Asp Gly Glu Val Gly Leu Thr Asn Val Val Met
    210                 215                 220

Lys Ile Glu Pro Gly Asp Ala Lys Pro Glu Ser Phe Leu Val Ala Ser
225                 230                 235                 240

Leu Val Asp Lys Phe Val Asn Ala Trp Ser His Asp Pro Val Val Phe
                245                 250                 255

Gly Lys Tyr Pro Glu Glu Ala Val Ala Leu Tyr Thr Glu Lys Gly Leu
            260                 265                 270

Gln Val Leu Asp Ser Asp Met Asn Ile Ile Ser Thr Pro Ile Asp Phe
        275                 280                 285

```
Phe Gly Val Asn Tyr Tyr Thr Arg Thr Leu Val Val Phe Asp Met Asn
    290                 295                 300

Asn Pro Leu Gly Phe Ser Tyr Val Gln Gly Asp Leu Pro Lys Thr Glu
305                 310                 315                 320

Met Gly Trp Glu Ile Tyr Pro Gln Gly Leu Phe Asp Met Leu Val Tyr
                325                 330                 335

Leu Lys Glu Arg Tyr Lys Leu Pro Leu Tyr Ile Thr Glu Asn Gly Met
                340                 345                 350

Ala Gly Pro Asp Lys Leu Glu Asn Gly Arg Val His Asp Asn Tyr Arg
                355                 360                 365

Ile Glu Tyr Leu Glu Lys His Phe Glu Lys Ala Leu Glu Ala Ile Asn
370                 375                 380

Ala Asp Val Asp Leu Lys Gly Tyr Phe Ile Trp Ser Leu Met Asp Asn
385                 390                 395                 400

Phe Glu Trp Ala Cys Gly Tyr Ser Lys Arg Phe Gly Ile Ile Tyr Val
                405                 410                 415

Asp Tyr Asn Thr Pro Lys Arg Ile Leu Lys Asp Ser Ala Met Trp Leu
                420                 425                 430

Lys Glu Phe Leu Lys Ser
            435

<210> SEQ ID NO 17
<211> LENGTH: 421
<212> TYPE: PRT
<213> ORGANISM: Staphylothermus marinus

<400> SEQUENCE: 17

Leu Ile Arg Phe Pro Asp Tyr Phe Leu Phe Gly Thr Ala Thr Ser Ser
1               5                   10                  15

His Gln Ile Glu Gly Asn Asn Ile Phe Asn Asp Trp Trp Glu Trp Glu
                20                  25                  30

Thr Lys Gly Arg Ile Lys Val Arg Ser Gly Lys Ala Cys Asn His Trp
            35                  40                  45

Glu Leu Tyr Lys Glu Asp Ile Glu Leu Met Ala Glu Leu Gly Tyr Asn
    50                  55                  60

Ala Tyr Arg Phe Ser Ile Glu Trp Ser Arg Ile Phe Pro Arg Lys Asp
65                  70                  75                  80

His Ile Asp Tyr Glu Ser Leu Asn Lys Tyr Lys Glu Ile Val Asn Leu
                85                  90                  95

Leu Arg Lys Tyr Gly Ile Glu Pro Val Ile Thr Leu His His Phe Thr
            100                 105                 110

Asn Pro Gln Trp Phe Met Lys Ile Gly Gly Trp Thr Arg Glu Glu Asn
        115                 120                 125

Ile Lys Tyr Phe Ile Lys Tyr Val Glu Leu Ile Ala Ser Glu Ile Lys
    130                 135                 140

Asp Val Lys Ile Trp Ile Thr Ile Asn Glu Pro Ile Ile Tyr Val Leu
145                 150                 155                 160

Gln Gly Tyr Ile Ser Gly Glu Trp Pro Pro Gly Ile Lys Asn Leu Lys
                165                 170                 175

Ile Ala Asp Gln Val Thr Lys Asn Leu Leu Lys Ala His Asn Glu Ala
            180                 185                 190

Tyr Asn Ile Leu His Lys His Gly Ile Val Gly Ile Ala Lys Asn Met
        195                 200                 205

Ile Ala Phe Lys Pro Gly Ser Asn Arg Gly Lys Asp Ile Asn Ile Tyr
    210                 215                 220
```

His Lys Val Asp Lys Ala Phe Asn Trp Gly Phe Leu Asn Gly Ile Leu
225                 230                 235                 240

Arg Gly Glu Leu Glu Thr Leu Arg Gly Lys Tyr Arg Val Glu Pro Gly
            245                 250                 255

Asn Ile Asp Phe Ile Gly Ile Asn Tyr Tyr Ser Ser Tyr Ile Val Lys
        260                 265                 270

Tyr Thr Trp Asn Pro Phe Lys Leu His Ile Lys Val Glu Pro Leu Asp
    275                 280                 285

Thr Gly Leu Trp Thr Thr Met Gly Tyr Cys Ile Tyr Pro Arg Gly Ile
290                 295                 300

Tyr Glu Val Val Met Lys Thr His Glu Lys Tyr Gly Lys Glu Ile Ile
305                 310                 315                 320

Ile Thr Glu Asn Gly Val Ala Val Glu Asn Asp Glu Leu Arg Ile Leu
                325                 330                 335

Ser Ile Ile Arg His Leu Gln Tyr Leu Tyr Lys Ala Met Asn Glu Gly
            340                 345                 350

Ala Lys Val Lys Gly Tyr Phe Tyr Trp Ser Phe Met Asp Asn Phe Glu
        355                 360                 365

Trp Asp Lys Gly Phe Asn Gln Arg Phe Gly Leu Val Glu Val Asp Tyr
    370                 375                 380

Lys Thr Phe Glu Arg Lys Pro Arg Lys Ser Ala Tyr Val Tyr Ser Gln
385                 390                 395                 400

Ile Ala Arg Thr Lys Thr Ile Ser Asp Glu Tyr Leu Glu Lys Tyr Gly
                405                 410                 415

Leu Lys Asn Leu Glu
            420

<210> SEQ ID NO 18
<211> LENGTH: 509
<212> TYPE: PRT
<213> ORGANISM: Thermococcus sp.

<400> SEQUENCE: 18

Met Leu Pro Glu Gly Phe Leu Trp Gly Val Ser Gln Ser Gly Phe Gln
1               5                   10                  15

Phe Glu Met Gly Asp Lys Leu Arg Arg Asn Ile Asp Pro Asn Thr Asp
            20                  25                  30

Trp Trp Lys Trp Val Arg Asp Pro Phe Asn Ile Lys Arg Glu Leu Val
        35                  40                  45

Ser Gly Asp Leu Pro Glu Glu Gly Ile Asn Asn Tyr Glu Leu Tyr Glu
    50                  55                  60

Lys Asp His Arg Leu Ala Arg Asp Leu Gly Leu Asn Val Tyr Arg Ile
65                  70                  75                  80

Gly Ile Glu Trp Ser Arg Ile Phe Pro Trp Pro Thr Trp Phe Val Glu
                85                  90                  95

Val Asp Val Glu Arg Asp Ser Tyr Gly Leu Val Lys Val Lys Ile
            100                 105                 110

Asp Lys Asp Thr Leu Glu Glu Leu Asp Glu Ile Ala Asn His Gln Glu
        115                 120                 125

Ile Ala Tyr Tyr Arg Arg Val Ile Glu His Leu Arg Glu Leu Gly Phe
    130                 135                 140

Lys Val Ile Val Asn Leu Asn His Phe Thr Leu Pro Leu Trp Leu His
145                 150                 155                 160

Asp Pro Ile Ile Ala Arg Glu Lys Ala Leu Thr Asn Gly Arg Ile Gly

```
            165                 170                 175
Trp Val Gly Gln Glu Ser Val Val Glu Phe Ala Lys Tyr Ala Ala Tyr
            180                 185                 190

Ile Ala Asn Ala Leu Gly Asp Leu Val Asp Met Trp Ser Thr Phe Asn
            195                 200                 205

Glu Pro Met Val Val Glu Leu Gly Tyr Leu Ala Pro Tyr Ser Gly
        210                 215                 220

Phe Pro Pro Gly Val Met Asn Pro Glu Ala Ala Lys Leu Ala Ile Leu
225                 230                 235                 240

Asn Met Ile Asn Ala His Ala Leu Ala Tyr Lys Met Ile Lys Lys Phe
                245                 250                 255

Asp Arg Val Lys Ala Asp Lys Asp Ser Arg Ser Glu Ala Glu Val Gly
            260                 265                 270

Ile Ile Tyr Asn Asn Ile Gly Val Ala Tyr Pro Tyr Asp Ser Asn Asp
            275                 280                 285

Pro Lys Asp Val Lys Ala Ala Glu Asn Asp Tyr Phe His Ser Gly
        290                 295                 300

Leu Phe Phe Asp Ala Ile His Lys Gly Lys Leu Asn Ile Glu Phe Asp
305                 310                 315                 320

Gly Glu Thr Phe Val Lys Val Arg His Leu Arg Gly Asn Asp Trp Ile
                325                 330                 335

Gly Val Asn Tyr Tyr Thr Arg Glu Val Val Arg Tyr Ser Glu Pro Lys
            340                 345                 350

Phe Pro Ser Ile Pro Leu Ile Ser Phe Arg Gly Val His Asn Tyr Gly
            355                 360                 365

Tyr Ala Cys Arg Pro Gly Ser Ser Ala Asp Gly Arg Pro Val Ser
        370                 375                 380

Asp Ile Gly Trp Glu Ile Tyr Pro Glu Gly Ile Tyr Asp Ser Ile Arg
385                 390                 395                 400

Glu Ala Asn Lys Tyr Gly Val Pro Val Tyr Val Thr Glu Asn Gly Ile
                405                 410                 415

Ala Asp Ser Thr Asp Thr Leu Arg Pro Tyr Tyr Leu Ala Ser His Val
                420                 425                 430

Ala Lys Ile Glu Glu Ala Tyr Glu Ala Gly Tyr Asp Val Arg Gly Tyr
            435                 440                 445

Leu Tyr Trp Ala Leu Thr Asp Asn Tyr Glu Trp Ala Leu Gly Phe Arg
450                 455                 460

Met Arg Phe Gly Leu Tyr Lys Val Asp Leu Ile Thr Lys Glu Arg Thr
465                 470                 475                 480

Pro Arg Glu Glu Ser Val Lys Val Tyr Arg Gly Ile Val Glu Asn Asn
                485                 490                 495

Gly Val Ser Lys Glu Ile Arg Glu Lys Phe Gly Leu Gly
            500                 505
```

<210> SEQ ID NO 19
<211> LENGTH: 721
<212> TYPE: PRT
<213> ORGANISM: Thermotoga maritima

<400> SEQUENCE: 19

```
Met Glu Arg Ile Asp Glu Ile Leu Ser Gln Leu Thr Thr Glu Glu Lys
1               5                   10                  15

Val Lys Leu Val Val Gly Val Gly Leu Pro Gly Leu Phe Gly Asn Pro
            20                  25                  30
```

```
His Ser Arg Val Ala Gly Ala Gly Glu Thr His Pro Val Pro Arg
         35                  40                 45

Leu Gly Ile Pro Ala Phe Val Leu Ala Asp Gly Pro Ala Gly Leu Arg
     50                  55                  60

Ile Asn Pro Thr Arg Glu Asn Asp Glu Asn Thr Tyr Tyr Thr Thr Ala
 65              70                  75                      80

Phe Pro Val Glu Ile Met Leu Ala Ser Thr Trp Asn Arg Asp Leu Leu
                 85                  90                  95

Glu Glu Val Gly Lys Ala Met Gly Glu Val Arg Glu Tyr Gly Val
             100                 105                 110

Asp Val Leu Leu Ala Pro Ala Met Asn Ile His Arg Asn Pro Leu Cys
             115                 120                 125

Gly Arg Asn Phe Glu Tyr Tyr Ser Glu Asp Pro Val Leu Ser Gly Glu
         130                 135                 140

Met Ala Ser Ala Phe Val Lys Gly Val Gln Ser Gln Gly Val Gly Ala
145              150                 155                     160

Cys Ile Lys His Phe Val Ala Asn Asn Gln Glu Thr Asn Arg Met Val
                 165                 170                 175

Val Asp Thr Ile Val Ser Glu Arg Ala Leu Arg Glu Ile Tyr Leu Lys
             180                 185                 190

Gly Phe Glu Ile Ala Val Lys Lys Ala Arg Pro Trp Thr Val Met Ser
         195                 200                 205

Ala Tyr Asn Lys Leu Asn Gly Lys Tyr Cys Ser Gln Asn Glu Trp Leu
         210                 215                 220

Leu Lys Lys Val Leu Arg Glu Glu Trp Gly Phe Gly Gly Phe Val Met
225              230                 235                     240

Ser Asp Trp Tyr Ala Gly Asp Asn Pro Val Glu Gln Leu Lys Ala Gly
                 245                 250                 255

Asn Asp Met Ile Met Pro Gly Lys Ala Tyr Gln Val Asn Thr Glu Arg
             260                 265                 270

Arg Asp Glu Ile Glu Glu Ile Met Glu Ala Leu Lys Glu Gly Lys Leu
         275                 280                 285

Ser Glu Glu Val Leu Asp Glu Cys Val Arg Asn Ile Leu Lys Val Leu
         290                 295                 300

Val Asn Ala Pro Ser Phe Lys Gly Tyr Arg Tyr Ser Asn Lys Pro Asp
305              310                 315                     320

Leu Glu Ser His Ala Glu Val Ala Tyr Glu Ala Gly Ala Glu Gly Val
                 325                 330                 335

Val Leu Leu Glu Asn Asn Gly Val Leu Pro Phe Asp Glu Asn Thr His
             340                 345                 350

Val Ala Val Phe Gly Thr Gly Gln Ile Glu Thr Ile Lys Gly Gly Thr
             355                 360                 365

Gly Ser Gly Asp Thr His Pro Arg Tyr Thr Ile Ser Ile Leu Glu Gly
     370                 375                 380

Ile Lys Glu Arg Asn Met Lys Phe Asp Glu Glu Leu Ala Ser Thr Tyr
385              390                 395                     400

Glu Glu Tyr Ile Lys Lys Met Arg Glu Thr Glu Glu Tyr Lys Pro Arg
                 405                 410                 415

Thr Asp Ser Trp Gly Thr Val Ile Lys Pro Lys Leu Pro Glu Asn Phe
             420                 425                 430

Leu Ser Glu Lys Glu Ile Lys Lys Pro Pro Lys Lys Asn Asp Val Ala
         435                 440                 445

Val Val Val Ile Ser Arg Ile Ser Gly Glu Gly Tyr Asp Arg Lys Pro
```

```
            450                 455                 460
Val Lys Gly Asp Phe Tyr Leu Ser Asp Asp Glu Leu Glu Leu Ile Lys
465                 470                 475                 480

Thr Val Ser Lys Glu Phe His Asp Gln Gly Lys Lys Val Val Val Leu
                485                 490                 495

Leu Asn Ile Gly Ser Pro Ile Glu Val Ala Ser Trp Arg Asp Leu Val
            500                 505                 510

Asp Gly Ile Leu Leu Val Trp Gln Ala Gly Gln Glu Met Gly Arg Ile
        515                 520                 525

Val Ala Asp Val Leu Val Gly Lys Ile Asn Pro Ser Gly Lys Leu Pro
530                 535                 540

Thr Thr Phe Pro Lys Asp Tyr Ser Asp Val Pro Ser Trp Thr Phe Pro
545                 550                 555                 560

Gly Glu Pro Lys Asp Asn Pro Gln Arg Val Val Tyr Glu Glu Asp Ile
                565                 570                 575

Tyr Val Gly Tyr Arg Tyr Tyr Asp Thr Phe Gly Val Glu Pro Ala Tyr
            580                 585                 590

Glu Phe Gly Tyr Gly Leu Ser Tyr Thr Lys Phe Glu Tyr Lys Asp Leu
        595                 600                 605

Lys Ile Ala Ile Asp Gly Glu Thr Leu Arg Val Ser Tyr Thr Ile Thr
610                 615                 620

Asn Thr Gly Asp Arg Ala Gly Lys Glu Val Ser Gln Val Tyr Ile Lys
625                 630                 635                 640

Ala Pro Lys Gly Lys Ile Asp Lys Pro Phe Gln Glu Leu Lys Ala Phe
                645                 650                 655

His Lys Thr Lys Leu Leu Asn Pro Gly Glu Ser Glu Glu Ile Ser Leu
            660                 665                 670

Glu Ile Pro Leu Arg Asp Leu Ala Ser Phe Asp Gly Lys Glu Trp Val
        675                 680                 685

Val Glu Ser Gly Glu Tyr Glu Val Arg Val Gly Ala Ser Ser Arg Asp
690                 695                 700

Ile Arg Leu Arg Asp Ile Phe Leu Val Glu Gly Glu Lys Arg Phe Lys
705                 710                 715                 720

Pro

<210> SEQ ID NO 20
<211> LENGTH: 454
<212> TYPE: PRT
<213> ORGANISM: Thermococcus alcaliphilus

<400> SEQUENCE: 20

Met Ile His Cys Pro Val Lys Gly Ile Ile Ser Glu Ala Arg Gly Ile
1               5                   10                  15

Thr Ile Thr Ile Asp Leu Ser Phe Gln Gly Gln Ile Asn Asn Leu Val
                20                  25                  30

Asn Ala Met Ile Val Phe Pro Glu Phe Phe Leu Phe Gly Thr Ala Thr
            35                  40                  45

Ser Ser His Gln Ile Glu Gly Asp Asn Lys Trp Asn Asp Trp Trp Tyr
        50                  55                  60

Tyr Glu Glu Ile Gly Lys Leu Pro Tyr Lys Ser Gly Lys Ala Cys Asn
65                  70                  75                  80

His Trp Glu Leu Tyr Arg Glu Asp Ile Glu Leu Met Ala Gln Leu Gly
                85                  90                  95

Tyr Asn Ala Tyr Arg Phe Ser Ile Glu Trp Ser Arg Leu Phe Pro Glu
```

```
                100             105             110
Glu Gly Lys Phe Asn Glu Ala Phe Asn Arg Tyr Arg Glu Ile Ile
            115             120             125
Glu Ile Leu Leu Glu Lys Gly Ile Thr Pro Asn Val Thr Leu His His
        130             135             140
Phe Thr Ser Pro Leu Trp Phe Met Arg Lys Gly Phe Leu Lys Glu
145             150             155             160
Glu Asn Leu Lys Tyr Trp Glu Gln Tyr Val Asp Lys Ala Ala Glu Leu
            165             170             175
Leu Lys Gly Val Lys Leu Val Ala Thr Phe Asn Glu Pro Met Val Tyr
        180             185             190
Val Met Met Gly Tyr Leu Thr Ala Tyr Trp Pro Pro Phe Ile Lys Ser
    195             200             205
Pro Phe Lys Ala Phe Lys Val Ala Ala Asn Leu Leu Lys Ala His Ala
    210             215             220
Met Ala Tyr Asp Ile Leu His Gly Asn Phe Asp Val Gly Ile Val Lys
225             230             235             240
Asn Ile Pro Ile Met Leu Pro Ala Ser Asn Arg Glu Lys Asp Val Glu
            245             250             255
Ala Ala Gln Lys Ala Asp Asn Leu Phe Asn Trp Asn Phe Leu Asp Ala
        260             265             270
Ile Trp Ser Gly Lys Tyr Lys Gly Ala Phe Gly Thr Tyr Lys Thr Pro
    275             280             285
Glu Ser Asp Ala Asp Phe Ile Gly Ile Asn Tyr Tyr Thr Ala Ser Glu
    290             295             300
Val Arg His Ser Trp Asn Pro Leu Lys Phe Phe Asp Ala Lys Leu
305             310             315             320
Ala Asp Leu Ser Glu Arg Lys Thr Asp Met Gly Trp Ser Val Tyr Pro
            325             330             335
Lys Gly Ile Tyr Glu Ala Ile Ala Lys Val Ser His Tyr Gly Lys Pro
        340             345             350
Met Tyr Ile Thr Glu Asn Gly Ile Ala Thr Leu Asp Asp Glu Trp Arg
    355             360             365
Ile Glu Phe Ile Ile Gln His Leu Gln Tyr Val His Lys Ala Leu Asn
    370             375             380
Asp Gly Phe Asp Leu Arg Gly Tyr Phe Tyr Trp Ser Phe Met Asp Asn
385             390             395             400
Phe Glu Trp Ala Glu Gly Phe Arg Pro Arg Phe Gly Leu Val Glu Val
            405             410             415
Asp Tyr Thr Thr Phe Lys Arg Arg Pro Arg Lys Ser Ala Tyr Ile Tyr
        420             425             430
Gly Glu Ile Ala Arg Glu Lys Lys Ile Lys Asp Glu Leu Leu Ala Lys
    435             440             445
Tyr Gly Leu Pro Glu Leu
    450

<210> SEQ ID NO 21
<211> LENGTH: 511
<212> TYPE: PRT
<213> ORGANISM: Thermococcus chitonophagus

<400> SEQUENCE: 21

Leu Leu Pro Glu Asn Phe Leu Trp Gly Val Ser Gln Ser Gly Phe Gln
1               5                   10                  15
```

```
Phe Glu Met Gly Asp Arg Leu Arg Arg His Ile Asp Pro Asn Thr Asp
             20                  25                  30

Trp Trp Tyr Trp Val Arg Asp Glu Tyr Asn Ile Lys Lys Gly Leu Val
         35                  40                  45

Ser Gly Asp Leu Pro Glu Asp Gly Ile Asn Ser Tyr Glu Leu Tyr Glu
 50                  55                  60

Arg Asp Gln Glu Ile Ala Lys Asp Leu Gly Leu Asn Thr Tyr Arg Ile
 65                  70                  75                  80

Gly Ile Glu Trp Ser Arg Val Phe Pro Trp Pro Thr Thr Phe Val Asp
                 85                  90                  95

Val Glu Tyr Glu Ile Asp Glu Ser Tyr Gly Leu Val Lys Asp Val Lys
                100                 105                 110

Ile Ser Lys Asp Ala Leu Glu Lys Leu Asp Glu Ile Ala Asn Gln Arg
            115                 120                 125

Glu Ile Ile Tyr Tyr Arg Asn Leu Ile Asn Ser Leu Arg Lys Arg Gly
            130                 135                 140

Phe Lys Val Ile Leu Asn Leu Asn His Phe Thr Leu Pro Ile Trp Leu
145                 150                 155                 160

His Asp Pro Ile Glu Ser Arg Glu Lys Ala Leu Thr Asn Lys Arg Asn
                165                 170                 175

Gly Trp Val Ser Glu Arg Ser Val Ile Glu Phe Ala Lys Phe Ala Ala
            180                 185                 190

Tyr Leu Ala Tyr Lys Phe Gly Asp Ile Val Asp Met Trp Ser Thr Phe
            195                 200                 205

Asn Glu Pro Met Val Val Ala Glu Leu Gly Tyr Leu Ala Pro Tyr Ser
210                 215                 220

Gly Phe Pro Pro Gly Val Met Asn Pro Glu Ala Ala Lys Leu Val Met
225                 230                 235                 240

Leu His Met Ile Asn Ala His Ala Leu Ala Tyr Arg Met Ile Lys Lys
                245                 250                 255

Phe Asp Arg Lys Lys Ala Asp Pro Glu Ser Lys Glu Pro Ala Glu Ile
            260                 265                 270

Gly Ile Ile Tyr Asn Asn Ile Gly Val Thr Tyr Pro Phe Asn Pro Lys
            275                 280                 285

Asp Ser Lys Asp Leu Gln Ala Ser Asp Asn Ala Asn Phe Phe His Ser
290                 295                 300

Gly Leu Phe Leu Thr Ala Ile His Arg Gly Lys Leu Asn Ile Glu Phe
305                 310                 315                 320

Asp Gly Glu Thr Phe Val Tyr Leu Pro Tyr Leu Lys Gly Asn Asp Trp
                325                 330                 335

Leu Gly Val Asn Tyr Tyr Thr Arg Glu Val Val Lys Tyr Gln Asp Pro
            340                 345                 350

Met Phe Pro Ser Ile Pro Leu Ile Ser Phe Lys Gly Val Pro Asp Tyr
            355                 360                 365

Gly Tyr Gly Cys Arg Pro Gly Thr Thr Ser Lys Asp Gly Asn Pro Val
            370                 375                 380

Ser Asp Ile Gly Trp Glu Val Tyr Pro Lys Gly Met Tyr Asp Ser Ile
385                 390                 395                 400

Val Ala Ala Asn Glu Tyr Gly Val Pro Val Tyr Val Thr Glu Asn Gly
                405                 410                 415

Ile Ala Asp Ser Lys Asp Val Leu Arg Pro Tyr Tyr Ile Ala Ser His
            420                 425                 430

Ile Glu Ala Met Glu Glu Ala Tyr Glu Asn Gly Tyr Asp Val Arg Gly
```

```
            435                 440                 445
Tyr Leu His Trp Ala Leu Thr Asp Asn Tyr Glu Trp Ala Leu Gly Phe
    450                 455                 460

Arg Met Arg Phe Gly Leu Tyr Glu Val Asn Leu Ile Thr Lys Glu Arg
465                 470                 475                 480

Lys Pro Arg Lys Lys Ser Val Arg Val Phe Arg Glu Ile Val Ile Asn
                    485                 490                 495

Asn Gly Leu Thr Ser Asn Ile Arg Lys Glu Ile Leu Glu Glu Gly
                500                 505                 510

<210> SEQ ID NO 22
<211> LENGTH: 510
<212> TYPE: PRT
<213> ORGANISM: Pyrococcus furiosus

<400> SEQUENCE: 22

Met Phe Pro Glu Lys Phe Leu Trp Gly Val Ala Gln Ser Gly Phe Gln
1               5                   10                  15

Phe Glu Met Gly Asp Lys Leu Arg Arg Asn Ile Asp Thr Asn Thr Asp
                20                  25                  30

Trp Trp His Trp Val Arg Asp Lys Thr Asn Ile Glu Lys Gly Leu Val
            35                  40                  45

Ser Gly Asp Leu Pro Glu Glu Gly Ile Asn Asn Tyr Glu Leu Tyr Glu
    50                  55                  60

Lys Asp His Glu Ile Ala Arg Lys Leu Gly Leu Asn Ala Tyr Arg Ile
65              70                  75                  80

Gly Ile Glu Trp Ser Arg Ile Phe Pro Trp Pro Thr Thr Phe Ile Asp
                85                  90                  95

Val Asp Tyr Ser Tyr Asn Glu Ser Tyr Asn Leu Ile Gly Asp Val Lys
            100                 105                 110

Ile Thr Lys Asp Thr Leu Glu Glu Leu Asp Glu Ile Ala Asn Lys Arg
    115                 120                 125

Glu Val Ala Tyr Tyr Arg Ser Val Ile Asn Ser Leu Arg Ser Lys Gly
130                 135                 140

Phe Lys Val Ile Val Asn Leu Asn His Phe Thr Leu Pro Tyr Trp Leu
145                 150                 155                 160

His Asp Pro Ile Glu Ala Arg Glu Arg Ala Leu Thr Asn Lys Arg Asn
                165                 170                 175

Gly Trp Val Asn Pro Arg Thr Val Ile Glu Phe Ala Lys Tyr Ala Ala
            180                 185                 190

Tyr Ile Ala Tyr Lys Phe Gly Asp Ile Val Asp Met Trp Ser Thr Phe
    195                 200                 205

Asn Glu Pro Met Val Val Glu Leu Gly Tyr Leu Ala Pro Tyr Ser
210                 215                 220

Gly Phe Pro Pro Gly Val Leu Asn Pro Glu Ala Ala Lys Leu Ala Ile
225                 230                 235                 240

Leu His Met Ile Asn Ala His Ala Leu Ala Tyr Arg Gln Ile Lys Lys
                245                 250                 255

Phe Asp Thr Glu Lys Ala Asp Lys Asp Ser Lys Glu Pro Ala Glu Val
            260                 265                 270

Gly Ile Ile Tyr Asn Asn Ile Gly Val Ala Tyr Pro Lys Asp Pro Asn
    275                 280                 285

Asp Ser Lys Asp Val Lys Ala Ala Glu Asn Asp Asn Phe Phe His Ser
290                 295                 300
```

```
Gly Leu Phe Phe Glu Ala Ile His Lys Gly Lys Leu Asn Ile Glu Phe
305                 310                 315                 320

Asp Gly Glu Thr Phe Ile Asp Ala Pro Tyr Leu Lys Gly Asn Asp Trp
            325                 330                 335

Ile Gly Val Asn Tyr Tyr Thr Arg Glu Val Val Thr Tyr Gln Glu Pro
            340                 345                 350

Met Phe Pro Ser Ile Pro Leu Ile Thr Phe Lys Gly Val Gln Gly Tyr
            355                 360                 365

Gly Tyr Ala Cys Arg Pro Gly Thr Leu Ser Lys Asp Asp Arg Pro Val
        370                 375                 380

Ser Asp Ile Gly Trp Glu Leu Tyr Pro Glu Gly Met Tyr Asp Ser Ile
385                 390                 395                 400

Val Glu Ala His Lys Tyr Gly Val Pro Val Tyr Val Thr Glu Asn Gly
                405                 410                 415

Ile Ala Asp Ser Lys Asp Ile Leu Arg Pro Tyr Tyr Ile Ala Ser His
            420                 425                 430

Ile Lys Met Ile Glu Lys Ala Phe Glu Asp Gly Tyr Glu Val Lys Gly
        435                 440                 445

Tyr Phe His Trp Ala Leu Thr Asp Asn Phe Glu Trp Ala Leu Gly Phe
    450                 455                 460

Arg Met Arg Phe Gly Leu Tyr Glu Val Asn Leu Ile Thr Lys Glu Arg
465                 470                 475                 480

Ile Pro Arg Glu Lys Ser Val Ser Ile Phe Arg Glu Ile Val Ala Asn
                485                 490                 495

Asn Gly Val Thr Lys Lys Ile Glu Glu Glu Leu Leu Arg Gly
            500                 505                 510

<210> SEQ ID NO 23
<211> LENGTH: 537
<212> TYPE: PRT
<213> ORGANISM: Bankia gouldi

<400> SEQUENCE: 23

Met Arg Ile Arg Leu Ala Thr Leu Ala Leu Cys Ala Ala Leu Ser Pro
1               5                   10                  15

Val Thr Phe Ala Asp Asn Val Thr Val Gln Ile Asp Ala Asp Gly Gly
            20                  25                  30

Lys Lys Leu Ile Ser Arg Ala Leu Tyr Gly Met Asn Asn Ser Asn Ala
        35                  40                  45

Glu Ser Leu Thr Asp Thr Asp Trp Gln Arg Phe Arg Asp Ala Gly Val
50                  55                  60

Arg Met Leu Arg Glu Asn Gly Gly Asn Asn Ser Thr Lys Tyr Asn Trp
65                  70                  75                  80

Gln Leu His Leu Ser Ser His Pro Asp Trp Tyr Asn Asn Val Tyr Ala
                85                  90                  95

Gly Asn Asn Asn Trp Asp Asn Arg Val Ala Leu Ile Gln Glu Asn Leu
            100                 105                 110

Pro Gly Ala Asp Thr Met Trp Ala Phe Gln Leu Ile Gly Lys Val Ala
        115                 120                 125

Ala Thr Ser Ala Tyr Asn Phe Asn Asp Trp Glu Phe Asn Gln Ser Gln
    130                 135                 140

Trp Trp Thr Gly Val Ala Gln Asn Leu Ala Gly Gly Glu Pro Asn
145                 150                 155                 160

Leu Asp Gly Gly Gly Glu Ala Leu Val Glu Gly Asp Pro Asn Leu Tyr
                165                 170                 175
```

```
Leu Met Asp Trp Ser Pro Ala Asp Thr Val Gly Ile Leu Asp His Trp
        180                 185                 190

Phe Gly Val Asn Gly Leu Gly Val Arg Arg Gly Lys Ala Lys Tyr Trp
            195                 200                 205

Ser Met Asp Asn Glu Pro Gly Ile Trp Val Gly Thr His Asp Asp Val
210                 215                 220

Val Lys Glu Gln Thr Pro Val Glu Asp Phe Leu His Thr Tyr Phe Glu
225                 230                 235                 240

Thr Ala Lys Lys Ala Arg Ala Lys Phe Pro Gly Ile Lys Ile Thr Gly
                245                 250                 255

Pro Val Pro Ala Asn Glu Trp Gln Trp Tyr Ala Trp Gly Gly Phe Ser
                260                 265                 270

Val Pro Gln Glu Gln Gly Phe Met Ser Trp Met Glu Tyr Phe Ile Lys
            275                 280                 285

Arg Val Ser Glu Glu Gln Arg Ala Ser Gly Val Arg Leu Leu Asp Val
            290                 295                 300

Leu Asp Leu His Tyr Tyr Pro Gly Ala Tyr Asn Ala Glu Asp Ile Val
305                 310                 315                 320

Gln Leu His Arg Thr Phe Phe Asp Arg Asp Phe Val Ser Leu Asp Ala
                325                 330                 335

Asn Gly Val Lys Met Val Glu Gly Gly Trp Asp Asp Ser Ile Asn Lys
                340                 345                 350

Glu Tyr Ile Phe Gly Arg Val Asn Asp Trp Leu Glu Glu Tyr Met Gly
            355                 360                 365

Pro Asp His Gly Val Thr Leu Gly Leu Thr Glu Met Cys Val Arg Asn
370                 375                 380

Val Asn Pro Met Thr Thr Ala Ile Trp Tyr Ala Ser Met Leu Gly Thr
385                 390                 395                 400

Phe Ala Asp Asn Gly Val Glu Ile Phe Thr Pro Trp Cys Trp Asn Thr
                405                 410                 415

Gly Met Trp Glu Thr Leu His Leu Phe Ser Arg Tyr Asn Lys Pro Tyr
            420                 425                 430

Arg Val Ala Ser Ser Ser Leu Glu Glu Phe Val Ser Ala Tyr Ser
            435                 440                 445

Ser Ile Asn Glu Ala Glu Asp Ala Met Thr Val Leu Leu Val Asn Arg
450                 455                 460

Ser Thr Ser Glu Thr His Thr Ala Thr Val Ala Ile Asp Asp Phe Pro
465                 470                 475                 480

Leu Asp Gly Pro Tyr Arg Thr Leu Arg Leu His Asn Leu Pro Gly Glu
                485                 490                 495

Glu Thr Phe Val Ser His Arg Asp Asn Ala Leu Glu Lys Gly Thr Val
            500                 505                 510

Arg Ala Ser Asp Asn Thr Val Thr Leu Glu Leu Pro Pro Leu Ser Val
            515                 520                 525

Thr Ala Ile Leu Leu Lys Ala Arg Pro
530                 535

<210> SEQ ID NO 24
<211> LENGTH: 555
<212> TYPE: PRT
<213> ORGANISM: Thermotoga maritima

<400> SEQUENCE: 24

Val Ile Cys Val Glu Ile Phe Gly Lys Thr Phe Arg Glu Gly Arg Phe
```

```
             1               5              10              15
        Val Leu Lys Glu Lys Asn Phe Thr Val Glu Phe Ala Val Glu Lys Ile
                         20              25              30

His Leu Gly Trp Lys Ile Ser Gly Arg Val Lys Gly Ser Pro Gly Arg
                         35              40              45

Leu Glu Val Leu Arg Thr Lys Ala Pro Glu Lys Val Leu Val Asn Asn
                     50              55              60

Trp Gln Ser Trp Gly Pro Cys Arg Val Val Asp Ala Phe Ser Phe Lys
         65              70              75              80

Pro Pro Glu Ile Asp Pro Asn Trp Arg Tyr Thr Ala Ser Val Val Pro
                             85              90              95

Asp Val Leu Glu Arg Asn Leu Gln Ser Asp Tyr Phe Val Ala Glu Glu
                        100             105             110

Gly Lys Val Tyr Gly Phe Leu Ser Ser Lys Ile Ala His Pro Phe Phe
                        115             120             125

Ala Val Glu Asp Gly Glu Leu Val Ala Tyr Leu Glu Tyr Phe Asp Val
                    130             135             140

Glu Phe Asp Asp Phe Val Pro Leu Glu Pro Leu Val Val Leu Glu Asp
        145             150             155             160

Pro Asn Thr Pro Leu Leu Glu Lys Tyr Ala Glu Leu Val Gly Met
                            165             170             175

Glu Asn Asn Ala Arg Val Pro Lys His Thr Pro Thr Gly Trp Cys Ser
                        180             185             190

Trp Tyr His Tyr Phe Leu Asp Leu Thr Trp Glu Glu Thr Leu Lys Asn
                        195             200             205

Leu Lys Leu Ala Lys Asn Phe Pro Phe Glu Val Phe Gln Ile Asp Asp
                    210             215             220

Ala Tyr Glu Lys Asp Ile Gly Asp Trp Leu Val Thr Arg Gly Asp Phe
        225             230             235             240

Pro Ser Val Glu Glu Met Ala Lys Val Ile Ala Glu Asn Gly Phe Ile
                        245             250             255

Pro Gly Ile Trp Thr Ala Pro Phe Ser Val Ser Glu Thr Ser Asp Val
                        260             265             270

Phe Asn Glu His Pro Asp Trp Val Val Lys Glu Asn Gly Glu Pro Lys
                    275             280             285

Met Ala Tyr Arg Asn Trp Asn Lys Lys Ile Tyr Ala Leu Asp Leu Ser
                    290             295             300

Lys Asp Glu Val Leu Asn Trp Leu Phe Asp Leu Phe Ser Ser Leu Arg
        305             310             315             320

Lys Met Gly Tyr Arg Tyr Phe Lys Ile Asp Phe Leu Phe Ala Gly Ala
                        325             330             335

Val Pro Gly Glu Arg Lys Lys Asn Ile Thr Pro Ile Gln Ala Phe Arg
                        340             345             350

Lys Gly Ile Glu Thr Ile Arg Lys Ala Val Gly Glu Asp Ser Phe Ile
                        355             360             365

Leu Gly Cys Gly Ser Pro Leu Leu Pro Ala Val Gly Cys Val Asp Gly
            370             375             380

Met Arg Ile Gly Pro Asp Thr Ala Pro Phe Trp Gly Glu His Ile Glu
        385             390             395             400

Asp Asn Gly Ala Pro Ala Ala Arg Trp Ala Leu Arg Asn Ala Ile Thr
                        405             410             415

Arg Tyr Phe Met His Asp Arg Phe Trp Leu Asn Asp Pro Asp Cys Leu
                        420             425             430
```

```
Ile Leu Arg Glu Glu Lys Thr Asp Leu Thr Gln Lys Glu Lys Glu Leu
            435                 440                 445

Tyr Ser Tyr Thr Cys Gly Val Leu Asp Asn Met Ile Ile Glu Ser Asp
    450                 455                 460

Asp Leu Ser Leu Val Arg Asp His Gly Lys Lys Val Leu Lys Glu Thr
465                 470                 475                 480

Leu Glu Leu Leu Gly Gly Arg Pro Arg Val Gln Asn Ile Met Ser Glu
                485                 490                 495

Asp Leu Arg Tyr Glu Ile Val Ser Ser Gly Thr Leu Ser Gly Asn Val
            500                 505                 510

Lys Ile Val Val Asp Leu Asn Ser Arg Glu Tyr His Leu Glu Lys Glu
            515                 520                 525

Gly Lys Ser Ser Leu Lys Lys Arg Val Val Lys Arg Glu Asp Gly Arg
        530                 535                 540

Asn Phe Tyr Phe Tyr Glu Glu Gly Glu Arg Glu
545                 550                 555

<210> SEQ ID NO 25
<211> LENGTH: 680
<212> TYPE: PRT
<213> ORGANISM: Thermotoga maritima

<400> SEQUENCE: 25

Met Gly Ile Gly Gly Asp Asp Ser Trp Ser Pro Ser Val Ser Ala Glu
  1               5                  10                  15

Phe Leu Leu Leu Ile Val Glu Leu Ser Phe Val Leu Phe Ala Ser Asp
                20                  25                  30

Glu Phe Val Lys Val Glu Asn Gly Lys Phe Ala Leu Asn Gly Lys Glu
            35                  40                  45

Phe Arg Phe Ile Gly Ser Asn Asn Tyr Tyr Met His Tyr Lys Ser Asn
    50                  55                  60

Gly Met Ile Asp Ser Val Leu Glu Ser Ala Arg Asp Met Gly Ile Lys
 65                  70                  75                  80

Val Leu Arg Ile Trp Gly Phe Leu Asp Gly Glu Ser Tyr Cys Arg Asp
                85                  90                  95

Lys Asn Thr Tyr Met His Pro Glu Pro Gly Val Phe Gly Val Pro Glu
            100                 105                 110

Gly Ile Ser Asn Ala Gln Ser Gly Phe Glu Arg Leu Asp Tyr Thr Val
        115                 120                 125

Ala Lys Ala Lys Glu Leu Gly Ile Lys Leu Val Ile Val Leu Val Asn
130                 135                 140

Asn Trp Asp Asp Phe Gly Gly Met Asn Gln Tyr Val Arg Trp Phe Gly
145                 150                 155                 160

Gly Thr His His Asp Asp Phe Tyr Arg Asp Glu Lys Ile Lys Glu Glu
                165                 170                 175

Tyr Lys Lys Tyr Val Ser Phe Leu Val Asn His Val Asn Thr Tyr Thr
            180                 185                 190

Gly Val Pro Tyr Arg Glu Glu Pro Thr Ile Met Ala Trp Glu Leu Ala
        195                 200                 205

Asn Glu Pro Arg Cys Glu Thr Asp Lys Ser Gly Asn Thr Leu Val Glu
    210                 215                 220

Trp Val Lys Glu Met Ser Ser Tyr Ile Lys Ser Leu Asp Pro Asn His
225                 230                 235                 240

Leu Val Ala Val Gly Asp Glu Gly Phe Phe Ser Asn Tyr Glu Gly Phe
```

```
                245                 250                 255
Lys Pro Tyr Gly Gly Glu Ala Glu Trp Ala Tyr Asn Gly Trp Ser Gly
            260                 265                 270
Val Asp Trp Lys Lys Leu Leu Ser Ile Glu Thr Val Asp Phe Gly Thr
        275                 280                 285
Phe His Leu Tyr Pro Ser His Trp Gly Val Ser Pro Glu Asn Tyr Ala
    290                 295                 300
Gln Trp Gly Ala Lys Trp Ile Glu Asp His Ile Lys Ile Ala Lys Glu
305                 310                 315                 320
Ile Gly Lys Pro Val Val Leu Glu Glu Tyr Gly Ile Pro Lys Ser Ala
                325                 330                 335
Pro Val Asn Arg Thr Ala Ile Tyr Arg Leu Trp Asn Asp Leu Val Tyr
            340                 345                 350
Asp Leu Gly Gly Asp Gly Ala Met Phe Trp Met Leu Ala Gly Ile Gly
        355                 360                 365
Glu Gly Ser Asp Arg Asp Glu Arg Gly Tyr Tyr Pro Asp Tyr Asp Gly
    370                 375                 380
Phe Arg Ile Val Asn Asp Asp Ser Pro Glu Ala Glu Leu Ile Arg Glu
385                 390                 395                 400
Tyr Ala Lys Leu Phe Asn Thr Gly Glu Asp Ile Arg Glu Asp Thr Cys
                405                 410                 415
Ser Phe Ile Leu Pro Lys Asp Gly Met Glu Ile Lys Lys Thr Val Glu
            420                 425                 430
Val Arg Ala Gly Val Phe Asp Tyr Ser Asn Thr Phe Glu Lys Leu Ser
        435                 440                 445
Val Lys Val Glu Asp Leu Val Phe Glu Asn Glu Ile Glu His Leu Gly
    450                 455                 460
Tyr Gly Ile Tyr Gly Phe Asp Leu Asp Thr Thr Arg Ile Pro Asp Gly
465                 470                 475                 480
Glu His Glu Met Phe Leu Glu Gly His Phe Gln Gly Lys Thr Val Lys
                485                 490                 495
Asp Ser Ile Lys Ala Lys Val Val Asn Glu Ala Arg Tyr Val Leu Ala
            500                 505                 510
Glu Glu Val Asp Phe Ser Ser Pro Glu Val Lys Asn Trp Trp Asn
        515                 520                 525
Ser Gly Thr Trp Gln Ala Glu Phe Gly Ser Pro Asp Ile Glu Trp Asn
    530                 535                 540
Gly Glu Val Gly Asn Gly Ala Leu Gln Leu Asn Val Lys Leu Pro Gly
545                 550                 555                 560
Lys Ser Asp Trp Glu Glu Val Arg Val Ala Arg Lys Phe Glu Arg Leu
                565                 570                 575
Ser Glu Cys Glu Ile Leu Glu Tyr Asp Ile Tyr Ile Pro Asn Val Glu
            580                 585                 590
Gly Leu Lys Gly Arg Leu Arg Pro Tyr Ala Val Leu Asn Pro Gly Trp
        595                 600                 605
Val Lys Ile Gly Leu Asp Met Asn Asn Ala Asn Val Glu Ser Ala Glu
    610                 615                 620
Ile Ile Thr Phe Gly Gly Lys Gly Tyr Arg Arg Phe His Val Arg Ile
625                 630                 635                 640
Glu Phe Asp Arg Thr Ala Gly Val Lys Glu Leu His Ile Gly Val Val
                645                 650                 655
Gly Asp His Leu Arg Tyr Asp Gly Pro Ile Phe Ile Asp Asn Val Arg
            660                 665                 670
```

```
Leu Tyr Lys Arg Thr Gly Gly Met
        675             680

<210> SEQ ID NO 26
<211> LENGTH: 512
<212> TYPE: PRT
<213> ORGANISM: Thermococcus chitonophagus

<400> SEQUENCE: 26

Met Leu Pro Glu Glu Phe Leu Trp Gly Val Gly Gln Ser Gly Phe Gln
 1               5                  10                  15

Phe Glu Met Gly Asp Lys Leu Arg Arg His Ile Asp Pro Asn Thr Asp
            20                  25                  30

Trp Trp Lys Trp Val Arg Asp Pro Phe Asn Ile Lys Lys Glu Leu Val
        35                  40                  45

Ser Gly Asp Leu Pro Glu Asp Gly Ile Asn Asn Tyr Glu Leu Phe Glu
    50                  55                  60

Asn Asp His Lys Leu Ala Lys Gly Leu Gly Leu Asn Ala Tyr Arg Ile
65                  70                  75                  80

Gly Ile Glu Trp Ser Arg Ile Phe Pro Trp Pro Thr Trp Thr Val Asp
                85                  90                  95

Thr Glu Val Glu Phe Asp Thr Tyr Gly Leu Val Lys Asp Val Lys Ile
            100                 105                 110

Asp Lys Ser Thr Leu Ala Glu Leu Asp Arg Leu Ala Asn Lys Glu Glu
        115                 120                 125

Val Met Tyr Tyr Arg Arg Val Ile Gln His Leu Arg Glu Leu Gly Phe
    130                 135                 140

Lys Val Phe Val Asn Leu Asn His Phe Thr Leu Pro Ile Trp Leu His
145                 150                 155                 160

Asp Pro Ile Val Ala Arg Glu Lys Ala Leu Thr Asn Asp Arg Ile Gly
                165                 170                 175

Trp Val Ser Gln Arg Thr Val Val Glu Phe Ala Lys Tyr Ala Ala Tyr
            180                 185                 190

Ile Ala His Ala Leu Gly Asp Leu Val Asp Thr Trp Ser Thr Phe Asn
        195                 200                 205

Glu Pro Met Val Val Glu Leu Gly Tyr Leu Ala Pro Tyr Ser Gly
    210                 215                 220

Phe Pro Pro Gly Val Met Asn Pro Glu Ala Ala Lys Leu Ala Ile Leu
225                 230                 235                 240

Asn Met Ile Asn Ala His Ala Leu Ala Tyr Lys Met Ile Lys Arg Phe
                245                 250                 255

Asp Thr Lys Lys Ala Asp Glu Asp Ser Lys Ser Pro Ala Asp Val Gly
            260                 265                 270

Ile Ile Tyr Asn Asn Ile Gly Val Ala Tyr Pro Lys Asp Pro Asn Asp
        275                 280                 285

Pro Lys Asp Val Lys Ala Ala Glu Asn Asp Asn Tyr Phe His Ser Gly
    290                 295                 300

Leu Phe Phe Asp Ala Ile His Lys Gly Lys Leu Asn Ile Glu Phe Asp
305                 310                 315                 320

Gly Glu Asn Phe Val Lys Val Arg His Leu Lys Gly Asn Asp Trp Ile
                325                 330                 335

Gly Leu Asn Tyr Tyr Thr Arg Glu Val Val Arg Tyr Ser Glu Pro Lys
            340                 345                 350

Phe Pro Ser Ile Pro Leu Ile Ser Phe Lys Gly Val Pro Asn Tyr Gly
```

```
                355                 360                 365
Tyr Ser Cys Arg Pro Gly Thr Thr Ser Ala Asp Gly Met Pro Val Ser
370                 375                 380

Asp Ile Gly Trp Glu Val Tyr Pro Gln Gly Ile Tyr Asp Ser Ile Val
385                 390                 395                 400

Glu Ala Thr Lys Tyr Ser Val Pro Val Tyr Val Thr Glu Asn Gly Val
                405                 410                 415

Ala Asp Ser Ala Asp Thr Leu Arg Pro Tyr Tyr Ile Val Ser His Val
                420                 425                 430

Ser Lys Ile Glu Glu Ala Ile Glu Asn Gly Tyr Pro Val Lys Gly Tyr
                435                 440                 445

Met Tyr Trp Ala Leu Thr Asp Asn Tyr Glu Trp Ala Leu Gly Phe Ser
                450                 455                 460

Met Arg Phe Gly Leu Tyr Lys Val Asp Leu Ile Ser Lys Glu Arg Ile
465                 470                 475                 480

Pro Arg Glu Arg Ser Val Glu Ile Tyr Arg Arg Ile Val Gln Ser Asn
                485                 490                 495

Gly Val Pro Lys Asp Ile Lys Glu Glu Phe Leu Lys Gly Glu Glu Lys
                500                 505                 510

<210> SEQ ID NO 27
<211> LENGTH: 360
<212> TYPE: PRT
<213> ORGANISM: Thermotoga sp.

<400> SEQUENCE: 27

Met Val Glu Arg His Phe Arg Tyr Val Leu Ile Cys Thr Leu Phe Leu
1               5                   10                  15

Val Met Leu Leu Ile Ser Ser Thr Gln Cys Gly Lys Asn Glu Pro Asn
                20                  25                  30

Lys Arg Val Asn Ser Met Glu Gln Ser Val Ala Glu Ser Asp Ser Asn
                35                  40                  45

Ser Ala Phe Glu Tyr Asn Lys Met Val Gly Lys Gly Val Asn Ile Gly
50                  55                  60

Asn Ala Leu Glu Ala Pro Phe Glu Gly Ala Trp Gly Val Arg Ile Glu
65                  70                  75                  80

Asp Glu Tyr Phe Glu Ile Ile Lys Lys Arg Gly Phe Asp Ser Val Arg
                85                  90                  95

Ile Pro Ile Arg Trp Ser Ala His Ile Ser Glu Lys Pro Pro Tyr Asp
                100                 105                 110

Ile Asp Arg Asn Phe Leu Glu Arg Val Asn His Val Val Asp Arg Ala
                115                 120                 125

Leu Glu Asn Asn Leu Thr Val Ile Ile Asn Thr His His Phe Glu Glu
                130                 135                 140

Leu Tyr Gln Glu Pro Asp Lys Tyr Gly Asp Val Leu Val Glu Ile Trp
145                 150                 155                 160

Arg Gln Ile Ala Lys Phe Phe Lys Asp Tyr Pro Glu Asn Leu Phe Phe
                165                 170                 175

Glu Ile Tyr Asn Glu Pro Ala Gln Asn Leu Thr Ala Glu Lys Trp Asn
                180                 185                 190

Ala Leu Tyr Pro Lys Val Leu Lys Val Ile Arg Glu Ser Asn Pro Thr
                195                 200                 205

Arg Ile Val Ile Ile Asp Ala Pro Asn Trp Ala His Tyr Ser Ala Val
                210                 215                 220
```

```
Arg Ser Leu Lys Leu Val Asn Asp Lys Arg Ile Ile Val Ser Phe His
225                 230                 235                 240

Tyr Tyr Glu Pro Phe Lys Phe Thr His Gln Gly Ala Glu Trp Val Asn
            245                 250                 255

Pro Ile Pro Val Arg Val Lys Trp Asn Gly Glu Glu Trp Glu Ile
        260                 265                 270

Asn Gln Ile Arg Ser His Phe Lys Tyr Val Ser Asp Trp Ala Lys Gln
                275                 280                 285

Asn Asn Val Pro Ile Phe Leu Gly Glu Phe Gly Ala Tyr Ser Lys Ala
290                 295                 300

Asp Met Asp Ser Arg Val Lys Trp Thr Glu Ser Val Arg Lys Met Ala
305                 310                 315                 320

Glu Glu Phe Gly Phe Ser Tyr Ala Tyr Trp Glu Phe Cys Ala Gly Phe
                325                 330                 335

Gly Ile Tyr Asp Arg Trp Ser Gln Asn Trp Ile Glu Pro Leu Ala Thr
                340                 345                 350

Ala Val Val Gly Thr Gly Lys Glu
            355                 360

<210> SEQ ID NO 28
<211> LENGTH: 772
<212> TYPE: PRT
<213> ORGANISM: Thermotoga maritima

<400> SEQUENCE: 28

Met Asp Leu Thr Lys Val Gly Ile Ile Val Arg Leu Asn Glu Trp Gln
1               5                   10                  15

Ala Lys Asp Val Ala Lys Asp Arg Phe Ile Glu Ile Lys Asp Gly Lys
                20                  25                  30

Ala Glu Val Trp Ile Leu Gln Gly Val Glu Glu Ile Phe Tyr Glu Lys
            35                  40                  45

Pro Asp Thr Ser Pro Arg Ile Phe Phe Ala Gln Ala Arg Ser Asn Lys
        50                  55                  60

Val Ile Glu Ala Phe Leu Thr Asn Pro Val Asp Thr Lys Lys Lys Glu
65                  70                  75                  80

Leu Phe Lys Val Thr Val Asp Gly Lys Glu Ile Pro Val Ser Arg Val
                85                  90                  95

Glu Lys Ala Asp Pro Thr Asp Ile Asp Val Thr Asn Tyr Val Arg Ile
                100                 105                 110

Val Leu Ser Glu Ser Leu Lys Glu Glu Asp Leu Arg Lys Asp Val Glu
            115                 120                 125

Leu Ile Ile Glu Gly Tyr Lys Pro Ala Arg Val Ile Met Met Glu Ile
130                 135                 140

Leu Asp Asp Tyr Tyr Asp Gly Glu Leu Gly Ala Val Tyr Ser Pro
145                 150                 155                 160

Glu Lys Thr Ile Phe Arg Val Trp Ser Pro Val Ser Lys Trp Val Lys
                165                 170                 175

Val Leu Leu Phe Lys Asn Gly Glu Asp Thr Glu Pro Tyr Gln Val Val
            180                 185                 190

Asn Met Glu Tyr Lys Gly Asn Gly Val Trp Ala Val Val Glu Gly
        195                 200                 205

Asp Leu Asp Gly Val Phe Tyr Leu Tyr Gln Leu Glu Asn Tyr Gly Lys
    210                 215                 220

Ile Arg Thr Thr Val Asp Pro Tyr Ser Lys Ala Val Tyr Ala Asn Ser
225                 230                 235                 240
```

```
Lys Lys Ser Ala Val Val Asn Leu Ala Arg Thr Asn Pro Glu Gly Trp
            245                 250                 255

Glu Asn Asp Arg Gly Pro Lys Ile Glu Gly Tyr Glu Asp Ala Ile Ile
                260                 265                 270

Tyr Glu Ile His Ile Ala Asp Ile Thr Gly Leu Glu Asn Ser Gly Val
        275                 280                 285

Lys Asn Lys Gly Leu Tyr Leu Gly Leu Thr Glu Glu Asn Thr Lys Gly
    290                 295                 300

Pro Gly Gly Val Thr Thr Gly Leu Ser His Leu Val Glu Leu Gly Val
305                 310                 315                 320

Thr His Val His Ile Leu Pro Phe Phe Asp Phe Tyr Thr Gly Asp Glu
                325                 330                 335

Leu Asp Lys Asp Phe Glu Lys Tyr Tyr Asn Trp Gly Tyr Asp Pro Tyr
                340                 345                 350

Leu Phe Met Val Pro Glu Gly Arg Tyr Ser Thr Asp Pro Lys Asn Pro
            355                 360                 365

His Thr Arg Ile Arg Glu Val Lys Glu Met Val Lys Ala Leu His Lys
        370                 375                 380

His Gly Ile Gly Val Ile Met Asp Met Val Phe Pro His Thr Tyr Gly
385                 390                 395                 400

Ile Gly Glu Leu Ser Ala Phe Asp Gln Thr Val Pro Tyr Tyr Phe Tyr
                405                 410                 415

Arg Ile Asp Lys Thr Gly Ala Tyr Leu Asn Glu Ser Gly Cys Gly Asn
                420                 425                 430

Val Ile Ala Ser Glu Arg Pro Met Met Arg Lys Phe Ile Val Asp Thr
            435                 440                 445

Val Thr Tyr Trp Val Lys Glu Tyr His Ile Asp Gly Phe Arg Phe Asp
450                 455                 460

Gln Met Gly Leu Ile Asp Lys Lys Thr Met Leu Glu Val Glu Arg Ala
465                 470                 475                 480

Leu His Lys Ile Asp Pro Thr Ile Ile Leu Tyr Gly Glu Pro Trp Gly
                485                 490                 495

Gly Trp Gly Ala Pro Ile Arg Phe Gly Lys Ser Asp Val Ala Gly Thr
            500                 505                 510

His Val Ala Ala Phe Asn Asp Glu Phe Arg Asp Ala Ile Arg Gly Ser
            515                 520                 525

Val Phe Asn Pro Ser Val Lys Gly Phe Val Met Gly Gly Tyr Gly Lys
            530                 535                 540

Glu Thr Lys Ile Lys Arg Gly Val Val Gly Ser Ile Asn Tyr Asp Gly
545                 550                 555                 560

Lys Leu Ile Lys Ser Leu Ala Leu Asp Pro Glu Glu Thr Ile Asn Tyr
                565                 570                 575

Ala Ala Cys His Asp Asn His Thr Leu Trp Asp Lys Asn Tyr Leu Ala
            580                 585                 590

Ala Lys Ala Asp Lys Lys Lys Glu Trp Thr Glu Glu Leu Lys Asn
            595                 600                 605

Ala Gln Lys Leu Ala Gly Ala Ile Leu Leu Thr Ser Gln Gly Val Pro
            610                 615                 620

Phe Leu His Gly Gly Gln Asp Phe Cys Arg Thr Lys Asn Phe Asn Asp
625                 630                 635                 640

Asn Ser Tyr Asn Ala Pro Ile Ser Ile Asn Gly Phe Asp Tyr Glu Arg
                645                 650                 655
```

```
Lys Leu Gln Phe Ile Asp Val Phe Asn Tyr His Lys Gly Leu Ile Lys
            660                 665                 670

Leu Arg Lys Glu His Pro Ala Phe Arg Leu Lys Asn Ala Glu Glu Ile
        675                 680                 685

Lys Lys His Leu Glu Phe Leu Pro Gly Gly Arg Arg Ile Val Ala Phe
    690                 695                 700

Met Leu Lys Asp His Ala Gly Gly Asp Pro Trp Lys Asp Ile Val Val
705                 710                 715                 720

Ile Tyr Asn Gly Asn Leu Glu Lys Thr Thr Tyr Lys Leu Pro Glu Gly
                725                 730                 735

Lys Trp Asn Val Val Asn Ser Gln Lys Ala Gly Thr Glu Val Ile
            740                 745                 750

Glu Thr Val Glu Gly Thr Ile Glu Leu Asp Pro Leu Ser Ala Tyr Val
        755                 760                 765

Leu Tyr Arg Glu
    770

<210> SEQ ID NO 29
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 29
ccgagaattc attaaagagg agaaattaac tatggtgaat gctatgattg tc         52

<210> SEQ ID NO 30
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 30
atacccgaag gcctcgatac ttctagaagg c                                31

<210> SEQ ID NO 31
<211> LENGTH: 54
<212> TYPE: DNA
<213> ORGANISM: Artificial sequence
<220> FEATURE:
<223> OTHER INFORMATION: synthetically generated oligonucleotide

<400> SEQUENCE: 31
ccgagaattc attaaagagg agaaattaac tatgataaga aggtccgatt ttcc       54

<210> SEQ ID NO 32
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 32
ttccttaaag attttagaat ttctagaagg c                                31

<210> SEQ ID NO 33
<211> LENGTH: 52
<212> TYPE: DNA
<213> ORGANISM: Artificial sequence
<220> FEATURE:
<223> OTHER INFORMATION: synthetically generated oligonucleotide
```

<400> SEQUENCE: 33
ccgagaattc attaaagagg agaaattaac tatgctacca gaaggctttc tc    52

<210> SEQ ID NO 34
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 34
ctcttcaagc ctgaacccac tccatggagg c    31

<210> SEQ ID NO 35
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 35
ccgagaattc attaaagagg agaaattaac tatgataagg tttcctgatt at    52

<210> SEQ ID NO 36
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 36
cctaatttct tggagcttat ttctagaagg c    31

<210> SEQ ID NO 37
<211> LENGTH: 57
<212> TYPE: DNA
<213> ORGANISM: Artificial sequence
<220> FEATURE:
<223> OTHER INFORMATION: synthetically generated oligonucleotide

<400> SEQUENCE: 37
ccgagaattc attcattaaa gaggagaaat taactatgct tccaggagaa ctttctc    57

<210> SEQ ID NO 38
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 38
ctctagaatc tcctccccat ccctaggagg c    31

<210> SEQ ID NO 39
<211> LENGTH: 40
<212> TYPE: DNA
<213> ORGANISM: Artificial sequence
<220> FEATURE:
<223> OTHER INFORMATION: synthetically generated oligonucleotide

<400> SEQUENCE: 39
ataatctaga gcatgcaatt ccccaaagac ttcatgatag    40

<210> SEQ ID NO 40

<211> LENGTH: 32
<212> TYPE: DNA
<213> ORGANISM: Artificial sequence
<220> FEATURE:
<223> OTHER INFORMATION: synthetically generated oligonucleotide

<400> SEQUENCE: 40
tcgtagaatg tgactaggtc attcgaaaat aa                                    32

<210> SEQ ID NO 41
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 41
ccgacaattg attaaagagg agaaattaac tatggaaagg atcgatgaaa tt              52

<210> SEQ ID NO 42
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 42
ctcttctcta agtttggtac tccatggagg c                                     31

<210> SEQ ID NO 43
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 43
ccgacaattg attaaagagg agaaattaac tatgttccct gaaaagttcc tt              52

<210> SEQ ID NO 44
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 44
ctccttaacg actcccctac tccatggagg c                                     31

<210> SEQ ID NO 45
<211> LENGTH: 27
<212> TYPE: DNA
<213> ORGANISM: Artificial sequence
<220> FEATURE:
<223> OTHER INFORMATION: synthetically generated oligonucleotide

<400> SEQUENCE: 45
aataaggatc cgtttagcga cgctcgc                                          27

<210> SEQ ID NO 46
<211> LENGTH: 35
<212> TYPE: DNA
<213> ORGANISM: Artificial sequence
<220> FEATURE:
<223> OTHER INFORMATION: synthetically generated oligonucleotide

<400> SEQUENCE: 46
cggataatgg cgacatgttg ggccttcgaa aataa            35

<210> SEQ ID NO 47
<211> LENGTH: 60
<212> TYPE: DNA
<213> ORGANISM: Artificial sequence
<220> FEATURE:
<223> OTHER INFORMATION: synthetically generated oligonucleotide

<400> SEQUENCE: 47
tttattgaat tcattaaaga ggagaaatta actatgatct gtgtggaaat attcggaaag    60

<210> SEQ ID NO 48
<211> LENGTH: 40
<212> TYPE: DNA
<213> ORGANISM: Artificial sequence
<220> FEATURE:
<223> OTHER INFORMATION: primer sequence

<400> SEQUENCE: 48
gaagatgctt ctcccactct ctcttacttt cgaaatatct                          40

<210> SEQ ID NO 49
<211> LENGTH: 54
<212> TYPE: DNA
<213> ORGANISM: Artificial sequence
<220> FEATURE:
<223> OTHER INFORMATION: synthetically generated oligonucleotide

<400> SEQUENCE: 49
tttattcaat tgattaaaga ggagaaatta actatgggga ttggtggcga cgac          54

<210> SEQ ID NO 50
<211> LENGTH: 36
<212> TYPE: DNA
<213> ORGANISM: Artificial sequence
<220> FEATURE:
<223> OTHER INFORMATION: synthetically generated oligonucleotide

<400> SEQUENCE: 50
cctccataca cttatacttt tctattcgaa ttattt                              36

<210> SEQ ID NO 51
<211> LENGTH: 60
<212> TYPE: DNA
<213> ORGANISM: Artificial sequence
<220> FEATURE:
<223> OTHER INFORMATION: synthetically generated oligonucleotide

<400> SEQUENCE: 51
tttattgaat tcattaaaga ggagaaatta actatgctac cagaagagtt cctatggggc    60

<210> SEQ ID NO 52
<211> LENGTH: 39
<212> TYPE: DNA
<213> ORGANISM: Artificial sequence
<220> FEATURE:
<223> OTHER INFORMATION: synthetically generated oligonucleotide

<400> SEQUENCE: 52
ctttacttct ggtatcggca actactcttc gaattattt                           39

<210> SEQ ID NO 53
<211> LENGTH: 68
<212> TYPE: DNA

<213> ORGANISM: Artificial sequence
<220> FEATURE:
<223> OTHER INFORMATION: synthetically generated oligonucleotide

<400> SEQUENCE: 53

```
aaaaaacaat tgaattcatt aaagaggaga aattaactat ggtagaaaga cacttcagat    60
atgttctt                                                              68
```

<210> SEQ ID NO 54
<211> LENGTH: 36
<212> TYPE: DNA
<213> ORGANISM: Artificial sequence
<220> FEATURE:
<223> OTHER INFORMATION: synthetically generated oligonucleotide

<400> SEQUENCE: 54

```
gtccgtttct catttacttc ttaacctagg ctttttt                              36
```

<210> SEQ ID NO 55
<211> LENGTH: 56
<212> TYPE: DNA
<213> ORGANISM: Artificial sequence
<220> FEATURE:
<223> OTHER INFORMATION: synthetically generated oligonucleotide

<400> SEQUENCE: 55

```
ttttggaatt cattaaagag gagaaattaa ctatggaact gatcatagaa ggttac         56
```

<210> SEQ ID NO 56
<211> LENGTH: 36
<212> TYPE: DNA
<213> ORGANISM: Artificial sequence
<220> FEATURE:
<223> OTHER INFORMATION: synthetically generated oligonucleotide

<400> SEQUENCE: 56

```
cgcatgcaag acatgtctct cacttttcga agaata                               36
```

<210> SEQ ID NO 57
<211> LENGTH: 1992
<212> TYPE: DNA
<213> ORGANISM: Thermotoga maritima

<400> SEQUENCE: 57

```
cttttattga tcgttgagct ctctttcgtt ctctttgcaa gtgacgagtt cgtgaaagtg    60
gaaaacggaa aattcgctct gaacggaaaa gaattcagat tcattggaag caacaactac   120
tacatgcact acaagagcaa cggaatgata gacagtgttc tggagagtgc cagagacatg   180
ggtataaagg tcctcagaat ctggggtttc ctcgacgggg agagttactg cagagacaag   240
aacacctaca tgcatcctga gcccggtgtt ttcggggtgc cagaaggaat atcgaacgcc   300
cagagcggtt tcgaaagact cgactacaca gttgcgaaag cgaagaaact cggtataaaa   360
cttgtcattg ttcttgtgaa caactgggac gacttcggtg aatgaaccag tacgtgagg    420 tggtttggag gaacccatca cgacgatttc tacagagatg aaagatcaa agaagagtac   480 aaaaagtacg tctccttctc cgtaaaccat gtcaatacct acacgggagt tccttacagg   540
gaagagccca ccatcatggc ctgggagctt gcaaacgaac cgcgctgtga acggacaaa    600 tcggggaaca cgctcgttga gtgggtgaag gagatgagct cctacataaa gagtctggat   660
cccaaccacc tcgtggctgt ggggacgaa ggattcttca gcaactacga aggattcaaa    720
ccttacggtg agaagccga gtgggcctac aacggctggt ccggtgttga ctggaagaag   780
```

```
ctcctttcga tagagacggt ggacttcggc acgttccacc tctatccgtc ccactggggt    840
gtcagtccag agaactatgc ccagtgggga gcgaagtgga tagaagacca cataaagatc    900
gcaaaagaga tcggaaaacc cgttgttctg aagaatatg  gaattccaaa gagtgcgcca    960
gttaacagaa cggccatcta cagactctgg aacgatctgg tctacgatct cggtggagat   1020
ggagcgatgt tctggatgct cgcgggaatc ggggaaggtt cggacagaga cgagagaggg   1080
tactatccgg actacgacgg tttcagaata gtgaacgacg acagtccaga agcggaactg   1140
ataagagaat acgcgaagct gttcaacaca ggtgaagaca aagagaaga  cacctgctct   1200
ttcatccttc caaagacgg  catggagatc aaaaagaccg tggaagtgag ggctggtgtt   1260
ttcgactaca gcaacacgtt tgaaaagttg tctgtcaaag tcgaagatct ggttttttgaa   1320
aatgagatag agcatctcgg atacggaatt tacggctttg atctcgacac aacccggatc   1380
ccggatggag aacatgaaat gttccttgaa ggccactttc agggaaaaac ggtgaaagac   1440
tctatcaaag cgaaagtggt gaacgaagca cggtacgtgc tcgcagagga agttgatttt   1500
tcctctccag aagaggtgaa aaactggtgg aacagcggaa cctggcaggc agagttcggg   1560
tcacctgaca ttgaatggaa cggtgaggtg ggaaatggag cactgcagct gaacgtgaaa   1620
ctgcccggaa agagcgactg ggaagaagtg agagtagcaa ggaagttcga aagactctca   1680
gaatgtgaga tcctcgagta cgacatctac attccaaacg tcgagggact caagggaagg   1740
ttgaggccgt acgcggttct gaaccccggc tgggtgaaga taggcctcga catgaacaac   1800
gcgaacgtgg aaagtgcgga gatcatcact ttcggcggaa aagagtacag aagattccat   1860
gtaagaattg agttcgacag aacagcgggg gtgaaagaac ttcacatagg agttgtcggt   1920
gatcatctga ggtacgatgg accgattttc atcgataatg tgagactttta taaaagaaca   1980
ggaggtatgt ga                                                       1992
```

<210> SEQ ID NO 58
<211> LENGTH: 2055
<212> TYPE: DNA
<213> ORGANISM: Thermotoga maritima

<400> SEQUENCE: 58

```
atgaaaagaa tcgacctgaa tggttttctgg agcgttaggg ataacgaagg gagattttcg     60
tttgaaggga ctgtgccagg ggttgtccag gcagatctgg tcagaaaagg tcttcttcca    120
cacccgtacg ttgggatgaa cgaagatctc ttcaaggaaa tagaagacag agagtggatc    180
tacgagaggg agttcgagtt caagaagat  gtgaaagagg gggaacgtgt cgatctcgtt    240
tttgagggcg tcgacacgct gtcggatgtt tatctgaacg gtgtttaccct tggaagcacc    300
gaagacatgt tcatcgagta tcgcttcgat gtcacgaacg tgttgaaaga aagaatcac     360
ctgaaggtgt acataaaatc tcccatcaga gttccgaaaa ctctcgagca gaactacggg    420
gtcctcggcg gtcctgaaga tcccatcaga ggatacataa aaaagcccca gtattcgtac    480
ggatgggact ggggtgccag aatcgttaca agcggtattt ggaaaccgt  ctacctcgag    540
gtgtacaggg cacgtcttca ggattcaacg gcttatctgt ggaacttga  ggggaaagat    600
gcccttgtga gggtgaacgg tttcgtacac ggggaaggaa atctcattgt ggaagtttat    660
gtaaacggtg aaaagatagg ggagtttcct gttcttgaaa agaacggaga aaagctcttc    720
gatggagtgt tccacctgaa agatgtgaaa ctatggtatc cgtggaacgt ggggaaaccg    780
tacctgtacg atttcgttt  cgtgttgaaa gacttaaacg gagagatcta cagagaagaa    840
```

```
aagaaaatcg gtttgagaag agtcagaatc gttcaggagc ccgatgaaga aggaaaaact    900
ttcatattcg aaatcaacgg tgagaaagtc ttcgctaagg gtgctaactg gattccctca    960
gaaaacatcc tcacgtggtt gaaggaggaa gattacgaaa agctcgtcaa aatggcaagg   1020
agtgccaata tgaacatgct cagggtctgg gaggaggaa tctacgagag agagatcttc    1080
tacagactct gtgatgaact cggtatcatg gtgtggcagg atttcatgta cgcgtgtctt   1140
gaatatccgg atcatcttcc gtggttcaga aaactcgcga acgaagaggc aagaaagatt   1200
gtgagaaaac tcagatacca tccctccatt gttctctggt gcggaaacaa cgaaaacaac   1260
tggggattcg atgaatgggg aaatatggcc agaaaagtgg atggtatcaa cctcggaaac   1320
aggctctacc tcttcgattt tcctgagatt tgtgccgaag aagacccgtc cactccctat   1380
tggccatcca gtccatacgg cggtgaaaaa gcgaacagcg aaaaggaagg agacaggcac   1440
gtctggtacg tgtggagtgg ctggatgaac tacgaaaact acgaaaaaga caccggaagg   1500
ttcatcagcg agtttggatt tcagggtgct ccccatccag agacgataga gttcttttca   1560
aaacccgagg aaagagagat attccatccc gtcatgctga agcacaacaa acaggtggaa   1620
ggacaggaaa gattgatcag gttcatattc ggaaattttg gaaagtgtaa agatttcgac   1680
agttttgtgt atctgtccca gctcaaccag gcggaggcga tcaagttcgg tgttgaacac   1740
tggcgaagca ggaagtacaa aacggccggc gctctcttct ggcagttcaa cgacagctgg   1800
ccggtcttca gctggtccgc agtcgattac ttcaaaaggc ccaaagctct ctactactat   1860
gcgagaagat tcttcgctga agttctaccc gttttgaaga agagagacaa caaaatagaa   1920
ctgctggtgg gtgagcgatc tgagggagac aaaagaagtc tctctcaggc ttgcagccta   1980
cgagaagaag ggagaaaagg tattcgaaaa gacttacaga acggtactcc cagcagacgg   2040
tgtgagtttg gttga                                                    2055

<210> SEQ ID NO 59
<211> LENGTH: 2870
<212> TYPE: DNA
<213> ORGANISM: Bankia gouldi

<400> SEQUENCE: 59
atgaaaaaaa atctactaat gtttaaaagg cttacgtatc taccttttgtt tttaatgctg    60
ctctcactaa gttcagtagc tcaatctcct gtagaaaaac atggccgttt acaagttgac   120
ggaaaccgca ttcttaatgc gtctggagaa attacgagct tagctggtaa cagcctctttt   180
tggagtaatg ctggagacac ctccgatttt tataatgcag aaactgttga tttttttagca   240
gaaaactgga atagctcact tattagaata gctatgggcg taaaagaaaa ttgggatggc   300
ggaaatggct atattgatag tccgcaggag caagaagcta aaattagaaa agttattgat   360
gcagctattg ctaacggcat atatgtaata atagactggc acactcacga agcagagtta   420
tacacagatg aggctgttga cttttttacc agaatggcag acctatacgg agatactccc   480
aatgtaatgt atgaaattta taacgagcct atataccaaa gttggcctgt tattaagaat   540
tatgcagagc aagtaattgc tggtatacgt tctaaagacc cagataattt aataattgta   600
ggtactagca attattctca gcaagttgat gtagcatcag cagacccaat atctgatact   660
aatgtggcat atactttaca ttttatgca gcatttaacc cgcatgataa cttaagaaat   720
gtagcacaga cagcattaga taataatgtt gctttgtttg ttacagaatg gggtacaatt   780
ttaaataccg acaaggaga accagacaaa gaaagcacta atacttggat ggcctttttg   840
aagaaaaag gtataagtca cgctaattgg tctttgagtg acaaagcttt tcctgaaaca   900
```

```
gggtctgtag ttcaagcagg acaaggtgta tctggttta ttagcaataa acttacagcc    960
tctggtgaaa ttgtaaaaaa catcatccaa aactgggata cagagacctc tacaggacct   1020
aaaacaacac aatgtagtac tatagaatgt attagagctg caatggaaac agcacaagca   1080
ggagatgaaa ttataattgc ccctggaaac tacaattttc aagacaagat acaaggtgcc   1140
tttaaccgta gtgtttacct ttatggtagt gctaacggaa acagtacaaa ccctattata   1200
ttaagaggcg aaagcgctac aaaccctcct gttttctcag gattagatta taacaatggc   1260
tacctattaa gtattgaagg tgattattgg aatattaaag atatagagtt taaaactggg   1320
tctaaaggta ttgttcttga caattctaat ggtagtaaat taaaaaacct tgttgttcat   1380
gatattggag aagaagctat tcacttgcgt gatggatcta gcaataatag tatagatggt   1440
tgcactatat acaatacagg tagaactaaa cctggttttg gtgaaggttt atatgtaggc   1500
tcagataaag gacaacatga cacttatgaa agagcttgta acaataacac tattgaaaac   1560
tgtaccgttg gacccaatgt aacagcagaa ggcgtagatg ttaaggaagg tacaatgaac   1620
actattataa gaaattgcgt gttttctgca gaaggaattt caggagaaaa tagctcagat   1680
gcttttattg atttaaaagg agcctatggt tttgtataca gaaacacgtt taatgttgat   1740
ggttctgaag taataaatac tggagtagac ttttagata gaggtacagg atttaataca   1800
ggttttagaa atgcaatatt tgaaaataca tataaccttg gcagtagagc ttcagaaatt   1860
tcaactgctc gtaaaaaaca aggttctcct gaacaaactc acgtttggga taatattaga   1920
aaccctaatt ctgttgattt tccaataagt gatggtacag aaaatctagt aaataaattc   1980
tgcccagatt ggaatataga accatgtaat cctgtagacg aaaccaacca agcacctaca   2040
ataagcttcc tatctcctgt taacaatatt actttagttg aaggttataa tttacaagtt   2100
gaagttaatg ctactgatgc agatggaact attgataatg taaaactta tatagataac   2160 aatttagtta ggcaaataaa ttctacttca tataaatggg gccattctga ttctccaaat   2220
acagatgaac ttaatggtct tacagaagga acttataccct aaaagcaat tgcaactgat   2280 aacgacgggg cttctacaga aacgcaattt acgttaactg taataacaga acaagtccg   2340 tctgagaatt gtgactttaa tacaccttct tcaactggtt tagaagattt tgacattaaa   2400
agtttttcta acgttttga gttaggatct ggcggaccat cttaagtaa tttaaaaaaca   2460 tttactatta attggaattc gcaatacaat gggttatatc aatttcaat aaacacaaac   2520 aacggtgtac ctgattatta tataaatta aaaccaaaaaa ttaccttca gtttaaaaaat   2580 gcaaatccaa aaatatctat tagcaatagc ttaattccta atttgatgg tgattactgg   2640 gtaacatcag ataacggtaa ttttgtgatg gtatctaaaa ctaataattt tacgatatac   2700
tttagtaatg acgctactgc tcctatttgt aatgttacgc ctagtaacca aataagtaaa   2760
attactgatg attctagtat taattttaag ctttaccctaa tcctgcttt agacgaaact   2820 atttttgtga gcgctgaaga tgaaaaacta gctttggtgc ttgtaccagt             2870
```

<210> SEQ ID NO 60
<211> LENGTH: 960
<212> TYPE: DNA
<213> ORGANISM: Pyrococcus furiosus

<400> SEQUENCE: 60

```
atgagcaaga aaagttcgt catcgtatct atcttaacaa tccttttagt acaggcaata    60 tatttttgtag aaaagtatca tacctctgag gacaagtcaa cttcaaatac ctcatctaca   120
```

```
ccaccccaaa caacactttc cactaccaag gttctcaaga ttagatacccc tgatgacggt    180 gagtggccag gagctcctat tgataaggat ggtgatggga acccagaatt ctacattgaa    240
ataaacctat ggaacattct taatgctact ggatttgctg agatgacgta caatttaacc    300
agcggcgtcc ttcactacgt ccaacaactt gacaacattg tcttgaggga tagaagtaat    360
tgggtgcatg gataccccga atattctat ggaaacaagc catggaatgc aaactacgca    420
actgatggcc caataccatt acccagtaaa gtttcaaacc taacagactt ctatctaaca    480
atctcctata aacttgagcc caagaacggc ctgccaatta acttcgcaat agaatcctgg    540
ttaacgagag aagcttggag aacaacagga attaacagcg atgagcaaga agtaatgata    600
tggatttact atgacggatt acaaccggct ggctccaaag ttaaggagat tgtagtccca    660
ataatagtta acggaacacc agtaaatgct acatttgaag tatggaaggc aaacattggt    720
tgggagtatg ttgcatttag aataaagacc ccaatcaaag agggaacagt gacaattcca    780
tacggagcat ttataagtgt tgcagccaac atttcaagct taccaaatta cacagaactt    840
tacttagagg acgtggagat tggaactgag tttggaacgc caagcactac ctccgcccac    900
ctagagtggt ggatcacaaa cataacacta actcctctag atagacctct tatttcctaa    960
```

```
<210> SEQ ID NO 61
<211> LENGTH: 663
<212> TYPE: PRT
<213> ORGANISM: Thermotoga maritima

<400> SEQUENCE: 61

Leu Leu Leu Ile Val Glu Leu Ser Phe Val Leu Phe Ala Ser Asp Glu
 1               5                  10                  15

Phe Val Lys Val Glu Asn Gly Lys Phe Ala Leu Asn Gly Lys Glu Phe
            20                  25                  30

Arg Phe Ile Gly Ser Asn Asn Tyr Tyr Met His Tyr Lys Ser Asn Gly
        35                  40                  45

Met Ile Asp Ser Val Leu Glu Ser Ala Arg Asp Met Gly Ile Lys Val
    50                  55                  60

Leu Arg Ile Trp Gly Phe Leu Asp Gly Glu Ser Tyr Cys Arg Asp Lys
65                  70                  75                  80

Asn Thr Tyr Met His Pro Glu Pro Gly Val Phe Gly Val Pro Glu Gly
                85                  90                  95

Ile Ser Asn Ala Gln Ser Gly Phe Glu Arg Leu Asp Tyr Thr Val Ala
            100                 105                 110

Lys Ala Lys Glu Leu Gly Ile Lys Leu Val Ile Leu Val Asn Asn
        115                 120                 125

Trp Asp Asp Phe Gly Gly Met Asn Gln Tyr Val Arg Trp Phe Gly Gly
    130                 135                 140

Thr His His Asp Asp Phe Tyr Arg Asp Glu Lys Ile Lys Glu Glu Tyr
145                 150                 155                 160

Lys Lys Tyr Val Ser Phe Leu Val Asn His Val Asn Thr Tyr Thr Gly
                165                 170                 175

Val Pro Tyr Arg Glu Glu Pro Thr Ile Met Ala Trp Glu Leu Ala Asn
            180                 185                 190

Glu Pro Arg Cys Glu Thr Asp Lys Ser Gly Asn Thr Leu Val Glu Trp
        195                 200                 205

Val Lys Glu Met Ser Ser Tyr Ile Lys Ser Leu Asp Pro Asn His Leu
    210                 215                 220

Val Ala Val Gly Asp Glu Gly Phe Phe Ser Asn Tyr Glu Gly Phe Lys
```

```
            225                 230                 235                 240
Pro Tyr Gly Gly Glu Ala Glu Trp Ala Tyr Asn Gly Trp Ser Gly Val
                245                 250                 255
Asp Trp Lys Lys Leu Leu Ser Ile Glu Thr Val Asp Phe Gly Thr Phe
                260                 265                 270
His Leu Tyr Pro Ser His Trp Gly Val Ser Pro Glu Asn Tyr Ala Gln
                275                 280                 285
Trp Gly Ala Lys Trp Ile Glu Asp His Ile Lys Ile Ala Lys Glu Ile
            290                 295                 300
Gly Lys Pro Val Val Leu Glu Glu Tyr Gly Ile Pro Lys Ser Ala Pro
305                 310                 315                 320
Val Asn Arg Thr Ala Ile Tyr Arg Leu Trp Asn Asp Leu Val Tyr Asp
                325                 330                 335
Leu Gly Gly Asp Gly Ala Met Phe Trp Met Leu Ala Gly Ile Gly Glu
                340                 345                 350
Gly Ser Asp Arg Asp Glu Arg Gly Tyr Tyr Pro Asp Tyr Asp Gly Phe
                355                 360                 365
Arg Ile Val Asn Asp Asp Ser Pro Glu Ala Glu Leu Ile Arg Glu Tyr
            370                 375                 380
Ala Lys Leu Phe Asn Thr Gly Glu Asp Ile Arg Glu Asp Thr Cys Ser
385                 390                 395                 400
Phe Ile Leu Pro Lys Asp Gly Met Glu Ile Lys Lys Thr Val Glu Val
                405                 410                 415
Arg Ala Gly Val Phe Asp Tyr Ser Asn Thr Phe Glu Lys Leu Ser Val
                420                 425                 430
Lys Val Glu Asp Leu Val Phe Glu Asn Glu Ile Glu His Leu Gly Tyr
            435                 440                 445
Gly Ile Tyr Gly Phe Asp Leu Asp Thr Thr Arg Ile Pro Asp Gly Glu
            450                 455                 460
His Glu Met Phe Leu Glu Gly His Phe Gln Gly Lys Thr Val Lys Asp
465                 470                 475                 480
Ser Ile Lys Ala Lys Val Val Asn Glu Ala Arg Tyr Val Leu Ala Glu
                485                 490                 495
Glu Val Asp Phe Ser Ser Pro Glu Glu Val Lys Asn Trp Trp Asn Ser
                500                 505                 510
Gly Thr Trp Gln Ala Glu Phe Gly Ser Pro Asp Ile Glu Trp Asn Gly
            515                 520                 525
Glu Val Gly Asn Gly Ala Leu Gln Leu Asn Val Lys Leu Pro Gly Lys
            530                 535                 540
Ser Asp Trp Glu Glu Val Arg Val Ala Arg Lys Phe Glu Arg Leu Ser
545                 550                 555                 560
Glu Cys Glu Ile Leu Glu Tyr Asp Ile Tyr Ile Pro Asn Val Glu Gly
                565                 570                 575
Leu Lys Gly Arg Leu Arg Pro Tyr Ala Val Leu Asn Pro Gly Trp Val
                580                 585                 590
Lys Ile Gly Leu Asp Met Asn Asn Ala Asn Val Glu Ser Ala Glu Ile
            595                 600                 605
Ile Thr Phe Gly Gly Lys Glu Tyr Arg Arg Phe His Val Arg Ile Glu
            610                 615                 620
Phe Asp Arg Thr Ala Gly Val Lys Glu Leu His Ile Gly Val Val Gly
625                 630                 635                 640
Asp His Leu Arg Tyr Asp Gly Pro Ile Phe Ile Asp Asn Val Arg Leu
                645                 650                 655
```

Tyr Lys Arg Thr Gly Gly Met
            660

<210> SEQ ID NO 62
<211> LENGTH: 684
<212> TYPE: PRT
<213> ORGANISM: Thermotoga maritima

<400> SEQUENCE: 62

Met Lys Arg Ile Asp Leu Asn Gly Phe Trp Ser Val Arg Asp Asn Glu
 1               5                  10                  15

Gly Arg Phe Ser Phe Glu Gly Thr Val Pro Gly Val Val Gln Ala Asp
            20                  25                  30

Leu Val Arg Lys Gly Leu Leu Pro His Pro Tyr Val Gly Met Asn Glu
        35                  40                  45

Asp Leu Phe Lys Glu Ile Glu Asp Arg Glu Trp Ile Tyr Glu Arg Glu
    50                  55                  60

Phe Glu Phe Lys Glu Asp Val Lys Glu Gly Arg Val Asp Leu Val
65                  70                  75                  80

Phe Glu Gly Val Asp Thr Leu Ser Asp Val Tyr Leu Asn Gly Val Tyr
                85                  90                  95

Leu Gly Ser Thr Glu Asp Met Phe Ile Glu Tyr Arg Phe Asp Val Thr
            100                 105                 110

Asn Val Leu Lys Glu Lys Asn His Leu Lys Val Tyr Ile Lys Ser Pro
        115                 120                 125

Ile Arg Val Pro Lys Thr Leu Glu Gln Asn Tyr Gly Val Leu Gly Gly
    130                 135                 140

Pro Glu Asp Pro Ile Arg Gly Tyr Ile Arg Lys Ala Gln Tyr Ser Tyr
145                 150                 155                 160

Gly Trp Asp Trp Gly Ala Arg Ile Val Thr Ser Gly Ile Trp Lys Pro
                165                 170                 175

Val Tyr Leu Glu Val Tyr Arg Ala Arg Leu Gln Asp Ser Thr Ala Tyr
            180                 185                 190

Leu Leu Glu Leu Glu Gly Lys Asp Ala Leu Val Arg Val Asn Gly Phe
        195                 200                 205

Val His Gly Glu Gly Asn Leu Ile Val Glu Val Tyr Val Asn Gly Glu
    210                 215                 220

Lys Ile Gly Glu Phe Pro Val Leu Glu Lys Asn Gly Glu Lys Leu Phe
225                 230                 235                 240

Asp Gly Val Phe His Leu Lys Asp Val Lys Leu Trp Tyr Pro Trp Asn
                245                 250                 255

Val Gly Lys Pro Tyr Leu Tyr Asp Phe Val Phe Val Leu Lys Asp Leu
            260                 265                 270

Asn Gly Glu Ile Tyr Arg Glu Lys Lys Ile Gly Leu Arg Arg Val
        275                 280                 285

Arg Ile Val Gln Glu Pro Asp Glu Glu Gly Lys Thr Phe Ile Phe Glu
    290                 295                 300

Ile Asn Gly Glu Lys Val Phe Ala Lys Gly Ala Asn Trp Ile Pro Ser
305                 310                 315                 320

Glu Asn Ile Leu Thr Trp Leu Lys Glu Glu Asp Tyr Glu Lys Leu Val
                325                 330                 335

Lys Met Ala Arg Ser Ala Asn Met Asn Met Leu Arg Val Trp Gly Gly
            340                 345                 350

Gly Ile Tyr Glu Arg Glu Ile Phe Tyr Arg Leu Cys Asp Glu Leu Gly

```
                    355                 360                 365
Ile Met Val Trp Gln Asp Phe Met Tyr Ala Cys Leu Glu Tyr Pro Asp
    370                 375                 380

His Leu Pro Trp Phe Arg Lys Leu Ala Asn Glu Glu Ala Arg Lys Ile
385                 390                 395                 400

Val Arg Lys Leu Arg Tyr His Pro Ser Ile Val Leu Trp Cys Gly Asn
                405                 410                 415

Asn Glu Asn Asn Trp Gly Phe Asp Glu Trp Gly Asn Met Ala Arg Lys
                420                 425                 430

Val Asp Gly Ile Asn Leu Gly Asn Arg Leu Tyr Leu Phe Asp Phe Pro
                435                 440                 445

Glu Ile Cys Ala Glu Glu Asp Pro Ser Thr Pro Tyr Trp Pro Ser Ser
    450                 455                 460

Pro Tyr Gly Gly Leu Lys Ala Asn Ser Glu Lys Glu Gly Asp Arg His
465                 470                 475                 480

Val Trp Tyr Val Trp Ser Gly Trp Met Asn Tyr Glu Asn Tyr Glu Lys
                485                 490                 495

Asp Thr Gly Arg Phe Ile Ser Glu Phe Gly Phe Gln Gly Ala Pro His
                500                 505                 510

Pro Glu Thr Ile Glu Phe Phe Ser Lys Pro Glu Glu Arg Glu Ile Phe
                515                 520                 525

His Pro Val Met Leu Lys His Asn Lys Gln Val Glu Gly Gln Glu Arg
    530                 535                 540

Leu Ile Arg Phe Ile Phe Gly Asn Phe Gly Lys Cys Lys Asp Phe Asp
545                 550                 555                 560

Ser Phe Val Tyr Leu Ser Gln Leu Asn Gln Ala Glu Ala Ile Lys Phe
                565                 570                 575

Gly Val Glu His Trp Arg Ser Arg Lys Tyr Lys Thr Ala Gly Ala Leu
                580                 585                 590

Phe Trp Gln Phe Asn Asp Ser Trp Pro Val Phe Ser Trp Ser Ala Val
                595                 600                 605

Asp Tyr Phe Lys Arg Pro Lys Ala Leu Tyr Tyr Tyr Ala Arg Arg Phe
    610                 615                 620

Phe Ala Glu Val Leu Pro Val Leu Lys Lys Arg Asp Asn Lys Ile Glu
625                 630                 635                 640

Leu Leu Val Gly Glu Arg Ser Glu Gly Asp Lys Arg Ser Leu Ser Gln
                645                 650                 655

Ala Cys Ser Leu Arg Glu Glu Gly Arg Lys Gly Ile Arg Lys Asp Leu
                660                 665                 670

Gln Asn Gly Thr Pro Ser Arg Arg Cys Glu Phe Gly
                675                 680

<210> SEQ ID NO 63
<211> LENGTH: 956
<212> TYPE: PRT
<213> ORGANISM: Bankia gouldi

<400> SEQUENCE: 63

Met Lys Lys Asn Leu Leu Met Phe Lys Arg Leu Thr Tyr Leu Pro Leu
1               5                   10                  15

Phe Leu Met Leu Leu Ser Leu Ser Ser Val Ala Gln Ser Pro Val Glu
                20                  25                  30

Lys His Gly Arg Leu Gln Val Asp Gly Asn Arg Ile Leu Asn Ala Ser
                35                  40                  45
```

Gly Glu Ile Thr Ser Leu Ala Gly Asn Ser Leu Phe Trp Ser Asn Ala
50              55                  60

Gly Asp Thr Ser Asp Phe Tyr Asn Ala Glu Thr Val Asp Phe Leu Ala
65              70                  75                  80

Glu Asn Trp Asn Ser Ser Leu Ile Arg Ile Ala Met Gly Val Lys Glu
                85                  90                  95

Asn Trp Asp Gly Gly Asn Gly Tyr Ile Asp Ser Pro Gln Glu Gln Glu
            100                 105                 110

Ala Lys Ile Arg Lys Val Ile Asp Ala Ala Ile Ala Asn Gly Ile Tyr
            115                 120                 125

Val Ile Ile Asp Trp His Thr His Glu Ala Glu Leu Tyr Thr Asp Glu
130             135                 140

Ala Val Asp Phe Phe Thr Arg Met Ala Asp Leu Tyr Gly Asp Thr Pro
145             150                 155                 160

Asn Val Met Tyr Glu Ile Tyr Asn Glu Pro Ile Tyr Gln Ser Trp Pro
                165                 170                 175

Val Ile Lys Asn Tyr Ala Glu Gln Val Ile Ala Gly Ile Arg Ser Lys
            180                 185                 190

Asp Pro Asp Asn Leu Ile Ile Val Gly Thr Ser Asn Tyr Ser Gln Gln
            195                 200                 205

Val Asp Val Ala Ser Ala Asp Pro Ile Ser Asp Thr Asn Val Ala Tyr
210             215                 220

Thr Leu His Phe Tyr Ala Ala Phe Asn Pro His Asp Asn Leu Arg Asn
225             230                 235                 240

Val Ala Gln Thr Ala Leu Asp Asn Asn Val Ala Leu Phe Val Thr Glu
                245                 250                 255

Trp Gly Thr Ile Leu Asn Thr Gly Gln Gly Glu Pro Asp Lys Glu Ser
            260                 265                 270

Thr Asn Thr Trp Met Ala Phe Leu Lys Glu Lys Gly Ile Ser His Ala
            275                 280                 285

Asn Trp Ser Leu Ser Asp Lys Ala Phe Pro Glu Thr Gly Ser Val Val
290             295                 300

Gln Ala Gly Gln Gly Val Ser Gly Leu Ile Ser Asn Lys Leu Thr Ala
305             310                 315                 320

Ser Gly Glu Ile Val Lys Asn Ile Ile Gln Asn Trp Asp Thr Glu Thr
                325                 330                 335

Ser Thr Gly Pro Lys Thr Thr Gln Cys Ser Thr Ile Glu Cys Ile Arg
            340                 345                 350

Ala Ala Met Glu Thr Ala Gln Ala Gly Asp Glu Ile Ile Ile Ala Pro
            355                 360                 365

Gly Asn Tyr Asn Phe Gln Asp Lys Ile Gln Gly Ala Phe Asn Arg Ser
370             375                 380

Val Tyr Leu Tyr Gly Ser Ala Asn Gly Asn Ser Thr Asn Pro Ile Ile
385             390                 395                 400

Leu Arg Gly Glu Ser Ala Thr Asn Pro Pro Val Phe Ser Gly Leu Asp
                405                 410                 415

Tyr Asn Asn Gly Tyr Leu Leu Ser Ile Glu Gly Asp Tyr Trp Asn Ile
            420                 425                 430

Lys Asp Ile Glu Phe Lys Thr Gly Ser Lys Gly Ile Val Leu Asp Asn
            435                 440                 445

Ser Asn Gly Ser Lys Leu Lys Asn Leu Val Val His Asp Ile Gly Glu
450             455                 460

Glu Ala Ile His Leu Arg Asp Gly Ser Ser Asn Asn Ser Ile Asp Gly

```
                465                 470                 475                 480
Cys Thr Ile Tyr Asn Thr Gly Arg Thr Lys Pro Gly Phe Gly Glu Gly
                    485                 490                 495
Leu Tyr Val Gly Ser Asp Lys Gly Gln His Asp Thr Tyr Glu Arg Ala
                    500                 505                 510
Cys Asn Asn Thr Ile Glu Asn Cys Thr Val Gly Pro Asn Val Thr
                    515                 520                 525
Ala Glu Gly Val Asp Val Lys Glu Gly Thr Met Asn Thr Ile Ile Arg
                530                 535                 540
Asn Cys Val Phe Ser Ala Glu Gly Ile Ser Gly Glu Asn Ser Ser Asp
545                 550                 555                 560
Ala Phe Ile Asp Leu Lys Gly Ala Tyr Gly Phe Val Tyr Arg Asn Thr
                    565                 570                 575
Phe Asn Val Asp Gly Ser Glu Val Ile Asn Thr Gly Val Asp Phe Leu
                    580                 585                 590
Asp Arg Gly Thr Gly Phe Asn Thr Gly Phe Arg Asn Ala Ile Phe Glu
                    595                 600                 605
Asn Thr Tyr Asn Leu Gly Ser Arg Ala Ser Glu Ile Ser Thr Ala Arg
                610                 615                 620
Lys Lys Gln Gly Ser Pro Glu Gln Thr His Val Trp Asp Asn Ile Arg
625                 630                 635                 640
Asn Pro Asn Ser Val Asp Phe Pro Ile Ser Asp Gly Thr Glu Asn Leu
                    645                 650                 655
Val Asn Lys Phe Cys Pro Asp Trp Asn Ile Glu Pro Cys Asn Pro Val
                    660                 665                 670
Asp Glu Thr Asn Gln Ala Pro Thr Ile Ser Phe Leu Ser Pro Val Asn
                    675                 680                 685
Asn Ile Thr Leu Val Glu Gly Tyr Asn Leu Gln Val Glu Val Asn Ala
                    690                 695                 700
Thr Asp Ala Asp Gly Thr Ile Asp Asn Val Lys Leu Tyr Ile Asp Asn
705                 710                 715                 720
Asn Leu Val Arg Gln Ile Asn Ser Thr Ser Tyr Lys Trp Gly His Ser
                    725                 730                 735
Asp Ser Pro Asn Thr Asp Glu Leu Asn Gly Leu Thr Glu Gly Thr Tyr
                    740                 745                 750
Thr Leu Lys Ala Ile Ala Thr Asp Asn Asp Gly Ala Ser Thr Glu Thr
                    755                 760                 765
Gln Phe Thr Leu Thr Val Ile Thr Glu Gln Ser Pro Ser Glu Asn Cys
                770                 775                 780
Asp Phe Asn Thr Pro Ser Ser Thr Gly Leu Glu Asp Phe Asp Ile Lys
785                 790                 795                 800
Lys Phe Ser Asn Val Phe Glu Leu Gly Ser Gly Pro Ser Leu Ser
                    805                 810                 815
Asn Leu Lys Thr Phe Thr Ile Asn Trp Asn Ser Gln Tyr Asn Gly Leu
                    820                 825                 830
Tyr Gln Phe Ser Ile Asn Thr Asn Asn Gly Val Pro Asp Tyr Tyr Ile
                835                 840                 845
Asn Leu Lys Pro Lys Ile Thr Phe Gln Phe Lys Asn Ala Asn Pro Glu
                    850                 855                 860
Ile Ser Ile Ser Asn Ser Leu Ile Pro Asn Phe Asp Gly Asp Tyr Trp
865                 870                 875                 880
Val Thr Ser Asp Asn Gly Asn Phe Val Met Val Ser Lys Thr Asn Asn
                    885                 890                 895
```

```
Phe Thr Ile Tyr Phe Ser Asn Asp Ala Thr Ala Pro Ile Cys Asn Val
                900                 905                 910

Thr Pro Ser Asn Gln Ile Ser Lys Ile Thr Asp Asp Ser Ser Ile Asn
            915                 920                 925

Phe Lys Leu Tyr Pro Asn Pro Ala Leu Asp Glu Thr Ile Phe Val Ser
            930                 935                 940

Ala Glu Asp Glu Lys Leu Ala Leu Val Leu Val Pro
945                 950                 955

<210> SEQ ID NO 64
<211> LENGTH: 319
<212> TYPE: PRT
<213> ORGANISM: Pyrococcus furiosus

<400> SEQUENCE: 64

Met Ser Lys Lys Lys Phe Val Ile Val Ser Ile Leu Thr Ile Leu Leu
1               5                   10                  15

Val Gln Ala Ile Tyr Phe Val Glu Lys Tyr His Thr Ser Glu Asp Lys
            20                  25                  30

Ser Thr Ser Asn Thr Ser Ser Thr Pro Pro Gln Thr Thr Leu Ser Thr
        35                  40                  45

Thr Lys Val Leu Lys Ile Arg Tyr Pro Asp Asp Gly Glu Trp Pro Gly
50                  55                  60

Ala Pro Ile Asp Lys Asp Gly Asp Gly Asn Pro Glu Phe Tyr Ile Glu
65                  70                  75                  80

Ile Asn Leu Trp Asn Ile Leu Asn Ala Thr Gly Phe Ala Glu Met Thr
                85                  90                  95

Tyr Asn Leu Thr Ser Gly Val Leu His Tyr Val Gln Gln Leu Asp Asn
            100                 105                 110

Ile Val Leu Arg Asp Arg Ser Asn Trp Val His Gly Tyr Pro Glu Ile
        115                 120                 125

Phe Tyr Gly Asn Lys Pro Trp Asn Ala Asn Tyr Ala Thr Asp Gly Pro
130                 135                 140

Ile Pro Leu Pro Ser Lys Val Ser Asn Leu Thr Asp Phe Tyr Leu Thr
145                 150                 155                 160

Ile Ser Tyr Lys Leu Glu Pro Lys Asn Gly Leu Pro Ile Asn Phe Ala
                165                 170                 175

Ile Glu Ser Trp Leu Thr Arg Glu Ala Trp Arg Thr Thr Gly Ile Asn
            180                 185                 190

Ser Asp Glu Gln Glu Val Met Ile Trp Ile Tyr Tyr Asp Gly Leu Gln
        195                 200                 205

Pro Ala Gly Ser Lys Val Lys Glu Ile Val Pro Ile Ile Val Asn
210                 215                 220

Gly Thr Pro Val Asn Ala Thr Phe Glu Val Trp Lys Ala Asn Ile Gly
225                 230                 235                 240

Trp Glu Tyr Val Ala Phe Arg Ile Lys Thr Pro Ile Lys Glu Gly Thr
                245                 250                 255

Val Thr Ile Pro Tyr Gly Ala Phe Ile Ser Val Ala Ala Asn Ile Ser
            260                 265                 270

Ser Leu Pro Asn Tyr Thr Glu Leu Tyr Leu Glu Asp Val Glu Ile Gly
        275                 280                 285

Thr Glu Phe Gly Thr Pro Ser Thr Thr Ser Ala His Leu Glu Trp Trp
290                 295                 300

Ile Thr Asn Ile Thr Leu Thr Pro Leu Asp Arg Pro Leu Ile Ser
```

<210> SEQ ID NO 65
<211> LENGTH: 52
<212> TYPE: DNA
<213> ORGANISM: Artificial Sequence
<220> FEATURE:
<223> OTHER INFORMATION: synthetically generated oligonucleotide

<400> SEQUENCE: 65
ccgacaattg attaaagagg agaaattaac tatggaaagg atcgatgaaa tt    52

<210> SEQ ID NO 66
<211> LENGTH: 31
<212> TYPE: DNA
<213> ORGANISM: Artificial Sequence
<220> FEATURE:
<223> OTHER INFORMATION: synthetically generated oligonucleotide

<400> SEQUENCE: 66
ctcttctcta gtttggtac tccatggagg c    31

<210> SEQ ID NO 67
<211> LENGTH: 52
<212> TYPE: DNA
<213> ORGANISM: Artificial Sequence
<220> FEATURE:
<223> OTHER INFORMATION: synthetically generated oligonucleotide

<400> SEQUENCE: 67
ccgacaattg attaaagagg agaaattaac tatgttccct gaaaagttcc tt    52

<210> SEQ ID NO 68
<211> LENGTH: 31
<212> TYPE: DNA
<213> ORGANISM: Artificial Sequence
<220> FEATURE:
<223> OTHER INFORMATION: synthetically generated oligonucleotide

<400> SEQUENCE: 68
ctccttaacg actcccctac tccatggagg c    31

<210> SEQ ID NO 69
<211> LENGTH: 27
<212> TYPE: DNA
<213> ORGANISM: Artificial Sequence
<220> FEATURE:
<223> OTHER INFORMATION: synthetically generated oligonucleotide

<400> SEQUENCE: 69
aataaggatc cgtttagcga cgctcgc    27

<210> SEQ ID NO 70
<211> LENGTH: 35
<212> TYPE: DNA
<213> ORGANISM: Artificial Sequence
<220> FEATURE:
<223> OTHER INFORMATION: synthetically generated oligonucleotide

<400> SEQUENCE: 70
cggataatgg cgacatgttg ggccttcgaa aataa    35

<210> SEQ ID NO 71
<211> LENGTH: 52
<212> TYPE: DNA
<213> ORGANISM: Artificial Sequence

```
<220> FEATURE:
<223> OTHER INFORMATION: synthetically generated oligonucleotide

<400> SEQUENCE: 71
aataacaatt gaaggaggaa tttaaatggc ttatcatacc tctgaggaca ag         52

<210> SEQ ID NO 72
<211> LENGTH: 32
<212> TYPE: DNA
<213> ORGANISM: Artificial Sequence
<220> FEATURE:
<223> OTHER INFORMATION: synthetically generated oligonucleotide

<400> SEQUENCE: 72
ctatctggag aataaaggat tcagctgaat aa                               32
```